US010751507B2

(12) United States Patent
Palmer et al.

(10) Patent No.: US 10,751,507 B2
(45) Date of Patent: Aug. 25, 2020

(54) THERMALLY CONTROLLED VARIABLE-FLEXIBILITY CATHETERS AND METHODS OF MANUFACTURING SAME

(71) Applicant: Syntheon Variflex, LLC, Miami, FL (US)

(72) Inventors: Matthew A. Palmer, Miami, FL (US); Thomas O. Bales, Jr., Miami, FL (US); Tyler Bond, Miami, FL (US); Eric Petersen, Homestead, FL (US); Derek Dee Deville, Coral Gables, FL (US); William T. Bales, Miami, FL (US); Matthew Weger, Miami, FL (US)

(73) Assignee: SYN VARIFLEX, LLC, Miami, FL (US)

( * ) Notice: Subject to any disclaimer, the term of this patent is extended or adjusted under 35 U.S.C. 154(b) by 148 days.

(21) Appl. No.: 15/947,505

(22) Filed: Apr. 6, 2018

(65) Prior Publication Data

US 2018/0289925 A1 Oct. 11, 2018

Related U.S. Application Data

(66) Substitute for application No. 62/483,736, filed on Apr. 10, 2017.

(Continued)

(51) Int. Cl.
*A61M 25/00* (2006.01)
*A61M 25/01* (2006.01)
(Continued)

(52) U.S. Cl.
CPC ...... *A61M 25/0054* (2013.01); *A61M 25/005* (2013.01); *A61M 25/0043* (2013.01);
(Continued)

(58) Field of Classification Search
CPC .......... A61M 25/0054; A61M 25/0043; A61M 25/0045; A61M 25/005; A61M 2025/0064; B29K 2995/0082
See application file for complete search history.

(56) References Cited

U.S. PATENT DOCUMENTS 3,359,974 A  12/1967 Khalil
3,557,780 A   1/1971 Sato
(Continued)

FOREIGN PATENT DOCUMENTS

WO  2005048814 A2  6/2005
WO  2007093394 A1  8/2007
(Continued)

OTHER PUBLICATIONS

International Search Report an Written Opinion in PCT/US2018/026877 dated Jun. 11, 2018.
(Continued)

*Primary Examiner* — Nathan R Price
*Assistant Examiner* — Anh Bui
(74) *Attorney, Agent, or Firm* — Gregory L. Mayback; Dickinson Wright PLLC

(57) ABSTRACT

A catheter comprises a heater control supplying power, a handle, a base catheter with lumen and comprising a proximal section and a distal segment, and a variable stiffness element. The element comprises a heater connected to the heater control, coiled at least at the distal segment, and comprising a shaft portion of a first metallic conductive material and a heater portion of a second metallic conductive material. A jacket is disposed about the heater portion. A variable flex sub-assembly between the catheter and jacket comprises a non-conducting braid and a binding material. Without power, the binding material is stiffened. Responsive to heating of the binding material, the binding material
(Continued)

softens to increase flexibility of the variable flex sub-assembly at least at the distal segment. Responsive to removing power, the binding material cools and stiffens to decrease flexibility of the variable flex sub-assembly at least at the distal segment.

23 Claims, 18 Drawing Sheets

Related U.S. Application Data

(60) Provisional application No. 62/644,797, filed on Mar. 19, 2018.

(51) Int. Cl.
*A61B 1/00* (2006.01)
*A61M 25/06* (2006.01)

(52) U.S. Cl.
CPC .... *A61M 25/0045* (2013.01); *A61M 25/0133* (2013.01); *A61B 1/00078* (2013.01); *A61M 25/0009* (2013.01); *A61M 25/0662* (2013.01); *A61M 2025/0064* (2013.01); *B29K 2995/0082* (2013.01)

(56) References Cited

U.S. PATENT DOCUMENTS

| | | | |
|---|---|---|---|
| 3,998,216 A | 12/1976 | Hosono | |
| 4,176,662 A | 12/1979 | Frazer | |
| 4,248,234 A | 2/1981 | Assenza et al. | |
| 4,498,473 A | 2/1985 | Gereg | |
| 4,571,240 A | 2/1986 | Samson et al. | |
| 4,575,185 A | 3/1986 | Wentzell | |
| 4,581,390 A | 4/1986 | Flynn | |
| 4,753,223 A | 6/1988 | Bremer | |
| 4,762,118 A | 8/1988 | Lia et al. | |
| 4,784,636 A | 11/1988 | Rydell | |
| 4,815,450 A | 3/1989 | Patel | |
| 4,817,613 A | 4/1989 | Jaraczewski et al. | |
| 4,838,859 A | 6/1989 | Strassmann | |
| 4,848,364 A | 7/1989 | Bosman | |
| 4,890,602 A | 1/1990 | Hake | |
| 4,893,613 A | 1/1990 | Hake | |
| 4,909,787 A | 3/1990 | Danforth | |
| 4,984,581 A | 1/1991 | Stice | |
| 4,998,282 A | 3/1991 | Shishido et al. | |
| 5,069,674 A | 12/1991 | Fearnot et al. | |
| 5,143,085 A | 9/1992 | Wilson | |
| 5,211,633 A | 5/1993 | Stouder, Jr. | |
| 5,222,938 A | 6/1993 | Behl | |
| D337,733 S | 7/1993 | Ewing et al. | |
| 5,240,135 A | 8/1993 | Lepinoy | |
| 5,259,366 A | 11/1993 | Reydel et al. | |
| 5,271,382 A | 12/1993 | Chikama | |
| 5,337,733 A | 8/1994 | Bauerfeind et al. | |
| 5,357,979 A | 10/1994 | Imran | |
| 5,386,817 A | 2/1995 | Jones | |
| 5,423,771 A | 6/1995 | Imran | |
| 5,454,795 A | 10/1995 | Samson | |
| 5,531,685 A | 7/1996 | Hemmer et al. | |
| 5,577,992 A | 11/1996 | Chiba et al. | |
| 5,649,941 A | 7/1997 | Lary | |
| 5,738,100 A | 4/1998 | Yagami et al. | |
| 5,759,151 A | 6/1998 | Sturges | |
| 5,807,237 A | 9/1998 | Tindel | |
| 5,851,203 A * | 12/1998 | van Muiden | A61M 25/0054 604/525 |
| 5,873,816 A | 2/1999 | Kagawa et al. | |
| 5,897,536 A | 4/1999 | Nap et al. | |
| 5,931,819 A | 8/1999 | Fariabi | |
| 5,938,623 A | 8/1999 | Quiachon et al. | |
| 6,024,740 A | 2/2000 | Lesh et al. | |
| 6,030,405 A | 2/2000 | Zarbatany et al. | |
| 6,117,068 A | 9/2000 | Gourley et al. | |
| 6,123,084 A | 9/2000 | Jandak et al. | |
| 6,146,339 A | 11/2000 | Biagtan et al. | |
| 6,159,187 A | 12/2000 | Park et al. | |
| 6,196,967 B1 | 3/2001 | Lim et al. | |
| 6,217,565 B1 * | 4/2001 | Cohen | A61M 25/005 604/525 |
| 6,309,412 B1 | 10/2001 | Lau et al. | |
| 6,346,077 B1 | 2/2002 | Taylor et al. | |
| 6,375,654 B1 | 4/2002 | McIntyre | |
| 6,387,044 B1 | 5/2002 | Tachibana et al. | |
| 6,451,005 B1 * | 9/2002 | Saitou | A61M 25/0053 604/526 |
| 6,468,203 B2 | 10/2002 | Belson | |
| 6,478,731 B2 | 11/2002 | Speier et al. | |
| 6,506,150 B1 | 1/2003 | Ouchi | |
| 6,517,477 B1 | 2/2003 | Wendlandt | |
| 6,533,752 B1 | 3/2003 | Waram et al. | |
| 6,562,021 B1 | 5/2003 | Derbin et al. | |
| 6,602,242 B1 * | 8/2003 | Fung | A61B 18/1492 600/373 |
| 6,610,007 B2 | 8/2003 | Belson et al. | |
| 6,645,223 B2 | 11/2003 | Boyle et al. | |
| 6,800,056 B2 | 10/2004 | Tartaglia et al. | |
| 6,802,809 B2 | 10/2004 | Okada | |
| 6,858,005 B2 | 2/2005 | Ohline et al. | |
| 6,887,235 B2 | 5/2005 | O'Connor et al. | |
| 6,926,669 B1 | 8/2005 | Stewart | |
| 6,942,613 B2 | 9/2005 | Ewers et al. | |
| 6,974,411 B2 | 12/2005 | Belson | |
| 6,984,203 B2 | 1/2006 | Tartaglia et al. | |
| 7,066,880 B2 | 6/2006 | Wendlandt | |
| 7,066,931 B2 | 6/2006 | O'Connor et al. | |
| 7,104,951 B2 | 9/2006 | Hasegawa et al. | |
| 7,291,127 B2 | 11/2007 | Eidenschink | |
| 7,435,214 B2 | 10/2008 | Kucklick et al. | |
| 7,465,308 B2 | 12/2008 | Sikora et al. | |
| 7,559,916 B2 | 7/2009 | Smith et al. | |
| 7,736,323 B2 | 6/2010 | Von Weymarn-Scharli | |
| 7,766,896 B2 | 8/2010 | Kornkven Volk et al. | |
| 7,771,411 B2 | 8/2010 | Smith et al. | |
| 7,811,228 B2 | 10/2010 | Adams | |
| 7,998,132 B2 | 8/2011 | Gregorich et al. | |
| 8,092,374 B2 | 1/2012 | Smith et al. | |
| 8,100,838 B2 | 1/2012 | Wright et al. | |
| 8,282,677 B2 | 10/2012 | O'Connor et al. | |
| 8,303,570 B2 | 11/2012 | Gregorich et al. | |
| 8,308,722 B2 * | 11/2012 | Ormsby | A61B 18/1492 606/33 |
| 8,376,960 B2 | 2/2013 | Olson | |
| 8,491,520 B2 | 7/2013 | Smith et al. | |
| 8,523,786 B2 | 9/2013 | Von Weymarn-Scharli | |
| 8,556,804 B2 | 10/2013 | Smith et al. | |
| 8,814,848 B2 | 8/2014 | Gregorich et al. | |
| 8,821,478 B2 | 9/2014 | Hanson et al. | |
| 8,870,817 B2 | 10/2014 | Kappel et al. | |
| 8,876,772 B2 | 11/2014 | Weber et al. | |
| 8,920,870 B2 | 12/2014 | Weber | |
| 9,155,451 B2 | 10/2015 | Smith et al. | |
| 9,295,812 B2 | 3/2016 | Wright et al. | |
| 9,333,322 B2 | 5/2016 | Kappel et al. | |
| 9,439,723 B2 | 9/2016 | Beri | |
| 9,526,862 B2 | 12/2016 | Iijima et al. | |
| 9,586,025 B2 | 3/2017 | Salahieh et al. | |
| 9,623,206 B2 | 4/2017 | Melsheimer | |
| 9,629,980 B2 | 4/2017 | O'Day | |
| 9,649,473 B2 | 5/2017 | Gregorich et al. | |
| 9,827,126 B2 | 11/2017 | Losordo et al. | |
| 9,861,782 B2 | 1/2018 | Plassman et al. | |
| 2002/0002323 A1 | 1/2002 | Moriyama | |
| 2002/0082585 A1 | 6/2002 | Carroll et al. | |
| 2002/0177750 A1 | 11/2002 | Pilvisto | |
| 2003/0125764 A1 | 7/2003 | Brady et al. | |
| 2003/0135198 A1 | 7/2003 | Berhow et al. | |
| 2004/0034383 A1 | 2/2004 | Belson | |
| 2004/0044350 A1 | 3/2004 | Martin et al. | |
| 2004/0054322 A1 | 3/2004 | Vargas | |
| 2004/0138529 A1 | 7/2004 | Wiltshire et al. | |

(56) References Cited

U.S. PATENT DOCUMENTS

| | | |
|---|---|---|
| 2004/0182393 A1 | 9/2004 | MacMillan et al. |
| 2004/0186350 A1 | 9/2004 | Brenneman et al. |
| 2005/0075538 A1 | 4/2005 | Banik et al. |
| 2005/0131279 A1 | 6/2005 | Boulais et al. |
| 2005/0165275 A1 | 7/2005 | Von Felten et al. |
| 2006/0025652 A1 | 2/2006 | Vargas |
| 2006/0069346 A1* | 3/2006 | Smith ............... A61M 25/005 604/95.05 |
| 2006/0129130 A1 | 6/2006 | Tal et al. |
| 2006/0211979 A1 | 9/2006 | Smith et al. |
| 2007/0088367 A1 | 4/2007 | Von Weymarn-Scharli |
| 2007/0093689 A1 | 4/2007 | Steinberg |
| 2007/0179339 A1 | 8/2007 | Gorini et al. |
| 2007/0208300 A1 | 9/2007 | Pravong et al. |
| 2007/0215268 A1 | 9/2007 | Pingleton et al. |
| 2007/0270648 A1 | 11/2007 | Smith et al. |
| 2007/0272648 A1 | 11/2007 | Keiji et al. |
| 2008/0009831 A1 | 1/2008 | Griffin |
| 2008/0091170 A1 | 4/2008 | Vargas et al. |
| 2008/0097399 A1 | 4/2008 | Sachar et al. |
| 2008/0228168 A1 | 9/2008 | Mittermeyer et al. |
| 2008/0269776 A1 | 10/2008 | Justin et al. |
| 2009/0149710 A1 | 6/2009 | Stefanchik et al. |
| 2009/0187163 A1 | 7/2009 | Uihlein |
| 2011/0040282 A1 | 2/2011 | Uihlein |
| 2014/0236120 A1 | 8/2014 | Tsai et al. |
| 2014/0276601 A1 | 9/2014 | Edward |
| 2014/0276642 A1 | 9/2014 | Cully et al. |
| 2015/0272654 A1* | 10/2015 | Esch ................ A61B 18/082 606/34 |
| 2015/0320969 A1 | 11/2015 | Haslinger et al. |
| 2016/0074621 A1 | 3/2016 | Yao et al. |
| 2016/0101261 A1 | 4/2016 | Kugler et al. |
| 2016/0271363 A1 | 9/2016 | Bauer et al. |

FOREIGN PATENT DOCUMENTS

| | | |
|---|---|---|
| WO | 2007131766 A2 | 11/2007 |
| WO | 2010020971 A2 | 2/2010 |
| WO | 2016118671 A1 | 7/2016 |

OTHER PUBLICATIONS

Abstract submitted to A/S/G/E, C W Williams, "A Split Overtube for Easier Colonoscopy", Gastrointestial Endoscopt, 1983, p. 188.

International Search Report and Written Opinion of the International Searching Authority dated Aug. 31, 2006, for International Application No. PCT/US2005/034487.

International Search Report for PCT/US/068348 dated Oct. 30, 2008.

International Search Report for PCT/US07/05478 dated Dec. 17, 2007.

International Search Report for PCT/US07/12179 dated Sep. 12, 2008.

International Search Report for PCT/US07/75701 dated Aug. 29, 2008.

International Search Report for PCT/US08/64084 dated Dec. 9, 2008.

Yarmolenko, et al. NIH Public Access National Institutes of Health, "Thresholds for thermal damage to normal tissues: An update" Int J Hyperthermia. Author manuscript; available in PMC Mar. 27, 2013, 2011 informa UK Ltd.; 27(4): 320-343. doi:10.3109/02656736. 2010.534527.

Cordaro, et al.,"Thermodynamic Properties of Molten Nitrate Salts", Sandia National Laboratories: Senior member, Technical Staff, PHD. Livermore, CA, pp. 1-8.

* cited by examiner

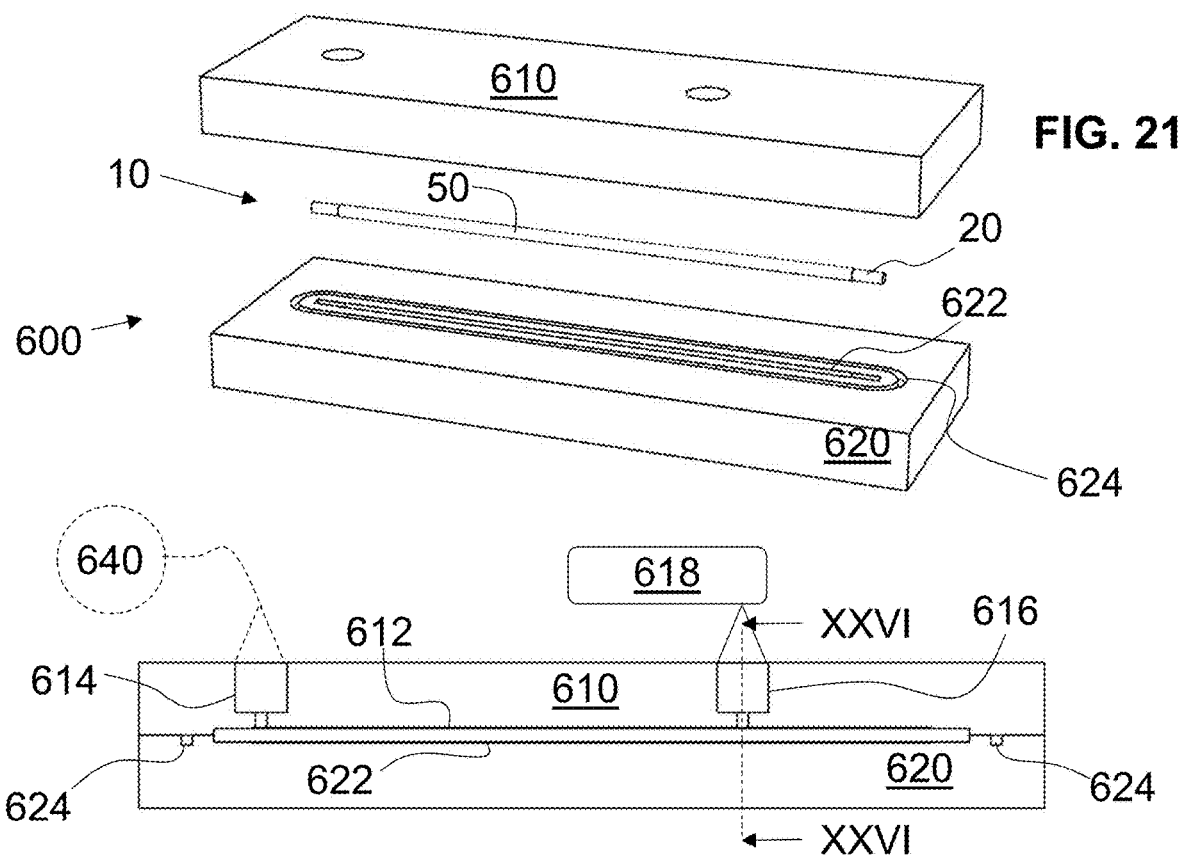
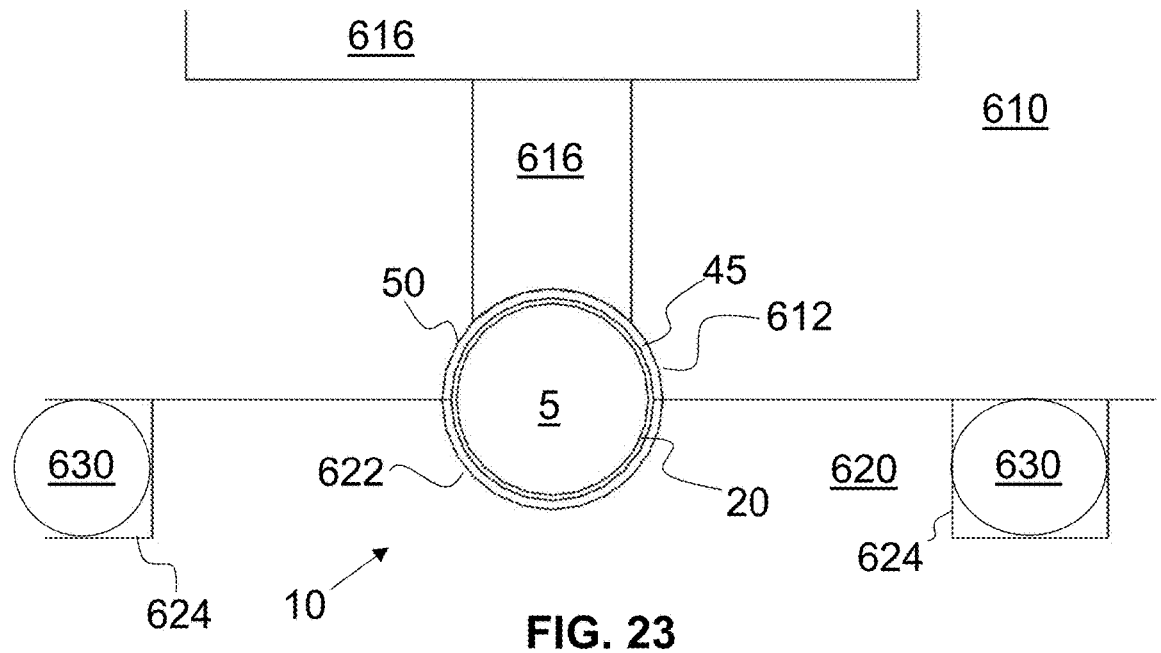

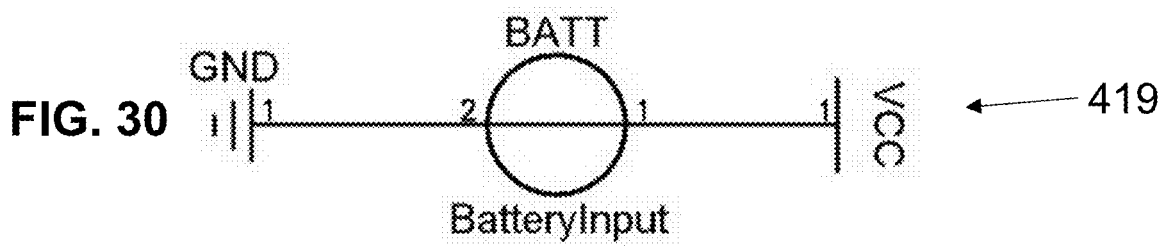
FIG. 30 ← 419
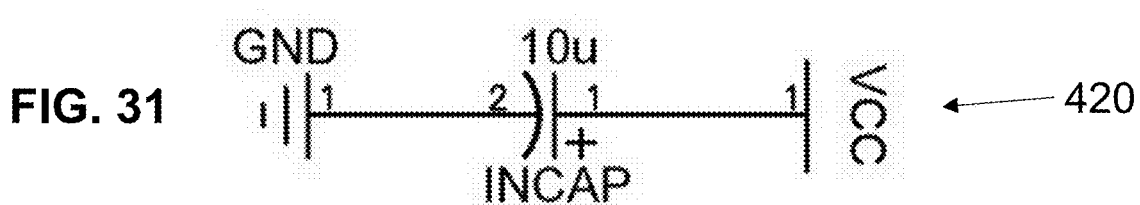
FIG. 31 ← 420
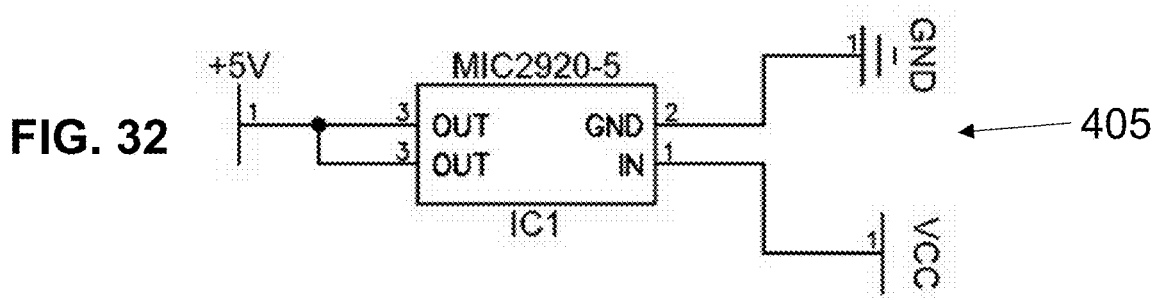
FIG. 32 ← 405
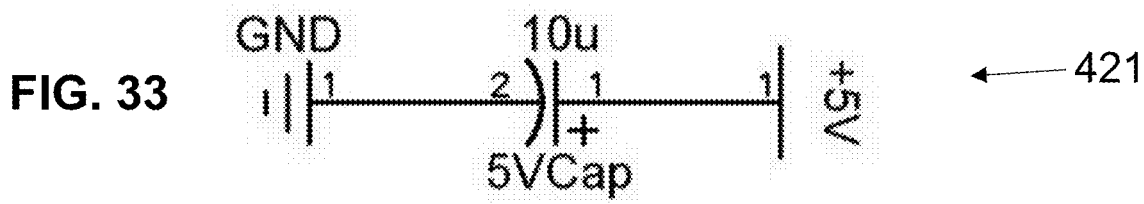
FIG. 33 ← 421
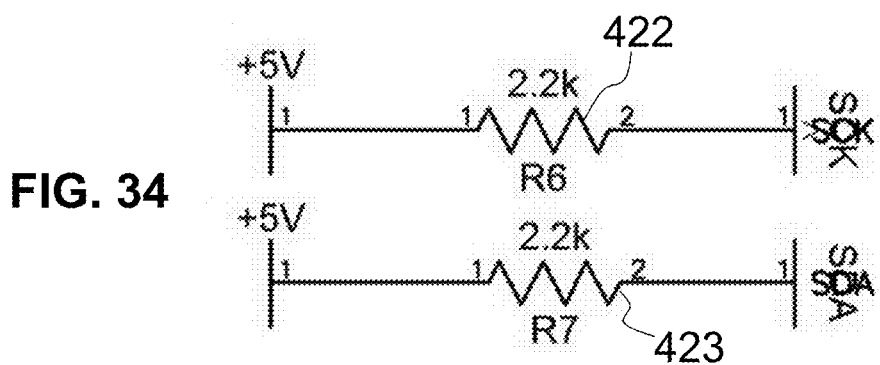
FIG. 34

THERMALLY CONTROLLED VARIABLE-FLEXIBILITY CATHETERS AND METHODS OF MANUFACTURING SAME

CROSS-REFERENCE TO RELATED APPLICATIONS

This application claims the priority, under 35 U.S.C. § 119, of U.S. Provisional Patent Application No. 62/483,736, filed Apr. 10, 2017, and U.S. Provisional Patent Application No. 62/644,797, filed Mar. 19, 2018; the prior applications are herewith incorporated by reference herein in their entirety.

STATEMENT REGARDING FEDERALLY SPONSORED RESEARCH OR DEVELOPMENT

Not Applicable

FIELD OF THE INVENTION

The present systems, apparatuses, and methods lie in the field of medical catheters. The present disclosure relates to thermally controlled, variable-flexibility catheters and methods of manufacturing such catheters.

BACKGROUND OF THE INVENTION

Catheters have many uses in modern medicine. One reason for their importance is their ability to guide and support additional instruments during a procedure at an anatomic location. In the procedure, a guide catheter is inserted between an entry site and advanced as far as is safe towards, for example, a lesion or a region of interest. Current catheters have smooth exteriors, nonetheless, the catheters can be held in place through friction with the walls in which the catheter is placed. As most anatomical conduits are not straight, friction provided to prevent movement of the catheter during a procedure occurs and increases with each bend that the catheter traverses. As one bend is traversed, one side of a vessel wall provides a friction point and as a second bend is thereafter traversed, a different side of the vessel wall provides a second friction point and so on for each bend. It is self-evident that the catheter must be flexible to traverse multiple bends but it still must retain its shape in order to be extended through a tortuous path. In comparison, catheters having a distal inflatable balloon find securement in an anatomical site by inflating the balloon to anchor between/within opposing walls, such as in a blood vessel. But, when so anchored, the catheter cannot move longitudinally without causing damage to the inflation site. Balloon catheters are problematic due to their total occlusion of blood flow in a given vessel during use and for the stress they place on vessel walls, but they are also unusable if the procedure requires multiple sets of extensions into anatomy and securement therein for each step.

Guide catheters are used as passageways to advance additional devices, such as smaller catheters or interventional devices such as stentrievers or embolic coils. Guide catheters simplify positioning of these smaller devices, allowing them to be easily advanced to the lesion or region of interest. Designers of current guide catheters face a trade-off between navigability and staying power. A more flexible catheter can be advanced through more complex anatomies, and can potentially be advanced closer to a lesion or region of interest. However, a more flexible catheter exerts less normal force on vessel walls for a given deformation of the catheter and, as such, is easier to back out from the region of interest due to lessened friction. Accordingly, it is not possible currently to improve navigability without worsening staying power and equally not possible to improve staying power without worsening navigability. It would, therefore, be desirable to overcome this and provide improvement in both staying power and navigability.

A significant issue encountered with guide catheters is "back-out", wherein pushing force applied to a catheter or implement within the guide catheter causes the guide catheter to move within the vasculature relative to its initial position. Because of the strain energy stored in a deformed guide catheter, these "back-outs" can be very sudden and dramatic events. Back-outs have adverse consequences with regard to patient safety and doctor success. When a guide catheter dislodges, it often brings with it the additional catheters or implements being used for a procedure, compromising what is often a complex set of device positions and placements through the patient's vasculature. This increases time in the operating room by necessitating re-catheterization of the patient. If a "back-out" event occurs during a critical moment in a procedure, for example, with deployment of a flow diverter, back-out can damage a device costing $10,000 or more and potentially cause severe harm to the patient. Accordingly, it would be desirable to provide a catheter that resists "back-out" and provides a reliable, stable guide.

The issues of support and back out are relevant in many fields, including interventional neurology and cardiology.

Another issue of relevance to catheters and catheter-based device users is ease of operation. Catheter operators desire a 1-to-1 operation—that is to say, a configuration that allows manipulations of a catheter's proximal shaft or hub to translate directly, consistently, and predictably to motion of the catheter's distal end, which includes both prismatic (insertion/retraction) motions and rotational motions. 1-to-1 operation cannot be perfectly ideal, in other words, with current materials, 1-to-1 operation is approximately or substantially 1-to-1 operation. Therefore, as used herein, the phrase 1-to-1 operation is defined to include a variance that one skilled in the art would know to be a reasonable tolerance. Guide catheters also help provide 1-to-1 operation to additional or secondary catheters and devices that do not have such distal end mobility. Devices constrained within the guide catheter's relatively stiff and smooth inner lumen are not able to buckle or push into compliant vessel walls. As such, guide catheters increase an operator's consistency, precision, and ultimately safety. It would be beneficial to provide a catheter that increases flexibility, increases retention force, and still provides 1-to-1 operation.

Thus, a need exists to overcome the problems with the prior art systems, designs, and processes as discussed above.

SUMMARY OF THE INVENTION

The systems, apparatuses, and methods described provide thermally controlled, variable-flexibility catheters and methods of manufacturing such catheters that overcome the hereinafore-mentioned disadvantages of the heretofore-known devices and methods of this general type and that provide such features with increased flexibility, increased retention force, and 1-to-1 operation. Such a catheter is referred herein as a variflex catheter.

The variflex catheter has one or more zones of user-controllable flexibility. The variflex catheter can be advanced through tortuous, complex anatomies in a soft, navigable state, and then be transitioned to a stiff state to increase retention force sufficient to resist back-outs and provide a reliable conduit for secondary devices, whether advanced in a central conduit or over the exterior. The variflex catheter offers the benefits of both rigid and floppy catheters, in essence performing the role of two catheters in one. Physicians and patients benefit from increased precision and safety, decreased operating room time, minimized risk of accidents, and lowered procedure costs.

Variable stiffness is achieved through a variable stiffness element that, in exemplary embodiments, is made up of a combination of a scaffold material and a binder, coupled with a method of heating the binder and, possibly, the scaffold material. Principally, the binder and/or scaffold is/are heated electrically. A temperature change of the variflex catheter can occur by heating the scaffold, the binder, or both, or through a separate heating device. One exemplary embodiment of a separate heating device is a separate device, such as a guidewire, with an electrical heating element; such a device can be manipulated inside the variflex catheter so that the heating section of the heated guidewire device is adjacent the variable-stiffness portion of the variflex catheter. Other exemplary methods of thermally-actuated changes in catheter flexibility include a variflex catheter that, at body temperature, is normally flexible, but when cooled (e.g., by introducing cool fluid into the catheter from its proximal end connection) assumes a less-flexible condition. The scaffold and binder are selected such that, when the scaffold and binder are at or below a given first temperature, they form a substantially rigid construct. When the scaffold and binder are above a given temperature, they form a relatively flexible construct. This flexibility transition is achieved, in exemplary embodiments, through partial or full, thermally induced phase change of the binder and/or scaffold, and how such change affects the scaffold's and/or binder's mechanical behavior(s). It is noted that changes in stiffness may not be instantaneous, because of the latent heat of fusion required to soften, for example, the stiffening binder. In an example, when wax is melted, its temperature rises to a phase-transition temperature (similar to melting) and then remains at that temperature until the bulk of the wax has undergone the phase change; once the phase transformation is complete, the temperature again rises with the application of additional heating. During the time between when melting begins and melting ends, there is a period of intermediate stiffness. This process may occur at different temperature depending on whether the process is undergoing increase in temperature (heating) or decrease in temperature (cooling). This difference in temperatures of phase transformation is referred to as hysteresis.

The variable stiffness element of the variflex catheter is controlled and regulated by a control system. The control system delivers regulated power to the electrical heaters within the variable stiffness element. In an exemplary embodiment with feedback, the control system regulates its power output based on information obtained from the variable stiffness element. One exemplary embodiment for obtaining feedback information employs sensors, such as thermocouples, within the variable stiffness element and, if desired, at other locations of the variflex catheter. The control system employs a control algorithm, such as a PID loop, to regulate its power output in response to sensor inputs, and, thus, precisely controls the temperatures and electrical conditions within the device's variable stiffness element. The control system responds to user inputs for stiffness change, and alerts users of device status through a combination of auditory, visual, and haptic feedback.

The variflex catheters find particular utility in the field of neurointerventional medicine. Neurointerventionalists frequently operate on the brain from an entry site situated on a patient's thigh (femoral access), and, as such, use relatively long catheters (e.g., lengths greater than 100 cm) for their procedures. Variable stiffness guide catheters as described herein enhance delivery of many therapies commonly provided by neurointervention, including aneurysm coiling, flow diversion procedures, aspiration of thrombi, delivery of embolic agents, and general diagnostics. While exemplary embodiments described herein may reference or relate to neurointerventional medicine, these embodiments are not limited thereto and are equally applicable to other areas of medicine, for example, vascular or cardiac procedures, digestive tract procedures, peripheral intervention procedures, and others where characteristics of a variable stiffness catheter are beneficial.

With the foregoing and other objects in view, there is provided, a catheter for use in a human body comprising a heater control system supplying power, a handle associated with the heater control system, a base catheter extending from the handle, defining an inner lumen, and comprising a proximal section connected to the handle and a distal segment, and a variable stiffness element. The variable stiffness element comprises a resistance heater conductively connected to the heater control system to receive power therefrom, extending distally from the heater control system, and coiled about the inner lumen at least at the distal segment, the resistance heater comprising a shaft portion of a first metallic conductive material at the proximal section and a heater portion of a second metallic conductive material at the distal segment, a hollow, outer jacket disposed at least about the heater portion, and a variable flex sub-assembly between the base catheter and the outer jacket and comprising a non-conducting braid and a binding material and, without power supplied to the heater when in the human body, the binding material is at a stiffened state, responsive to heating of the binding material by supplying power to the heater, the binding material changes to a softened state so that the variable flex sub-assembly has increased flexibility at least at the distal segment, and responsive to removing power supplied to the heater to thereby allow the binding material to cool, the binding material changes to the stiffened state so that the variable flex sub-assembly has decreased flexibility at least at the distal segment.

In accordance with another feature, the first metallic conductive material and the second metallic conductive material are the same.

In accordance with a further feature, the shaft portion of the first metallic conductive material and the heater portion of the second metallic conductive material comprise a continuous wire of the same metallic conductive material.

In accordance with an added feature, the shaft portion of the first metallic conductive material and the heater portion of the second metallic conductive material comprise an integral wire of the same metallic conductive material.

In accordance with an additional feature, at least the heater portion of the heater is coiled at the distal segment as a support structure sufficient to substantially prevent kinking and substantially maintain circularity of the base catheter at the distal segment.

In accordance with yet another feature, the given conductive material is one of copper, a copper alloy, and beryllium copper.

In accordance with yet a further feature, the heater has a given pitch at the shaft portion and a pitch at the distal segment less than the given pitch.

In accordance with yet an added feature, the given pitch is one of infinite and non-infinite.

In accordance with yet an additional feature, the given pitch is approximately 16.93 mm and the pitch at the distal segment is approximately 0.72644 mm.

In accordance with again another feature, the base catheter comprises a distal tip adjacent the distal segment and which further comprises a reinforcement coil at the distal tip.

In accordance with again a further feature, there is provided a temperature-sensing element at the distal segment communicating with the heater control system to supply a value of temperature at the temperature-sensing element to the heater control system, the heater control system configured to regulate the power supplied to the heater to control temperature of the distal segment based upon the value.

In accordance with again an added feature, the temperature-sensing element is a thermocouple junction independent from the heater.

In accordance with again an additional feature, the temperature-sensing element is a thermocouple junction in line with the heater.

In accordance with still another feature, the temperature-sensing element is a thermocouple junction integral with the heater.

In accordance with still a further feature, the outer jacket is disposed about the base catheter and extends proximally from the variable stiffness element along the inner lumen and adjacent the handle.

In accordance with still an added feature, the braid is a 32-carrier, 16 PIC, full-load, standard pattern tubular braid, each carrier being made up of 70 filaments of 22 Tex Dupont Kevlar.

In accordance with still an additional feature, the braid is braided support tube of a non-conductive para-aramid synthetic fiber.

In accordance with another feature, the binding material is a blend of microcrystalline wax and at least one of heneicosane, tricosane, docosane, eicosane, nonadecane, and octadecane.

In accordance with a further feature, the binding material is a blend of approximately 90% by mass of at least one of heneicosane and docosane and approximately 10% by mass of microcrystalline wax.

In accordance with an added feature, the heater control system heats the heater to a temperature above body temperature and, responsive to removing power supplied to the heater, the variable stiffness element cools to approximately body temperature.

In accordance with an additional feature, the heater control system heats the heater up to approximately up to 45° C.

In accordance with yet another feature, the heater control system is within the handle.

In accordance with a concomitant feature, the heater control system is separate from the handle.

Although the systems, apparatuses, and methods are illustrated and described herein as embodied in thermally controlled, variable-flexibility catheters and methods of manufacturing such catheters, it is, nevertheless, not intended to be limited to the details shown because various modifications and structural changes may be made therein without departing from the spirit of the invention and within the scope and range of equivalents of the claims. Additionally, well-known elements of exemplary embodiments will not be described in detail or will be omitted so as not to obscure the relevant details of the systems, apparatuses, and methods.

Additional advantages and other features characteristic of the systems, apparatuses, and methods will be set forth in the detailed description that follows and may be apparent from the detailed description or may be learned by practice of exemplary embodiments. Still other advantages of the systems, apparatuses, and methods may be realized by any of the instrumentalities, methods, or combinations particularly pointed out in the claims.

Other features that are considered as characteristic for the systems, apparatuses, and methods are set forth in the appended claims. As required, detailed embodiments of the systems, apparatuses, and methods are disclosed herein; however, it is to be understood that the disclosed embodiments are merely exemplary of the systems, apparatuses, and methods, which can be embodied in various forms. Therefore, specific structural and functional details disclosed herein are not to be interpreted as limiting, but merely as a basis for the claims and as a representative basis for teaching one of ordinary skill in the art to variously employ the systems, apparatuses, and methods in virtually any appropriately detailed structure. Further, the terms and phrases used herein are not intended to be limiting; but rather, to provide an understandable description of the systems, apparatuses, and methods. While the specification concludes with claims defining the systems, apparatuses, and methods of the invention that are regarded as novel, it is believed that the systems, apparatuses, and methods will be better understood from a consideration of the following description in conjunction with the drawing figures, in which like reference numerals are carried forward.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the systems, apparatuses, and methods. Advantages of embodiments of the systems, apparatuses, and methods will be apparent from the following detailed description of the exemplary embodiments thereof, which description should be considered in conjunction with the accompanying drawings in which:

FIG. 21 is an exploded, perspective view of an exemplary embodiment of a vacuum transfer device for a catheter;

FIG. 22 is a longitudinal cross-sectional view of the vacuum transfer device of FIG. 21 with a binder reservoir;

FIG. 23 is an enlarged, lateral cross-sectional view of the vacuum transfer device of FIG. 22 along section line XXVI with a catheter in a control volume;

FIG. 30 is a schematic circuit diagram of an exemplary embodiment of a power supply for the heater control system of FIG. 29;

FIG. 31 is a schematic circuit diagram of an exemplary embodiment of a power smoothing capacitor for the heater control system of FIG. 29;

FIG. 32 is a schematic circuit diagram of an exemplary embodiment of a voltage regulator for the heater control system of FIG. 29;

FIG. 33 is a schematic circuit diagram of an exemplary embodiment of a regulator smoothing capacitor for the heater control system of FIG. 29;

FIG. 34 is a schematic circuit diagram of an exemplary embodiment of voltage pullup resistors for the heater control system of FIG. 29;

DETAILED DESCRIPTION OF THE EMBODIMENTS

Figure 1:
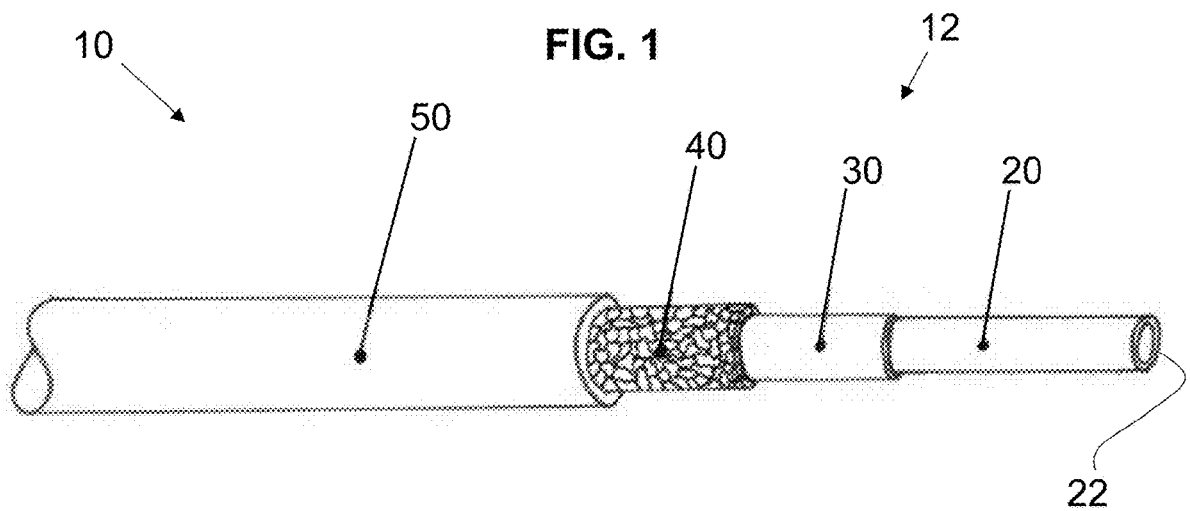
FIG. 1 is a fragmentary, perspective and partially cut away view of an exemplary embodiment of a variflex catheter.

As required, detailed embodiments of the systems, apparatuses, and methods are disclosed herein; however, it is to be understood that the disclosed embodiments are merely exemplary of the systems, apparatuses, and methods, which can be embodied in various forms. Therefore, specific structural and functional details disclosed herein are not to be interpreted as limiting, but merely as a basis for the claims and as a representative basis for teaching one skilled in the art to variously employ the systems, apparatuses, and methods in virtually any appropriately detailed structure. Further, the terms and phrases used herein are not intended to be limiting; but rather, to provide an understandable description of the systems, apparatuses, and methods. While the specification concludes with claims defining the features of the systems, apparatuses, and methods that are regarded as novel, it is believed that the systems, apparatuses, and methods will be better understood from a consideration of the following description in conjunction with the drawing figures, in which like reference numerals are carried forward.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Alternate embodiments may be devised without departing from the spirit or the scope of the invention. Additionally, well-known elements of exemplary embodiments of the systems, apparatuses, and methods will not be described in detail or will be omitted so as not to obscure the relevant details of the systems, apparatuses, and methods.

Before the systems, apparatuses, and methods are disclosed and described, it is to be understood that the terminology used herein is for the purpose of describing particular embodiments only and is not intended to be limiting. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element. The terms "including" and/or "having," as used herein, are defined as comprising (i.e., open language). The terms "a" or "an", as used herein, are defined as one or more than one. The term "plurality," as used herein, is defined as two or more than two. The term "another," as used herein, is defined as at least a second or more. The description may use the terms "embodiment" or "embodiments," which may each refer to one or more of the same or different embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact (e.g., directly coupled). However, "coupled" may also mean that two or more elements are not in direct contact with each other, but yet still cooperate or interact with each other (e.g., indirectly coupled).

For the purposes of the description, a phrase in the form "A/B" or in the form "A and/or B" or in the form "at least one of A and B" means (A), (B), or (A and B), where A and B are variables indicating a particular object or attribute. When used, this phrase is intended to and is hereby defined as a choice of A or B or both A and B, which is similar to the phrase "and/or". Where more than two variables are present in such a phrase, this phrase is hereby defined as including only one of the variables, any one of the variables, any combination of any of the variables, and all of the variables, for example, a phrase in the form "at least one of A, B, and C" means (A), (B), (C), (A and B), (A and C), (B and C), or (A, B and C).

Relational terms such as first and second, top and bottom, and the like may be used solely to distinguish one entity or action from another entity or action without necessarily requiring or implying any actual such relationship or order between such entities or actions. The description may use perspective-based descriptions such as up/down, back/front, top/bottom, and proximal/distal. Such descriptions are merely used to facilitate the discussion and are not intended to restrict the application of disclosed embodiments. Various operations may be described as multiple discrete operations in turn, in a manner that may be helpful in understanding embodiments; however, the order of description should not be construed to imply that these operations are order dependent.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. As used herein, the terms "substantial" and "substantially" means, when comparing various parts to one another, that the parts being compared are equal to or are so close enough in dimension that one skill in the art would consider the same. Substantial and substantially, as used herein, are not limited to a single dimension and specifically include a range of values for those parts being compared. The range of values, both above and below (e.g., "+/−" or greater/lesser or larger/smaller), includes a variance that one skilled in the art would know to be a reasonable tolerance for the parts mentioned.

It will be appreciated that embodiments of the systems, apparatuses, and methods described herein may be comprised of one or more conventional processors and unique stored program instructions that control the one or more processors to implement, in conjunction with certain non-processor circuits and other elements, some, most, or all of the functions of the devices and methods described herein. The non-processor circuits may include, but are not limited to, signal drivers, clock circuits, power source circuits, and user input and output elements. Alternatively, some or all functions could be implemented by a state machine that has no stored program instructions, or in one or more application specific integrated circuits (ASICs) or field-programmable gate arrays (FPGA), in which each function or some combinations of certain of the functions are implemented as custom logic. Of course, a combination of these approaches could also be used. Thus, methods and means for these functions have been described herein.

The terms "program," "software," "software application," and the like as used herein, are defined as a sequence of instructions designed for execution on a computer system or programmable device. A "program," "software," "application," "computer program," or "software application" may include a subroutine, a function, a procedure, an object method, an object implementation, an executable application, an applet, a servlet, a source code, an object code, any computer language logic, a shared library/dynamic load library and/or other sequence of instructions designed for execution on a computer system.

Herein various embodiments of the systems, apparatuses, and methods are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Described now are exemplary embodiments. Applicable to most of the exemplary embodiments described herein is what is referred to as a base catheter. A base catheter refers to a catheter sub-assembly on which variflex technology is added. The base catheter can be an entire catheter on which the variflex technology is added or the base catheter can be just one or more parts of the variflex catheter. Various combinations of mandrel, liner, reinforcement, material, and processing technologies can be successfully built upon with variflex catheter technology. The versatility of the variflex catheter technology allows its application to a wide variety of base catheter construction techniques, examples of which are described herein. The versatile nature of Variflex technology allows it to be applicable to a wide variety of catheter sizes and construction methodologies. The methods for constructing the variable stiffness elements described herein can be applied to catheter sizes ranging from micro-catheters (having an outer diameter of just a few tenths of millimeters) through large, guide or "shuttle" sized catheters (having an outer diameter of 3 mm). This versatility creates potential utility across various medical fields, for example, interventional neurology and cardiology.

Present in the base catheter is a flexible tube that, in most cases defines an interior hollow lumen through which fluids or other devices may extended. (In particular, embodiments where an internal passage is not required, the base catheter can be a flexible rod.) Ideally, the flexible tube provides a user with 1-to-1 operation, that is, when the user rotates, extends, or retracts the proximal end, the distal end moves correspondingly. Referring now to the figures of the drawings in detail and first, particularly to FIG. 1, there is shown a first exemplary embodiment of a distal tip 12 of a variflex catheter 10. The variflex catheter 10, in its simplest configuration, comprises an inner base catheter 20, an inner cylinder 30 surrounding the base catheter 20, a binder 40 surrounding the inner cylinder 30, and an outer cylinder 50 surrounding the binder 40. Together, the inner cylinder 30, the binder 40, and the outer cylinder 50 form a variable stiffness element or sub-assembly.

In general, the variable stiffness element provides varying degrees of flexibility, from substantially flexible to substantially stiff. The reinforcement provided by the variable stiffness element occurs by changing the stiffness characteristics of the binder. When the binder is relatively soft, the variable stiffness element permits high flexibility. When the binder is relatively hard, the variable stiffness element prevents flexibility. As used here, "relatively" means that one of the characteristics is being compared to the other characteristic, in other words, one relative to the other, such as the characteristic of flexibility being hard and soft. Hard, when used herein to describe an attribute, is being compared to the other attribute "soft" and to say that some feature is relatively hard means that it is harder in comparison to that feature when it is soft. Thus, when each contains the word "relatively," this means that the two attributes are being compared to one another and identify different states of that attribute. Contained within the binder 40, the outer cylinder 50, and/or the inner cylinder 30 (which can also be the inner base catheter 20) is a device that changes stiffness of the binder 40. This device can be a conductor, a heater, both a conductor and a heater, or it can be a separate part in addition to the binder 40, the outer cylinder 50, and the inner cylinder 30. As will be described in further detail below, the conductor/heater can be wrapped or placed about the inner base catheter 20, it can be a flex circuit containing wires, conductive polymers, and/or foils, and it can be formed into the shaft reinforcement, in other words, part of a braid or coil structure.

A primary function of the variflex catheter 10 is the ability to change its stiffness characteristics. In other words, the variflex catheter 10 is able to be inserted within an anatomic orifice (such as a blood vessel) in a navigable state in which the variflex catheter 10 has flexibility sufficient to provide the greatest ability to navigate tortuous anatomy while providing the desirable 1-to-1 operative control and, after positioning the distal tip 12 or an intermediate portion of the variflex catheter 10 at a desired anatomic site (as will be described below, the variflex technology described herein is not limited to the distal tip and can be provided at an intermediate location of the catheter, either instead of or in addition to, providing variflex technology at the distal tip), the variflex technology transforms the catheter to prevent flexibility (i.e., to stiffen) and, thereby, provide the greatest ability to remain where it is currently placed (i.e., staying power). In this latter, stiffened state, the variflex catheter 10 permits the user to perform medical procedures at a desired anatomical site. For example, where the variflex catheter 10 is used in an interventional neurological procedure, the variflex catheter 10 is extended through vessel anatomy (e.g., from the groin) while in the flexible state through the body and into a vessel inside the skull. If a stent is to be implanted in a cranial vessel, for example, when the distal tip 12 is adjacent the implantation site, the variflex catheter 10 is set into its stiff state, thereby locking the length of the variflex catheter 10 within the anatomy and substantially preventing rotation, extension, or retraction of the distal tip 12 from its current state. In this exemplary embodiment, an active section of variflex catheter 10—for example, the longitudinal section containing the variflex technology can be the distal half or distal third of the longitudinal extent, or it can be just a few centimeters in length.

The variable stiffness element comprises a scaffold, a binding material associated with the scaffold, and a heat-transition device (for example, a heater) associated with either or both of the scaffold and the binding material so that heat generated causes either or both of the binding material and the scaffold to change its/their flexibility characteristics.

One exemplary embodiment of the scaffold, and for constructing the scaffold, provides a tubular braid having a hollow core, comprising multiple carriers of one or several materials braided into a tubular structure. The carriers of the braid are free to slide relative to one another when the braid structure is subjected to bending. Addition of the binding material to the braid modifies the braid's bending behavior. For example, the binding material can be waxy compound spread evenly over, under, and through the braid and held together therebetween on the outer side (by the outer cylinder 50) and on the inner side (by both the inner base catheter 20 and the inner cylinder 30, in a two-part configuration, or by only the inner base catheter 20 when the inner cylinder 30 is the inner base catheter 20 as a one-part configuration). The binding material, when in a softened navigable state, permits the carriers of the braid to slide easily relative to each other when subjected to loads and, when the binding material is in the stiffened state, the binding material inhibits the carriers of the braid from sliding relative to each other when subjected to loads. In the stiffened state, therefore, the braid and binder form a stiff composite monocoque. Upon transition back to the softened state, the binding material reduces its hold on the carries of the braid, allowing for easier relative motion and, thus, increased flexibility.

The braid carriers can be of any material that can be braided. The material should not be so stiff as to inhibit the flexible navigable state of the variable stiffness element and should be able to mechanically engage with a chosen binding material. One exemplary embodiment of a braid carrier is a multifilament Kevlar® tow. This exemplary embodiment of the braid is woven out of thirty-two (32) carriers in a full-load, standard pattern, where each carrier comprises seventy (70) 0.017 mm diameter filaments. More generally, the braid comprises between 8 and 64 carriers. The carriers can all have the same diameter and be between approximately 0.08 mm and approximately 0.15 mm. Alternatively, the carriers can have different diameters ranging between approximately 0.01 mm and approximately 0.2 mm. In an exemplary embodiment, the braid is made up of multifilament tows that are made from a number of filaments, for example, 70. The fibrous nature of the multifilament tows provides ample absorption of binding material, as well as substantial bonding surface area. Examples of other braid materials include, but are not limited to, carbon fiber, Polyethylene Terephthalate (PET), stainless steel, UHMW polyethylene, and fiberglass.

Figure 2:
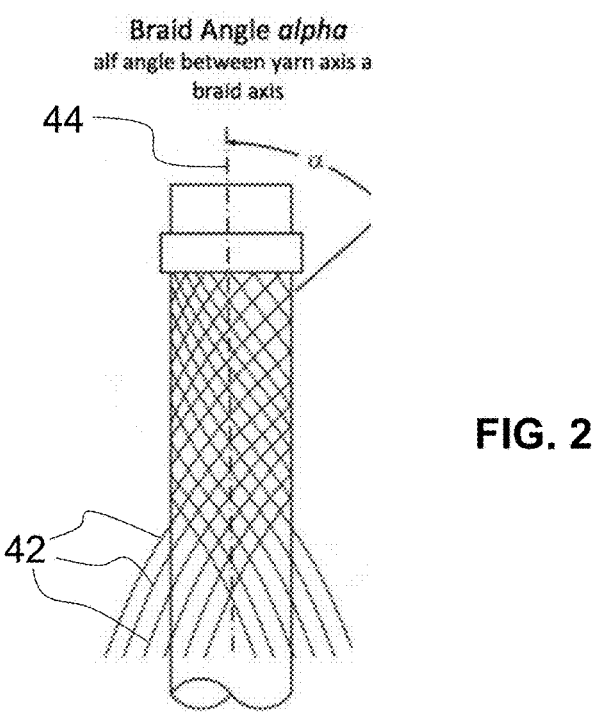
FIG. 2 is a fragmentary, elevational view of an exemplary embodiment of a braiding structure for a variflex catheter.

By controlling the dimensional characteristics of a braid-based scaffold, the properties of a given variable stiffness element can be manipulated. A braid's Per Inch Crosses (PIC) describes the number of crossings the braid's carriers make relative to each other within an inch of braid. This number thus implies an angle $\alpha$ that the braid's carriers 42 form relative to the braid's central axis 44. An illustration of braid angle $\alpha$ is found in FIG. 2. The lower the braid's PIC count and braid angle, the more resistant the given braid will be to bending. A braid with an infinitely low PIC count, therefore, subjects some of its carriers to pure tensile loadings upon flexure, whereas a braid with an infinitely high PIC count subjects its carriers to dominantly torsional loading.

Figure 3:
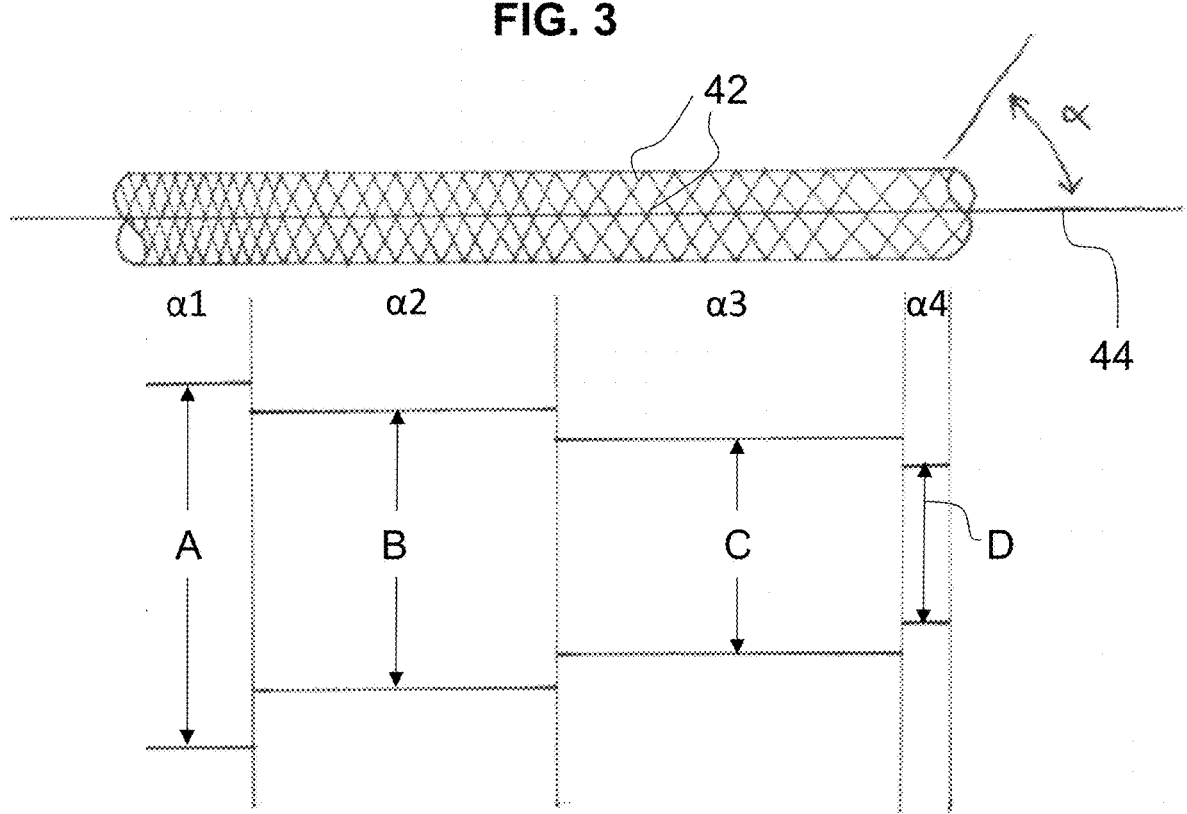
FIG. 3 is a fragmentary, elevational view of another exemplary embodiment of a braiding structure for a variflex catheter having sections with different flexibility.

An exemplary method for adjusting the stiffness of a given braid-based variable stiffness element is performed by adjusting the entire braid's PIC count; the higher the PIC count, the stiffer the braid and the lower the PIC count, the more flexible the braid. Furthermore, it is possible to vary the PIC count along the length of a given braid, which is depicted in FIG. 3, yielding a stiffness element with designer-specified, varying maximum stiffness along its length. In the illustration of varying PIC count in FIG. 3, there are four different PIC count sections. $\alpha 1$ has the highest PIC count, $\alpha 2$ has a smaller PIC count than $\alpha 1$, $\alpha 3$ has a smaller PIC count than $\alpha 2$, and $\alpha 4$ has the smallest PIC count. Therefore, the relative stiffness decreases from $\alpha 1$ to $\alpha 4$, as depicted by the diagram below the braid indicated with capital letters, the relative stiffness being defined by the formula A>B>C>D. This allows for adjustments to the variable stiffness element's overall stiffness properties, enabling fine-tuning for anatomical demands or to meet product specifications.

In an alternative embodiment to a scaffold configuration, two or more surfaces are oriented concentrically to each other and the catheter and these surfaces are sized so that they are free to slide relative to one another when the catheter is flexed and when no binder is present. These two or more surfaces are configured to substantially mechanically engage with the binding material when placed therebetween. These surfaces can be made up of tubular elements or can be formed by the placement of non-tubular shapes of material.

In one exemplary configuration, the tubular elements are, at an inner extent, disposed on the exterior surface of the base catheter 20 (e.g., the inner cylinder 30), and can be, at an outer extent, an outer jacket (such as the outer cylinder 50) made of an appropriate material and/or etched or otherwise surface treated to mechanically engage with the chosen binder in a cooled and stiffened state when the binder 40 is disposed (for example, sandwiched) between the two cylinders 30, 50. An example of this construction, with two concentric cylinders and a binder therebetween is shown in FIG. 1. Other exemplary embodiments of the variable stiffness element with scaffolding has a configuration that is described with reference to FIG. 4. In a first variation, two ribbons 31, 51 (e.g., of expanded PTFE) are wrapped around a centrally disposed base catheter 20 with opposite wrap directions. The ribbons 31, 51 are saturated with a binding material. The two ribbons 31, 51 thereby form two concentric tubular elements that rigidly lock relative to each other when the binding material is in the stiff state but slide relative to each other, and thus allow flexion, when the binder is in the softened navigable state. In a second variation, the binder 41 is disposed between the ribbons 31, 51. The two ribbons 31, 51 (e.g., of expanded PTFE) are wrapped around a centrally disposed base catheter 20 with opposite wrap directions. Between the ribbons 31, 51 is a layer of binding material 41. Accordingly, the two ribbons 31, 51 and the binding material 41 form a sandwich of two concentric tubular elements with binder therebetween. These two tubular elements rigidly lock relative to each other when the binder is in a rigid state and slide relative to each other, and thus allow flexion, when the binder is in the softened navigable state.

Figure 5:
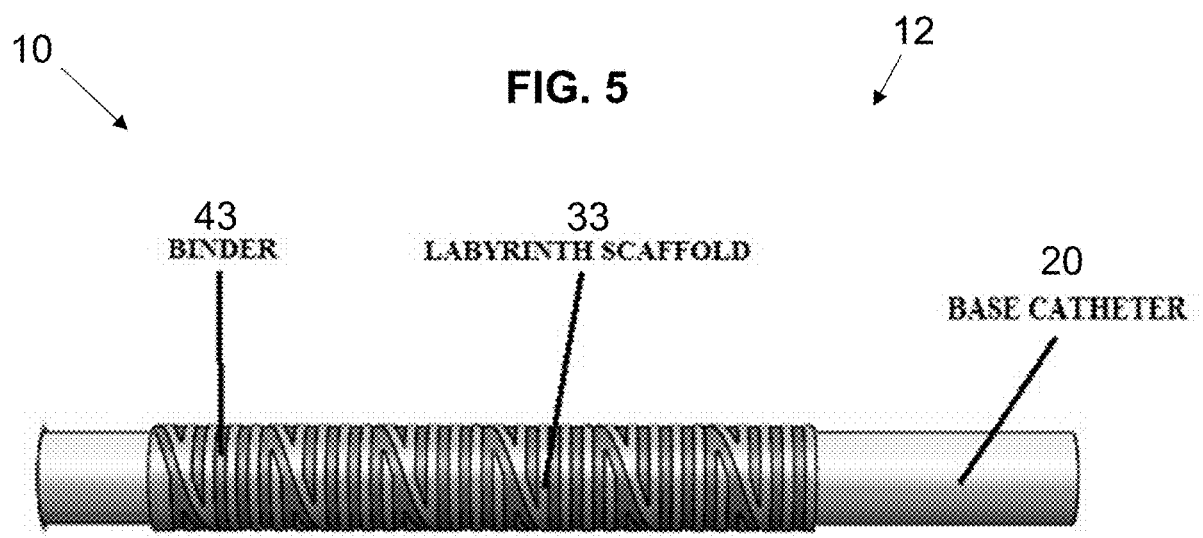
FIG. 5 is a fragmentary, elevational view of an exemplary embodiment of a support structure for a variable stiffness element of a variflex catheter having labyrinthine sections for binding material in an unflexed state and with exterior elements removed for clarity.
Figure 6:
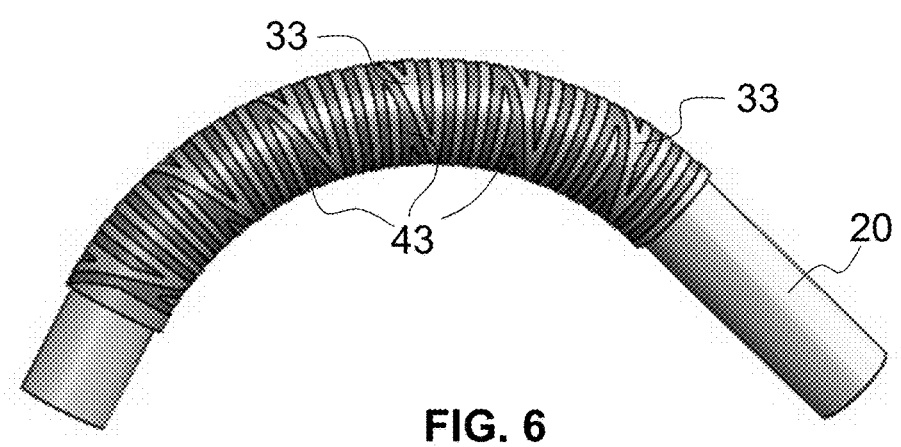
FIG. 6 is a fragmentary, elevational view of the support structure of FIG. 5 in a flexed orientation.

Still a further exemplary embodiment for constructing a scaffold is shown in FIGS. 5 and 6. A labyrinth scaffold 33 is sandwiched between an outer cylinder and an inner cylinder but FIGS. 5 and 6 only show the inner cylinder for reasons of clarity and, in this embodiment, the inner cylinder is the base catheter 20 itself (alternatively, the inner cylinder 30 can be disposed between the base catheter 20 and the labyrinth scaffold 33). The labyrinth scaffold 33 has a structure that forms (between adjacent spans, curves, spars, etc.) a labyrinth of voids in which is disposed the binding material 43. The voids are shaped to communicate with one another so that when the variable stiffness element is flexed while the binder is maintained in the softened flexible state, the binder is free to re-distribute itself throughout the labyrinth voids, which are now redefined by the labyrinth's altered geometry under flexion. If the binder is transitioned to the stiffened state while occupying this altered geometrical distribution, it substantially stiffens the entire variable stiffness element through resistance to forced cold flow. This variable stiffness element is shown in FIG. 5 in an un-flexed state and in FIG. 6 in a flexed state.

Another possible alternative configuration of the scaffold is a collection of independent rigid pieces in a matrix. The pieces can have any geometric shapes including, but not limited to, snowflakes, powders, or particles, and can also comprise MEMS (micro electro mechanical sensor) elements.

Other exemplary embodiments of the outer jacket reinforce and support the variable stiffness element (i.e., variflex portion) of the catheter while encapsulating and separating the binder and inner cylinder from contact with a patient. One exemplary configuration is an outer jacket made of thin layers of polymers, such as Pebax. Such a configuration is very flexible but it is vulnerable to invagination from drag during insertion or removal and tearing at the sealed ends. One way to remedy this issue is to place a reinforcement structure, such as a wire coil, within or over top of the outer jacket at the variable stiffness element. An exemplary embodiment for constructing the reinforcement structure as a coil is a Nitinol coil, which can be either heat-set or wound in place. Other metals for the coil also satisfy the reinforcement requirement and include, for example, stainless steel and platinum-iridium alloy. Furthermore, non-metallic reinforcements, such as PEEK or Kevlar®, are likewise available for use as a reinforcement coil, which coil can be either heat-set or wound in place. An exemplary embodiment of the reinforcement structure is a helical coil, wound from round 304V stainless steel wire with a diameter of approximately 0.001" (0.0254 mm), and a pitch of approximately 0.01" (0.254 mm).

A first exemplary method for encapsulating such a support coil is referred to as a Jacket-Coil-Dip process. First, the coil is wound over an existing outer jacket, such as those herein-described embodiments. An encapsulant is then deposited around and over the coil, which encapsulant attaches the coil to the underlying jacket and prevents the coil from dislocating or migrating. Encapsulants can be dip-coated, sprayed, brushed, spun, electrospun, sputtered, etc., onto the coil and the outer jacket. The encapsulant can cure by temperature, moisture, chemical reaction, ultraviolet light, and/or evaporation. Exemplary materials for the encapsulants include water-dispersed polyurethane with a cross-linker and solvent-cast thermoplastic polyurethane (TPU). Another exemplary method for encapsulating the support coil is referred to as a Dip-Coil-Dip process. This is similar to the Jacket-Coil-Dip process, but, in this embodiment, the outer jacket is also manufactured by dipping, spraying, brushing, etc., instead of being made with an existing extrusion. Instead of adding an outer jacket extrusion over the binder, then placing the coil around the extrusion, and then coating the coil with the encapsulant, the binder is coated for a first time with the encapsulant material, the coil is installed onto the outer surface of the encapsulant, and then the coil and the first encapsulant material is coated, for a second (or more) time, with the encapsulant material."

Figure 19:
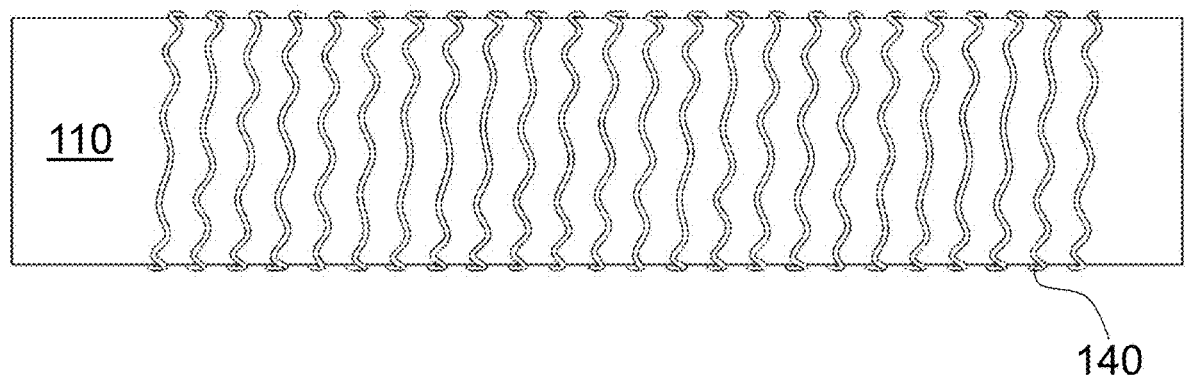
FIG. 19 is a fragmentary, enlarged, side elevational view of an exemplary embodiment of a diagrammatic illustration of inner liner surrounded by a reinforcement coil having a secondary deformation pattern.
Figure 20:
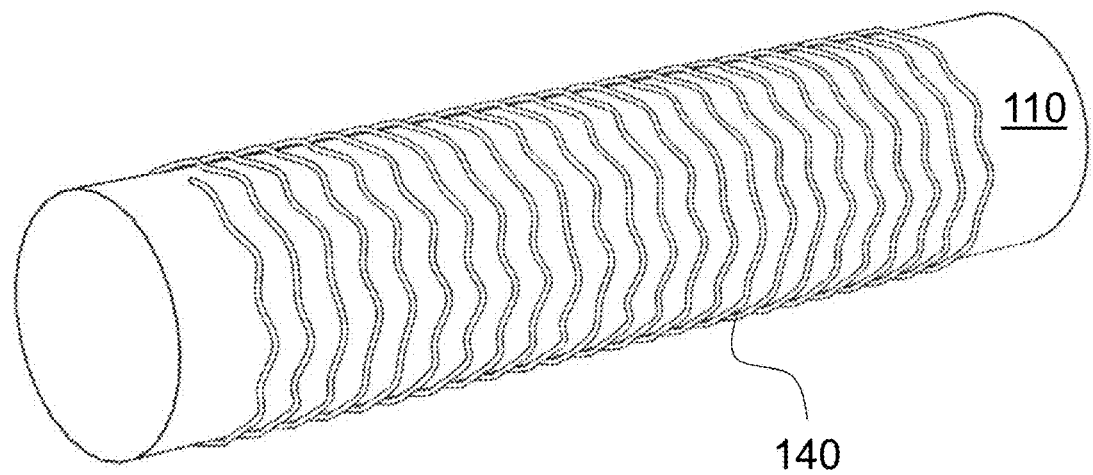
FIG. 20 is a fragmentary, enlarged, perspective view of the inner liner and reinforcement coil of FIG. 19.
Figure 24:
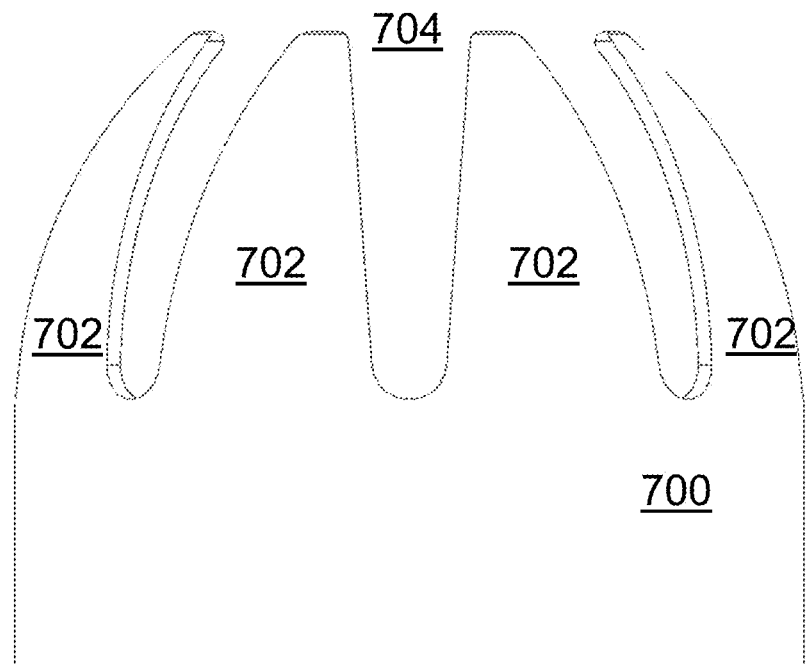
FIG. 24 is an enlarged, fragmentary, elevational view of an exemplary embodiment of a catheter tip.
Figure 25:
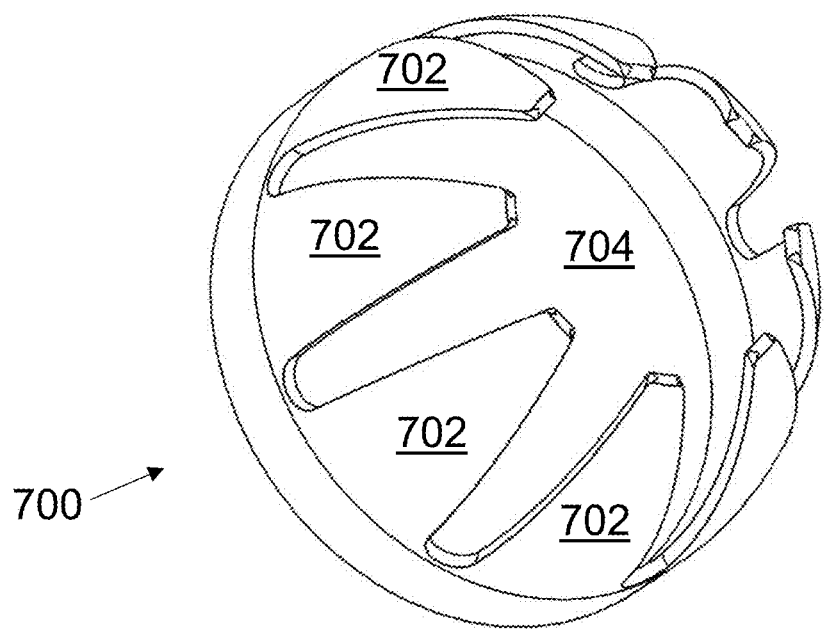
FIG. 25 is an enlarged, perspective view of the catheter tip of FIG. 24.
Figure 26:
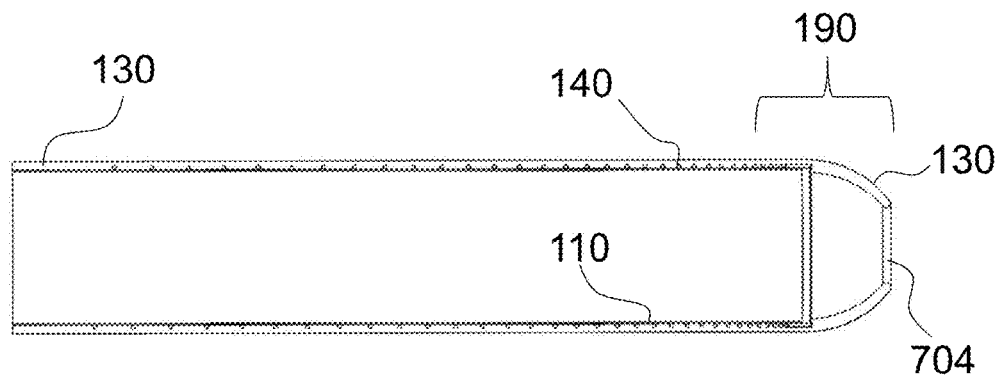
FIG. 26 is a fragmentary, cross-sectional view of the catheter tip of FIG. 24 encapsulated and installed on a distal end of a variflex catheter having a support coil.
Figure 27:
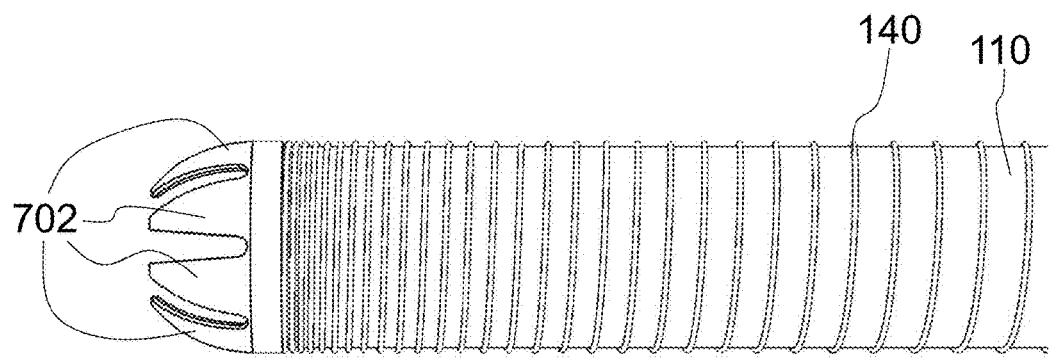
FIG. 27 is a fragmentary, elevational view of the catheter tip of FIG. 24 installed on a distal end of an inner cylinder of a variflex catheter having a support coil.
Figure 28:
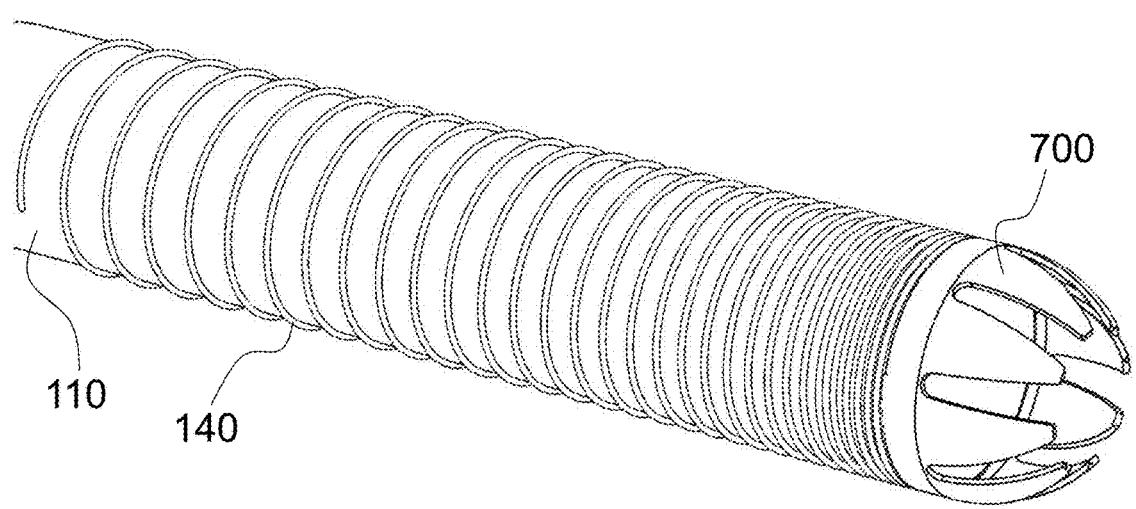
FIG. 28 is a fragmentary, perspective view of the catheter tip and variflex catheter of FIG. 27.
Figure 29:
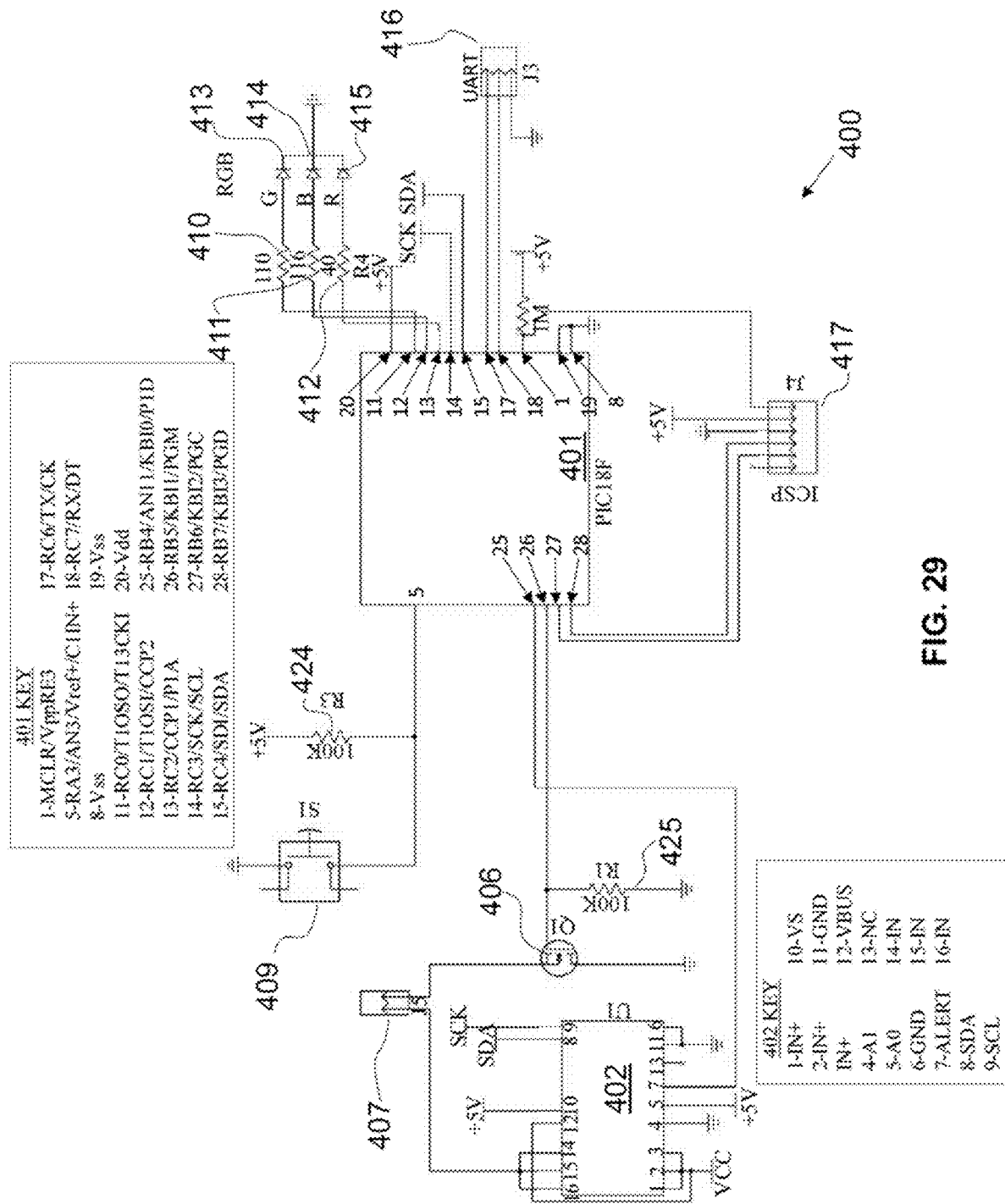
FIG. 29 is a schematic circuit diagram of primary components of an exemplary embodiment of a heater control system for the variflex catheter.

One disadvantage to reinforcing the outer jacket (such as the outer cylinder 50 or cover 130) with a helical coil is that the helical coil restricts radial expansion of the outer jacket. This is problematic in situations where the chosen binder for the variable stiffness element undergoes significant volumetric expansion during melting. The resulting pressure can cause undesirable herniation of the outer jacket between wraps of the reinforcement coil. To eliminate this effect, an exemplary embodiment of a helical reinforcement or support coil 140, illustrated in FIGS. 19 and 20, provided with a secondary crimp or deformation pattern, which decreases the reinforcement coil's resistance to radial expansion and is referred to herein as a wiggle wire. A reinforcement coil 140 wound from wiggle wire has a primary shape that is helical and exhibits a secondary crimp or deformation pattern on a fine scale. In an example where the fine pattern of the reinforcement coil 140 is sinusoidal, a pattern of repeated sinusoidal bends expands more readily than a helical coil of the same primary dimensions. The wire of a reinforcement coil 140 configured as wiggle wire deforms dominantly in a bending mode, as opposed to through tensile elongation, to permit radial expansion of the coil 140. The energy input required to expand a reinforcement coil 140 of wiggle wire of a given starting dimensions through a given radial deformation is notably less than that required to impart the same expansion on a helical coil of the same starting dimensions. The same materials relevant to helical outer reinforcement coils are also applicable to wiggle wire. The wiggle wire coil is compatible with the various jacketing techniques mentioned herein, for example, Jacket-Coil-Dip and Dip-Coil-Dip.

The binding material for a variable stiffness element is selected with consideration to its thermal and mechanical properties within a precise set of temperature ranges. One ideal embodiment of the binder is solid at human body temperature and melts sharply at a temperature slightly above human body temperature, in this regard, therefore, imparting a small amount of heat to the binding material causes it to change phase from a solid to a liquid. Another exemplary binder is liquid at human body temperature and hardens at a temperature slightly below human body temperature. In such an exemplary embodiment, the catheter is based on cold fluid stiffening and a cold fluid is circulated to the variflex section to impart the temperature reduction for binder hardening. Cold-fluid stiffening is discussed in further detail below. Furthermore, an ideal binding material adheres or wets to a chosen scaffold material and possesses adequate mechanical toughness in a solid state to resist brittle failures.

One exemplary embodiment of the binding material, and for constructing the binding material, comprises a mixture of 90% mass of heneicosane and/or docosane, (a discrete molecular compound in the paraffin family) and 10% mass microcrystalline wax. For example, heneicosane melts abruptly at approximately 42° C., but is brittle. The addition of microcrystalline wax lends toughness to the solidified mixture and slightly broadens the mixture's melting point. This mixture adheres readily to a variety of braid materials, is solid at body temperature, and readily melts in a narrow temperature window above 42° C. but below approximately 43.3° C. Exemplary alternatives to the microcrystalline wax include, but are not limited to low molecular weight (LMW) polyethylene with various plasticizers, and non-Newtonian fluids. The choice of wax used and the corresponding melt temperature takes into consideration CEM-43C thermal exposure guidelines, which are based on industry-accepted thermal tissue damage models. The CEM-43C model has been around for decades and calculates safety of a given thermal exposure to tissue by converting it to Cumulative Equivalent Minutes at 43° C. The effects of tissue exposure to 43° C. temperatures are well understood across a wide gamut of time ranges, and the CEM-43C model maps exposure to other temperatures for given amounts of time into equivalent exposure times to 43° C. temperatures, allowing comparison to known safety figures. Standard allowable CEM-43C exposures are in excess of ten minutes equivalent time. The exemplary embodiment of the binding material described above, which is a mixture of 90% mass heneicosane and/or docosane and 10% mass microcrystalline wax, melts at a temperature below 43° C. As such, the variflex catheter can be left in a heated state at 43° C. for many consecutive minutes, far longer than is needed in a procedure to reach a desired position while heated and then stiffen the device when cooled. Other exemplary embodiments of the binding material include tricosane, docosane, eicosane, nonadecane, and octadecane.

An exemplary embodiment of a method for preventing localized overheating of the binder beyond its melting temperature involves adding a secondary compound to the binding material, the secondary compound having a melting temperature slightly higher than that of the main binder and absorbing excess thermal energy while preventing bulk temperature rise by virtue of its latent enthalpy of fusion. In a situation where only a primary binder exists in a liquid phase, at or above its melting temperature, and more heat is added to the binder, the binder's temperature will continue to rise. Alternatively, if the bulk of the primary binder exists in a liquid phase at or above its melting temperature, but a second phase is present within the binder that remains solid or partially un-melted, additional heat added to the binder will not raise the mixture's bulk temperature so long as the second phase is not fully melted. This provides a buffer against accidental overheating. This desired characteristic of a two-phase mixture of immiscible materials is further explained with regard to the graph of FIG. 7.

Figure 7:
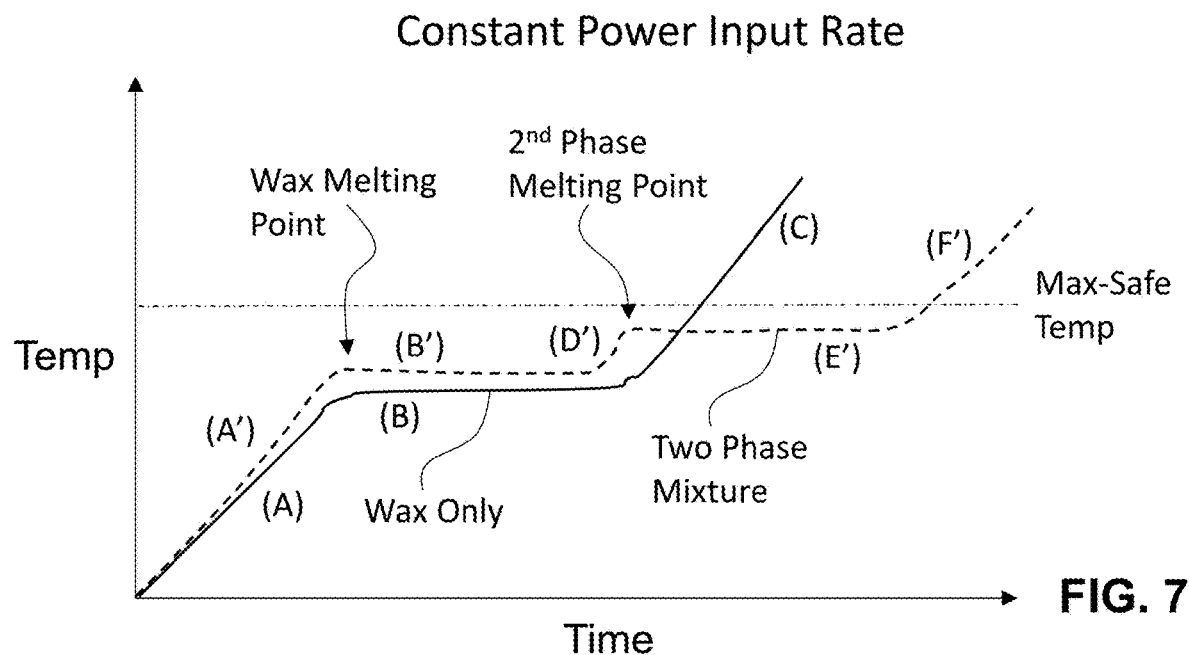
FIG. 7 is a graph of temperature versus time for an exemplary embodiment of a two-phase heat transfer materials for the variflex catheter.

As shown on the solid line of the graph of FIG. 7, as heat is added to solid wax, the temperature rises (A) until the wax's melting point is reached. Then, the temperature plateaus (B) as the wax is melted. Once the entire volume of solid wax has been melted, the temperature of the melt rises (C) as additional heat is added. For the binding material of the variable-stiffness catheter herein, the final increase in temperature after melting is completed may present a hazard to tissue that is contacted by the catheter because it is higher than the maximum-safe temperature for the tissue against/in which the catheter is place. For example, if the variflex catheter is intended to be used in blood vessels, it is known that endothelial tissue cells on the interior wall of an artery may be damaged when they are exposed to over 50° C. Therefore, in a particularly advantageous embodiment, heating of the variflex catheter limits the maximum-safe temperature rise of the catheter to a temperature less than 45° C.

The cause of the plateau temperature of melting wax, as shown in FIG. 7, is the "heat of fusion" of the wax, which is the additional heat that must be added to solid wax that has been raised to its melting temperature before any of the wax can change from the solid phase to the liquid phase. Virtually all solid materials have this characteristic heat of fusion. The inventors discovered that it would be advantageous to add a second material having a melting temperature above that of the wax but below the maximum-safe temperature and having a substantial heat of fusion. With such a configuration, when the two-phase mixture is melted, the resulting thermal characteristics are indicated by the dashed line in FIG. 7. In particular, as heat is added, the temperature rises (A') and reaches a plateau (B') at the melting point of the wax. That temperature then remains substantially constant until the entire wax component has been melted, and then the temperature of the mixture begins to rise once again (D'). Once the melting temperature of the second phase material is reached, a second temperature plateau (E') occurs and lasts until all of the second phase material has been melted. Once both materials are in the liquid phase, the temperature again begins to rise (F'). But, as can be seen in FIG. 7, the time between first melt of the wax and final melt of the second phase material is much greater than the time between first melt of the wax and final melt of the wax, which is the desired characteristics for a binding material that is substantially solid at body temperature and is substantially liquid at the maximum-safe temperature, e.g., at 45° C.

In order for the mixture to have the described thermal characteristics, the two material phases (the wax and the second-phase material) would have to remain discrete, so that a single combined phase would not appear; a mixture such as this is a "solution" and would have either a continuous range of melting temperatures, an intermediate melting temperature, a melting temperature lower than that of either phase (a eutectic mixture), or a melting temperature higher than that of either material (a peritectic mixture). So, in order to create a mixture with two distinct plateaus during the melting process, the two phases remain immiscible as liquids and neither material, when solid, dissolves in the liquid of the other. An exemplary embodiment of such a mixture is water and wax. At a low temperature, both materials are solid (solid wax and water ice). As the temperature is raised, the ice begins to melt at 0° C. and the temperature of the mixture remains constant until all the ice is melted. Once the water is melted, the temperature of the two materials increases until the melting point of the wax is reached, at which point the temperature remains substantially constant at the melting temperature of the wax until all the wax is melted. Once both water and wax are in liquid form, the temperature of the mixture would, once again, begin to rise as additional heat is added.

To be useful for the variflex catheter, which uses a precisely formulated wax that melts at slightly above human body temperature, the second-phase material has a number of discrete characteristics. First, the second-phase material has a melting temperature below the maximum-safe temperature and it has a substantial heat of fusion. More specifically, the second-phase material desirably melts in a range of approximately 40° C. to approximately 45° C. and, in particular, between approximately 42° C. and approximately 44° C. Second, the second-phase material desirably is non-toxic because, if any of the second-phase material were accidentally released into the bloodstream because of a failure of the catheter, there would be no cellular or systemic reaction. Although the second-phase material is contained within a sealed portion of the variflex catheter, it is desirable that, even if the material were released because of a breach of the catheter jacket, there would be no toxicity to the interior wall of the artery, to blood, or to other body areas to which the blood might flow. Finally, the second-phase material is insoluble and immiscible in the wax phase, even when repeatedly melted and solidified. In other words, the second-phase material is insoluble in wax when it is a solid and immiscible in molten wax when it is a liquid.

There are other characteristics related to stability of the second-phase material. In addition to being insoluble and immiscible in the liquid and solid wax phases, the second-phase material is capable of being finely divided in both solid and liquid form. The two-phase mixture may be made by reducing the solid form of the second-phase material to a powder and mixing it with wax (the wax may be in either molten or in powdered form). Once dispersed in solid or molten wax, the dispersed particles of the second-phase material must remain separate and not agglomerate or coalesce into larger particles. Once a temperature has been reached beyond the second plateau (E'), where both the wax and the second-phase material are in liquid states, the fluid mixture is in the form of an emulsion or colloid (depending upon the size of the dispersed phase and its stability). The tendency of the second-phase liquid droplets to coalesce into larger droplets must be impeded in order for the emulsion to remain stable. Both agglomeration of solid-phase powder particles and coalescence of liquid-phase droplets can be impeded by the use of surfactants and other forms of anti-coagulants (polymeric stabilization, electrostatic stabilization, micro-encapsulation) as is known in the art.

Further, because the mixture may be required to be stored for long periods before use, how the second-phase material deals with moisture during storage is another characteristic to consider. When looking at possibilities, some candidates for the second-phase material are hygroscopic; that is, they absorb water when exposed to the atmosphere. Absorption of water changes the solidification/melting properties of some materials, so a second-phase material should be chosen that does not have its melting properties appreciably changed when the product is exposed to air. While encapsulation of the second-phase material by the wax phase helps to prevent water absorption, long-term storage may be a problem with second-phase materials that are hygroscopic. For example, choline chloride is very hygroscopic. Although mixtures of choline chloride and other materials (e.g., water, urea, ethylurea, methylurea, malonic acid, and heavy-metal halide salts) can be made that melt in the desired range, these mixtures have melting points that change when water is absorbed from the atmosphere, thereby limiting their use as a candidate for the second-phase material.

Ionic fluids have been developed for industrial solvent and electrolyte processing and are often referred to as "green solvents" because of their low rate of evaporation and low toxicity. Ionic fluids comprise a mix of organic and inorganic anions and cations that are liquid at or near room temperature (rather than solid, as are most inorganic ionic compounds). In addition, mixtures of organic solid ionic compounds and (organic or inorganic) solid solutes sometimes form eutectic mixtures with melting points at or below room temperature. One family of such eutectic mixtures comprises choline chloride and a solid solute from the group of any one or more of:
 heavy-metal halides (e.g.: zinc chloride);
 fatty acids (e.g.: malonic acid);
 sugars and saccharides (e.g.: dextrose); and
 urea compounds (e.g.: ethylurea).
Of these, the heavy-metal halides are not useful as the second-phase material because of their toxicity.

The inventors have studied many common mixtures (referred to in the literature as "deep eutectic solvents" (DES)), but none have a melting point at the desired range of 40°–45° C. However, it was found that choline chloride, a low-toxicity material, has a melting point that changes with the addition of very small amounts of water, and it was found that choline chloride containing approximately 5% by weight of water has a melting point in the range 40°–45° C. Choline chloride hydrated to this extent is insoluble in wax, in both its molten or solid form. So, it can be used as the second-phase material of the variable stiffness element. However, it was found that, because of the large change in melting point as a function of level of hydration, the resulting mixture is not stable when exposed to air. As a result, after a few days of exposure, the choline chloride absorbs sufficient moisture from the atmosphere to have a melting point well below room temperature. Nonetheless, mixtures of hydrated choline chloride did illustrate that the use of a second-phase material with a melting point in the range 40°–45° C. does in fact form the two-plateau melting behavior as explained herein, but a more stable second-phase material is desired.

The inventors noted that inorganic salts exist that have melting points in the range desired. Cordaro, et al., reported in "Thermodynamic Properties of Molten Nitrate Salts" that calcium nitrate [$Ca(NO_3)_2 \cdot 4H_2O$] melts at 38°–44° C. In addition, there are other hydrated nitrate salts with melting points in this range, but, if used, the pharmacologic properties (e.g., vasodilation) of water-soluble nitrates properties would have to be taken into account as a risk factor. As a general rule, inorganic salts with low melting points can include, but are not limited to, hydrated salts, nitrates, and heavy-metal cations. However, none of these salts is ideal for the second-phase material.

Organic compounds that are non-toxic tend to be simple carbon-hydrogen compounds, such as alkanes (saturated carbon-hydrogen compounds), alkenes (unsaturated carbon-hydrogen compounds), sugars, proteins, and alcohols. Other organic forms, such as aldehydes, ketones, esters, carboxylic acids, aromatics, ethers, amines, amides, etc., are generally toxic. Proteins have complex structures and do not generally have discrete crystallization (melting) temperatures. No sugars have the desired melting points, and even known eutectic and tritectic mixtures of sugars all have melting points above 60° C. Pure alkanes and alkenes are soluble in molten wax, so they are not suitable as a second-phase material. Alcohols contain hydroxyl [—OH] groups, which raise the melting point and confer solubility in water and insolubility in wax.

The inventors performed a study of the properties of alcohols and found that 1,9-Nonanediol ($C_9H_{20}O_2$, referred to hereafter simply as Nonanediol) has a melting point of 45°–46° C., which is close enough to the desired range to be practicable as the second-phase material. The other properties of 1,9-Nonanediol is that it is non-toxic, is soluble in water, is insoluble in wax, as well as having the desired melting point range. In experiments, the inventors discovered that Nonanediol was stable when exposed to air, with little change in melting point. In mixtures with waxes, Nonanediol remains a distinct phase at low temperatures when both materials are solid, at intermediate temperatures where the wax is molten and the Nonanediol is solid, and at elevated temperatures where both materials are liquid. Therefore, Nonanediol was determined to be an exemplary embodiment of the second-phase material. The heat of fusion of nonanediol is 36.4 kJ/mol, equivalent to approximately 230 watt-seconds per gram of material. Thus, if 0.1 gram of Nonanediol were incorporated into the phase-change binder, then heating above the melting temperature of Nonanediol would be delayed until 23 watt-seconds of heat is applied above the amount of heat needed to melt the primary binding material. This phenomenon is known as a heating hysteresis.

As set forth above, the Nonanediol needs to be processed for mixture with the first-phase wax. A first step in this process is to create a finely divided powder of Nonanediol. In solid form, at or below room temperature, Nonanediol may be reduced to a fine powder by mechanical grinding with a mortar and pestle, by ball-milling, or by other measures known in the art for mechanically creating powders. If melted to its liquid form in a container containing a hydrophobic carrier liquid (for example, a non-polar solvent, such as hexane or heptane) vigorous shaking of the mixture may be used to reduce the Nonanediol phase to finely-divided emulsion droplets in the carrier liquid; the carrier liquid may then be removed by evaporation, filtering, or other measures. Alternatively, liquid Nonanediol may be sprayed from a nozzle and allowed to cool and solidify in cool air or inert gas to form a fine powder. Other measures known in the art may be used to reduce Nonanediol to a finely-divided powder.

Once the Nonanediol has been finely divided, it is compounded with the wax at a temperature below its melting point and below the melting point of the wax in a compounding mill. Alternately, the wax may also be finely divided to powder form, mixed with the Nonanediol in powder form, and the homogeneous mixture then warmed to fluidize the wax as the carrier phase of the mixture. Alternatively, the mixture may be fully liquefied by heating to above the melting point of both components and applying high-shear-rate mixing technology, high-pressure injection, or ultrasonic disruption to create colloidal mixtures and homogenized mixtures in the art.

Emulsifiers of several types are used in the art to stabilize food, cosmetic, paint, and other industrial oil-in-water or water-in-oil homogenized mixtures. Surfactants with molecular structures that are lipophilic on one end and hydrophilic on the other end, such as detergents and soaps, can be used to stabilize the multiphase mixture. Alternatively, powders such as clays, colloids, and sols (fumed silica, aerogel) that have an affinity for one of the phases and not the other may be used to create barrier layers around the particulates or droplets of the second phase.

One drawback to a binder (e.g., a two-phase mixture) that is heated above body temperature is that it is possible to damage tissue if the amount above body temperature is sufficiently high. An alternative to this "heat-for-flexibility" embodiment is to have the binder remain liquid at approximately body temperature but become solid slightly below body temperature, which is referred to as "cold stiffening" or, as will be described below, as "cold-fluid stiffening." In such a configuration, the catheter requires no additional energy to maintain a soft and trackable state. This ability to completely remove the requirement of heating the variflex section of the catheter also removes all mechanical features necessary for heating the variflex section, making the entire catheter simpler and less costly to produce. Additionally, lack of a heater remedies any risk that is present for a heater to fail, which could occur in a configuration where the binder is solid at body temperature and requires heat to melt and, thereby, increase flexibility. In the cold stiffening embodiment, the variflex section just needs to be cooled below body temperature in order to affect a transition from relatively flexible to relatively stiff. An exemplary embodiment to cool the variable stiffness element of the catheter is to inject relatively cold saline through the inner lumen 22 of the device (relatively cold being at a temperature of between approximately 10° C. and approximately 34° C. as compared to the temperature of the body or the vessel/blood in which the catheter resides). It is notable that the proximal opening of the inner lumen 22 in current non-variflex catheters is connected to a room-temperature (approximately 19° C. for operating room conditions) saline drip to prevent blood backflow. The cold stiffening embodiment, therefore, utilizes this blood-backflow-prevention process but adds to it a temperature control that regulates temperature and flow of the existing saline fluid supply and, thereby, affects a stiffening change of the binder when the user desires simply by adjusting the amount of energy applied to the saline to make it hotter (increasing energy) or colder (decreasing energy).

In an exemplary embodiment of the binder for cold fluid stiffening, the material is a mixture of a microcrystalline wax and a straight-chain alkane wax, similar to the mixture currently used in the heat-for-flexibility embodiments described. Straight-chain alkane waxes exist that melt at incrementally higher and higher temperatures so selection of the wax depends on where the melt temperature resides for that wax. Examples of the waxes that are usable depend on the melting temperature residing between approximately 23° C. and approximately 35° C. As long as the wax is within this range, it can be used. Some examples of this wax include tricosane, docosane, eicosane, nonadecane, and octadecane. In one exemplary embodiment for the binder in a cold stiffening configuration, the binder comprise a blend of microcrystalline wax and eicosane, the latter being a straight-chain alkane with twenty carbon atoms.

Figure 7A:
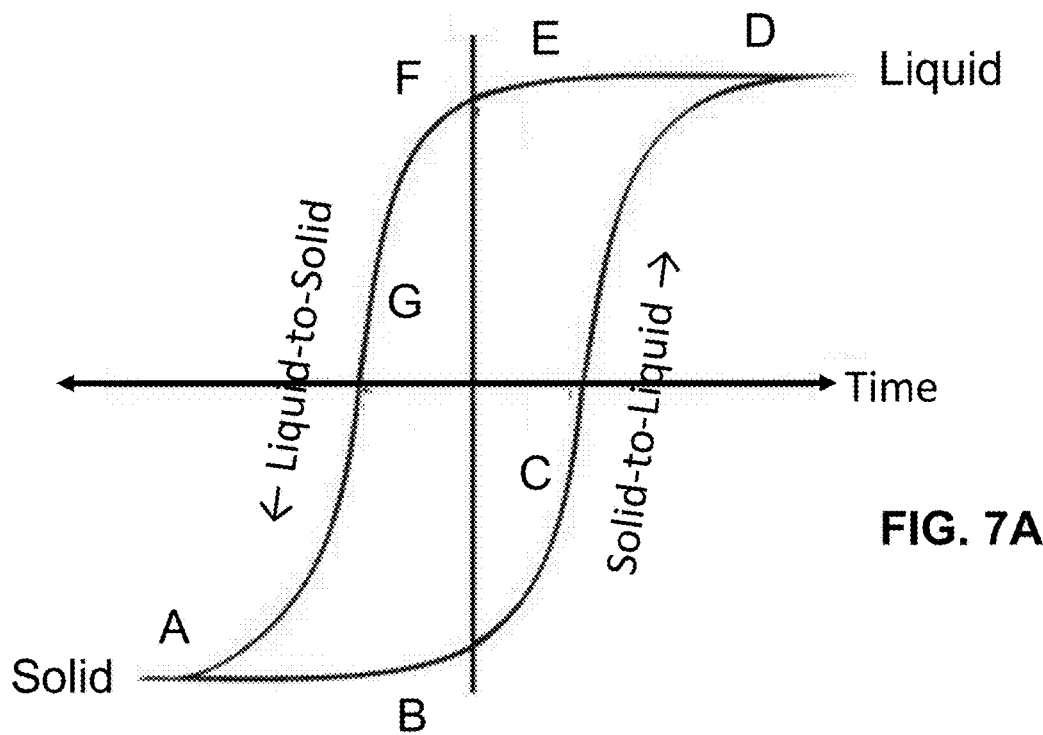

One characteristic of the binder when in a two-phase mixture as described herein (whether it is a heat-for-flexibility embodiment or a cold stiffening embodiment) is the fact that each of the materials undergo a melt hysteresis. The hysteresis effect is described along with FIG. 7A. When the binder materials are combined, in comparison, the combination also undergoes this melt hysteresis, but instead of the typical S-shaped hysteresis curve set, each of the curves in the set has an intermediate "rise" that creates a shape with two "S" connected to one another at the end of the first and the beginning of the second. With regard to FIG. 7A, the binder (here with one material for explanatory purposes) starts as a solid at point A in the curve. As heat is applied, the heat of fusion of the wax does not allow it to melt immediately, as shown in segment B of the solid-to-liquid right half of the hysteresis curve. The wax begins to melt after the heat of fusion temperature has been overcome and continues to melt through section C of the curve. The wax turns completely into a liquid at point D and remains a liquid even if further heat is applied as shown in right asymptote at the end of the solid-to-liquid portion of the curve. When cooled, however, to return to a solid, a different curve is produced, the liquid-to-solid left portion of the hysteresis curve. The liquid binder remains a liquid, throughout section E of the curve, until a point in time F where it starts to solidify. Solidification occurs over a time period G until all of the liquid has converted back to a solid at point A in the curve. When applied to the situation where the binder changes state somewhere above or below body temperature, the following scenario occurs in a head-for-flexibility embodiment. The binder starts as a solid and stays hard until the binder is above body temperature, at which time the binder is soft. When soft, the binder stays soft as long as it remains at or above body temperature. This means that the binder can cool to body temperature yet still remain soft. When it is desired to harden the binder, cooling of the binder begins. This binder stays soft until sufficiently below body temperature, at which time and temperature, the binder hardens. The lesson understood from this is that the binder experiences hysteresis and, therefore, is possibly both hard and soft at body temperature.

This delay in conversion from solid to liquid and from liquid to solid provides the benefit of having the binder absorb the heat as it is applied in the heat-for-flexibility embodiment instead of being absorbed by the surrounding tissue and absorb the cold as it is applied in the cold stiffening embodiment instead of being absorbed by the surrounding tissue. This increases the safety of the variflex catheter by slowing the rate of temperature rise over the temperature range in which the binder is undergoing phase change.

A significant detail in the construction of a variflex catheter is the process by which the space between the inner surface of the outer cylinder and the outer surface of the inner cylinder or base catheter is filled with binder, which space is referred to herein as a binder space. If there is a braid or a scaffold or a coil within the binder space, then that structure is to be coated or impregnated with the binder when the binder space is filled. For optimal results, complete saturation of the binder space is desired. In other words, air bubbles should be minimized to the greatest extent possible. If the binder space contains a scaffold or a braid, then the binder should take up all intermediate and surrounding spaces with respect to the scaffold/braid and should completely fill up any space between the scaffold/braid and the opposing walls of the inner and outer cylinders. It is also desirable to control the amount of binder that is deposited as well as the shape and profile taken on by the added binder material.

To address all of these concerns, in an exemplary embodiment, the binder is conveyed into the binder space with a vacuum transfer process, which is explained with reference to FIGS. 1 and 21 to 23. The catheter 10 is first constructed without binder 40. Shown in these figures is a diagrammatic representation of the variflex catheter 10 having the base catheter 20 (which can also include the inner cylinder 30) that is mounted on a mandrel 5 and is surrounded by the outer cylinder 50. After this configuration is constructed, the binder 40 fills the binder space 45 (between the inner and outer cylinders 20, 50 by vacuum transfer. An exemplary embodiment of a vacuum transfer device 600 is shown in FIGS. 21 to 23. The vacuum transfer device 600 comprises a mold having two mold parts 610, 620. The mold parts 610, 620 define an internal space 612, 622 that is shaped to contain the catheter 10 when it is to be vacuum filled with binder 40. To seal the internal space 612, 622 when the process occurs, a gasket 630 can be provided in a gasket sealing space 624 that can be in either or both mold parts 610, 620, here, the gasket sealing space 624 being provided in the lower mold part 620. The internal space 612, 622, therefore, provides a control volume that encloses the volume to be filled by the binder 40. This volume contain the braid/scaffold/cylinders and part of its boundaries can be defined by other catheter components such as the outer surface of the base catheter 20. The control volume is substantially air-tight. To perform vacuum transfer of the binder 40, the control volume is evacuated of air with a vacuum pump 640 (indicated diagrammatically with dashed lines in FIG. 22). The vacuum pump 640 is fluidically sealed to an outlet 614 of the control volume. The evacuated control volume is connected to a source of molten binder so that the vacuum draws the molten binder 40 into the control volume. The molten binder source in this exemplary embodiment is a reservoir 618 that is fluidically connected and sealed to an inlet 616 of the control volume. In this configuration, therefore, the entirely of the evacuated volume is filled by the drawn-in molten binder 40, leaving no voids or air bubbles. When the vacuum is provided, the binder 40 enters the binder space 45 between the base catheter 20 and the outer cylinder 50, completely filling the binder space 45 with binder 40. Non-illustrated valves can be placed between the vacuum pump 640 and the outlet 614 and between the reservoir 618 and the inlet 616 if desired.

A third part of the variable stiffness element is the heat-transition device. An exemplary embodiment of the heat-transition device for the variable stiffness element in a heat-for-flexibility configuration comprises a helical coil of wire that is electrically connected to a power controller and that is oriented so that, when ohmically heated, the coil transmits thermal energy through conduction to an associated scaffold and binding material. The heater coil can be a section of the catheter's reinforcement coil, or a separate coil. Also, the heater coil can be part of variflex catheter's reinforcement structure or it can be separate therefrom. Accordingly, a number of different heating coils are possible.

In a first exemplary embodiment, the heating coil can be a single pitch coil with a return conductor. In a second exemplary embodiment, the heating coil can have a bifilar configuration. In this context, bifilar is a structure where a parallel pair of wires are wound around an inner mandrel or cylinder to make a combined helix. At the distal end of the wires they are joined together to complete the circuit of a coiled heater. One beneficial characteristic of a bifilar structure of the heating element is that, when the two coils wound together, the current travels clockwise through one of the coils and then returns counterclockwise through the other coil. This opposing travel of nested coils produces an overall heater system inductance of zero; this is opposed to a meaningful inductance if only one helixed wire is present in the heater. As described in further detail below, because the heater can be excited with a high-frequency-switched field, inductance is an important characteristic to monitor because, if there exists a significant inductance, the current and voltage will be out of phase, which means that the wattage dissipated as heat will be less than the RMS voltage multiplied by the RMS current. In other words, the heater becomes an inefficient device because higher voltages and/or current would be needed than when applying ohmic heating. Another configuration of the bifilar heater takes advantage of the fact that the bifilar structure has the parallel pair of wires form a combined helix. To complete the circuit between the two helices, electrical contact is established at some location along the helix. The connection can be at the proximal end of the variable stiffness element or at an intermediate point or it can be at the distal-most location of the helices. This connection can employ characteristics of conductive metals. One embodiment can be a weld using radiopaque metals and another embodiment utilizes a conductive marker band made of a radiopaque material. As is known, the variflex catheter needs marker bands to assist a surgeon with navigation under fluoroscopy. Accordingly, connecting any portion of the heater with a radiopaque material provides the fluoroscopic marker for that purpose. Alternatives to the marker band embodiment include swaged-on machined bands and wound-on fine wire coils. Commonly chosen materials are platinum or a platinum-iridium alloy. Both construction tactics and material choices are applicable to the bifilar heater. After application of the marker band over the bifilar coil, the three parts are placed into electrical contact, which can be achieved by mechanical measures alone, as would be obtained with a swaged-on band, or through solder, laser welding, brazing, conductive adhesives, or other methods.

Like the dual-functionality of radio-opacity of the heater coil, the connection area of the heater coil can provide further functionality. If the connection area is formed by two dissimilar metals, then that junction can be used as a thermocouple to detect the localized temperature of the heater. This exemplary configuration is described in further detail below.

The heater configuration is not limited to a single pitch or bifilar configurations. Equally applicable is an embodiment where three, four, five, and more conductors extend to the variable stiffness element. And, in these multiple conductor embodiments, one or more of the conductor paths can be a resistance thermal device also known as resistance temperature detectors (RTD). Such configurations are described in further detail below.

Many materials can be used for the heater coil, which can also provide reinforcement for the catheter and, therefore, be a heater/reinforcement coil. Stainless steel, such as 304V, is commonly used in the art and has been shown to make effective reinforcement and heater coils. Platinum-iridium (PtIr) alloys exhibit excellent mechanical and conductivity properties, with the additional benefit of having high radio-opacity. Strengthened copper alloys are also excellent materials because of their high conductivities and mechanical properties comparable to mild stainless steels. Examples of suitable copper alloys include beryllium copper and Glidcop®, which is a copper strengthened through micro-dispersed oxide particles. Glidcop® is particularly favored for its high strength and high conductivity, which make it ideal for a heater wire. For example, Glidcop® alloy AL-25 has a conductivity of 87% IACS and a yield strength of 80 ksi. It is significantly more conductive than beryllium copper. Superelastic alloys such as Nitinol are also desirable because of their excellent toughness and deformability and resistivity similar to that of stainless steels. Alumel® has strength comparable to mild stainless steels, better conductivity, and can be used to form thermocouple-heater hybrids. Additional examples of materials for the heater coils are silver and nickel-cobalt alloys such as MP35N. It is sometimes desirable to electrically insulate the heater wires. In an exemplary embodiment, the heater wire is electrically insulated with polyamide (Kapton®) insulation. Examples of other suitable insulation materials include ceramic coatings, Formvar, Nylon, and polyesterimide. As a further coating, a given insulated wire can be coated with a bondcoat, which increases the wire's adhesion to polymer substrates during thermal laminations. This increased adhesion can provide mechanical benefits for a catheter built with bondcoated wired, which manifest as increased resistance to de-lamination. Examples of suitable bondcoats include nylon, polyester, and VG epoxy coatings.

Conductive wires are not the only possibility for forming the heater. In another exemplary embodiment, the conductive heating device can be a braid, a foil, photochemically engraved or laser-machined tubular structures.

An exemplary embodiment of a supporting structure (which is separate from the heater coil in the heat-for-flexibility embodiment), is a braided support tube of a non-conductive para-aramid synthetic fiber (e.g., poly-para-phenylene terephthalamide), such as Kevlar® and Twaron®. The non-conductive characteristic of this support tube is beneficial because it acts to prevent shorts that might otherwise occur if the support tube was conductive or metallic. For example, one possibility for a braided support tube is one made of stainless steel. Such a stainless steel braid increased torqability and reduced kinking. However, during manufacturing, it is possible for the conductor coil to short on that braid. By replacing the conductive support tube with a non-conductive material, the catheter retains is beneficial maneuverability characteristics but experiences no risk of shorting. Other materials for the non-conductive support tube include polyether ether ketone (PEEK) and laser cut polyimide tube, for example, of KAPTON®.

A further exemplary embodiment for the heater involves optical heating. Fiber optic fibers can be disposed down length of catheter. When light energy is transmitted through the fibers, either the fibers or another material can be configured to substantially absorb the received light and, thus, be heated. The heater can also be electromagnetically activated.

The temperature change can arise from outside the variflex catheter itself. In an exemplary embodiment, a guidewire having a heatable region can be disposed in the variflex catheter with the region aligned at the variable stiffness element and, when aligned, used to heat the binding material from inside the catheter.

As mentioned above, it is desirable to limit the amount of heat imparted to the heat-transition device. It is known that materials having positive coefficients of thermal expansion act as self-regulating ohmic heaters when compounded with an electrically conductive filler. When a voltage is applied across these materials, they pass an electrical current and begin to heat up. As temperature increases, the materials' effective resistance increases, limiting the amount of current that flows through the material and, therefore, limiting the internal heat generation. These self-limiting properties are fine-tuned through the choice of amount and type of conductive filler to deliver a specific target temperature at a specific applied voltage. A common conductive filler is carbon black, and a common base compound is polyethylene. Simple PTC materials can be made by compounding polyethylene with between approximately 10% and approximately 20% carbon black by mass. Specialty carbon blacks, such as Vulcan XC-72R (supplied by the Cabot Corporation), offer greatly improved material efficiency and ease of dispersion as compared to generic grades. In an exemplary embodiment, the polyethylene and carbon black is compounded in a compounding mill, or alternately compounded in a fluidized state. Another example provides a PTC scaffold. This is especially relevant in the above-described labyrinth construction. In particular, the labyrinth scaffold holds binder and is made up of a PTC material and, when current is applied, it also functions as a heater. Likewise, a PTC binder can be provided. If the binding material is compounded so that it functions as a PTC material with appropriate properties, the binder can be both the binder and the heater element.

From the above description of heating the binding material, issues of safety arise. For example, what happens if the variable stiffness device fails after having been made flexible and thereafter inserted to an anatomic location, at which time the failure causes the variable stiffness device to become stiff? With this situation, the variflex catheter might not be able to be removed while it is in the stiffened state. To account for a risk of electrical heater failure within the variflex catheter, an "emergency bailout device" is provided. Electrical heater failure within a variflex device could lead to an undesirable situation in which a variflex catheter is present in a patient's vasculature in a rigid state, without the native ability to heat itself up and be withdrawn safely. The emergency bailout device is used to apply thermal energy to the variflex catheter's variable stiffness element(s) without relying on the catheter's built-in wiring or heating systems. One exemplary embodiment of an emergency bailout device is a long, flexible device having an external size and profile closely matching that of the inner lumen of the variflex catheter. This device has a heater positioned to deliver thermal energy to the variflex catheter's variable stiffness element(s) from within the device's inner lumen. More specifically, the emergency bailout device is a guidewire having one or more heated regions and delivers heat to the variflex portion to impart flexibility in order to remove the catheter from the vasculature. Alternatively, instead of being inserted within the variflex catheter's inner lumen, another exemplary embodiment of an emergency bailout device is one that has a hollow inner lumen having an internal size and profile closely matching that of the outer surface of the variflex catheter. This device is inserted over the variflex catheter and positioned to place its heater over the variable stiffness element to deliver thermal energy inwards from outside the variflex catheter. In the exemplary embodiment where the catheter is cold-stiffening, such an emergency bailout is not needed because the binder is liquid at body temperature, meaning that the variflex catheter is at its most flexible state when at rest. Only when cooling fluid (e.g., through the inner lumen) is applied to the variable stiffness element does the flexibility lower and the variable stiffness element becomes stiff.

To optimize heater efficiency and help prevent excessive heating of, for example, endothelial tissue, it is beneficial to insulate the heater, binder, and scaffold from the catheter's exterior to the highest degree possible. The outer jacket (e.g., outer cylinder 50) encompassing the heater, the binder, and the scaffold is made from materials having additives that decrease thermal conductivity. One exemplary embodiment of outer cylinder 50 is a sleeve of Pebax 35D loaded with glass microspheres (for example, having a diameter of between approximately 0.5 μm and approximately 10 μm). The microspheres are so small that they do not compromise the mechanical strength and stiffness properties of the Pebax, yet serve to decrease the effective thermal conductivity of the Pebax-plus-microspheres matrix. The air entrapped within the microspheres is responsible for this effect. Other additives, such as aerogel powder, also lower the jacket material's thermal conductivity.

Figure 8:
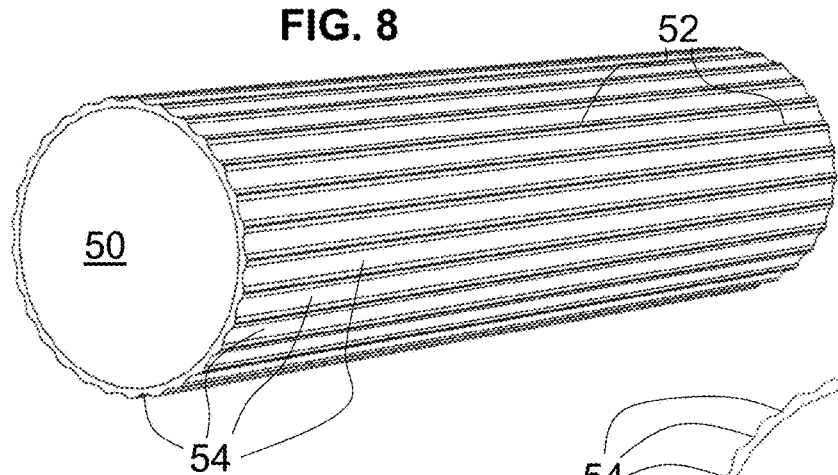
FIG. 8 is a fragmentary, perspective view of an exemplary embodiment of a configuration for an outer sheath for the variflex catheter.
Figure 9:
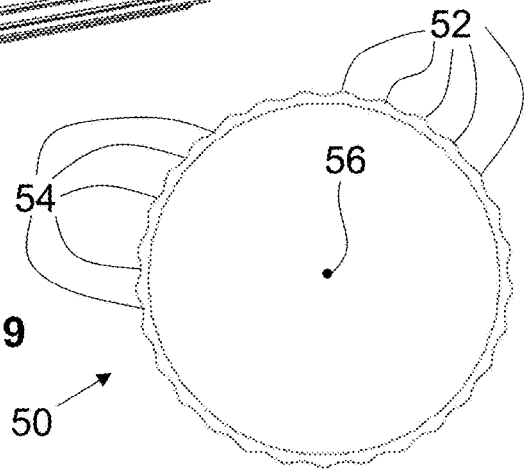
FIG. 9 is a fragmentary, cross-sectional view of the outer sheath of FIG. 8.

Another exemplary embodiment forms the outer cylinder 50 with a substantially non-circular outer cross-sectional shape. The outer cylinder 50 separates the heated portion of the variflex catheter (including the heater, the scaffold, and the binder) from a patient's bloodstream and endothelial tissues. The use of an outer cylinder 50 having a variegated, non-circular cross sectional shape, for example, allows for improved blood flow between the catheter's outer surface and the endothelial tissue. An exemplary embodiment of an outer cylinder 50 having such an outer cross-sectional shape is shown in FIGS. 8 and 9. Here, the outer cylinder 50 has bumps 52 protruding outwardly and defining therebetween channels 54 on the outer surface of the cylinder 50. In this exemplary embodiment, the channels 54 run parallel to the catheter's central axis 56. The bumps 52 can also be formed with non-illustrated discontinuities to permit flow between two adjacent channels 54. For example, breaks in the bumps 52 can define capillary channels at an angle to the longitudinally oriented channels 54 (e.g., acute, obtuse, or right). In either embodiment, shaping the outer surface improves blood flow, which aids in cooling the variflex catheter's outer surface. An additional benefit provided by this outer jacket geometry is a reduction in friction between the catheter's outer surface and the vessel's inner lumen and a reduction in friction between the catheter's outer surface and an inner lumen of any introducer sheath or guide catheter through which the variflex catheter is inserted, the reduction being caused by a decrease in the surface area of contact between the two opposing parts.

Catheters such as those described herein are subject to positive pressure when inserted into vasculature. If counteracting pressure is not applied in the inner lumen, blood would exit the proximal end of the inner lumen at pressure, which location is typically well outside the patient and within the operating theatre. Accordingly, to prevent blood from ejecting out of the proximal end of the inner lumen, fluid (e.g., IV fluid, saline) is applied to the proximal end of catheter at positive pressure into the inner lumen. Typically, such fluid is at room temperature, which is relatively cold compared to the catheter and, especially, it is significantly colder than the variable stiffness element and a temperature value needed to heat the catheter above body temperature when in the heat-for-flexibility embodiment. Therefore, when such cold fluid passes through the inner lumen, it affects adversely heating of the catheter and, especially, heating of the variable stiffness element.

As set forth herein, the variable stiffness element must reach a certain temperature in order to achieve a phase transition and mechanical softening. The heat that drives this temperature change comes from a heater coil that is, in exemplary embodiments, disposed directly outside the catheter's inner liner. If the fluid within the inner liner/device lumen is extremely cold, it will siphon away a disproportionate amount of heat from the heater coil, preventing adequate heating of the binder without the addition of an excessive amount of energy that could be unsafe. To avoid this deleterious temperature affect where the catheter could not be softened due to excessively cold fluid (e.g., saline), an inline fluid preheater is used to pre-condition the fluid's temperature. The fluid pre-heater is thermally connected to the fluid before or at the proximal entrance of the inner lumen. The fluid pre-heater imparts heat into the fluid to a desired temperature. First, the fluid is heated to a level that prevents adverse effects on the operation of the variflex catheter but still allows the fluid to counteract blood pressure and enter the vasculature. In particular, in the heat-for-flexibility embodiment, the fluid is heated close to or up to but not above body temperature. In such a state, therefore, the fluid has no adverse effect or at least has a neutral effect by not imparting any more heat to the catheter than the blood surrounding the catheter. This configuration removes the issue of the fluid cooling the variflex catheter internally at opposition to the heating of the variable stiffness element. In comparison to the cold-stiffness embodiment, the fluid is the actual mechanism for transferring heat to and from the variable stiffness element. When the fluid is at body temperature or slightly above, the variflex catheter remains flexible. However, when the fluid is cooled to a temperature sufficient to harden the binder, passing this cooled fluid causes binder hardening and stiffening of the variable stiffness element. Accordingly, the fluid pre-heater acts as a fluid cooling device when activated to cause stiffening by the cold fluid. In either embodiment, the fluid pre-heater can take the form of an external device or it can be built into the proximal shaft of the catheter in a fashion similar to the distal end's variflex heater.

To account for any risk of failure of a temperature feedback sensor within the variflex catheter, the control system of the variflex catheter can be programmed to periodically verify integrity of the sensors and, when a fault is detected, immediately suspend device function. Exemplary temperature control systems in which the fault detection is incorporated are described in further detail below.

To account for any risk of heater failure within the variflex catheter, the device's control system frequently checks the heater's integrity by performing resistance, impedance, inductance, and/or other electrical measurements and compares the measured values to a known baseline and/or to recent measurements of stated metrics. In the event that a heater malfunction is detected, such as a conductor breakage or a short circuit, the control system removes power from the heater, locks itself to prevent further heater activations, and informs the device user of the failure through feedback, which can include any combination of aural, visual, and/or haptic messaging. For example, a particular LED blink error code can be coupled with a vibration to signify heater failure. In such a situation, the emergency bailout device could be used.

Another exemplary embodiment to account for a risk of electrical heater failure is to design the scaffold and binding material of the variable stiffness element so that their resulting stiffness at or near human body temperature is adequate to provide support but is insignificant enough to allow the catheter to be slowly withdrawn in an unheated state in the case of a failure. One way to achieve such stiffness characteristics uses a material having non-Newtonian rheological characteristics when constructing one or more of the variflex catheter's components, namely the scaffold and/or the binder. An exemplary embodiment of a non-Newtonian material is silica-filled polydimethylsiloxane.

An additional method for protecting a patient's tissues from being overheated by the variflex catheter is to inject cooled fluid (e.g., saline) through the variflex catheter's inner lumen 22, 112 or, alternately, upstream of an overheated site into the given vessel's blood flow. As an example, such a system places temperature sensors on the variflex catheter's outer surface to detect overheating of tissue and, upon detecting an overheated condition, the control system triggers actuation of a powered fluid injector. The powered fluid injector, supplied/loaded with cooled fluid, dispenses the fluid to cool down the overheated region(s) quickly. This powered fluid injector can be attached to or integral with the fluid pre-heater mentioned herein.

To help prevent the variflex catheter from being retracted aggressively while in a stiffened state, with the resulting injurious consequences, the control system is provided with measures to sense motion and provide distinct feedback to the user with the intent of stopping such motion. In one exemplary embodiment, an inertial measurement system is added to the control system's circuitry along with a haptic feedback device, such as a sound transducer and/or a vibration generator. When the inertial measurement system, which in an exemplary embodiment is a MEMS accelerometer, detects withdrawal motion while the variflex catheter is known to be in a stiffened state, the control unit emits sounds and/or vibrates the handle of the device, immediately warning the user to stop movement until the variflex catheter reaches a safe softened state. Other exemplary embodiments to sense motion include accelerometers, gyroscopes, magnetometers, and optical sensors.

Sterilization is an important step in the manufacture of devices intended for use in the human body. One way to ensure the continuing sterility and safety of a variflex catheter is to include sterility-promoting additives in the binding material, in the scaffold, or in both. One exemplary additive is silver metal powder, which is used as an antimicrobial agent and is able to be compounded into rubbers such as latex to prevent bacterial growth. Silver chloride is another preferred additive with similar properties. Various proprietary additives are also available from industry sources. Choice examples are BactiBlock® from Nano-biomatters and Alphasan from Milliken Chemical. When introduced in the binding material, the scaffold, or both, these sterility additives are processed into a fine powder and are micro-dispersed within the binding material and/or scaffold material before further processing and forming of the variflex catheter.

As described in further detail below with regard to FIGS. 14 to 16, the proximal shaft of a catheter needs to be stiff and pushable in order to traverse the tortuous anatomy, such as in blood vessels. For catheters in general, this is normally realized by adding a metal reinforcement braid or coil within the proximal portion of the shaft. In the variflex catheter, metal reinforcements have been found to increase a risk of electrical faults by shorting wires present in the proximal portion of the shaft. An alternative strengthening technique that is desirable from a safety standpoint utilizes non-conductive materials. One exemplary embodiment of a non-conductive stiffener is a braid of Kevlar®, as is described herein. This braid is continued proximally into the proximal portion of the shaft, e.g., at a higher turns rate. Additionally or alternatively, this proximal portion of the braid is saturated with a thermoplastic such as Pebax that, together, forms a rigid composite shaft.

With regard to traversing tortuous anatomy, even with a very lubricious outer surface, it the issue of hindered movement within a vessel to a target site remains. One way to improve trackability and to minimize the force required to advance a catheter through a vessel is to attach a vibration source to the variflex catheter. One exemplary embodiment of a vibration source includes a pager motor, which, when physically coupled to the shaft of the variflex catheter, imparts vibration along the longitudinal length of the variflex catheter. This vibration keeps the catheter moving relative to the vasculature and, therefore, maintains a kinetic frictional mode, which offers less resistance than a static one as the catheter is moved to and from a target site. Importantly, the catheter has fewer forces to overcome when advanced. As vibration imparted by the source to the catheter travels along the entire longitudinal length of the catheter, in an exemplary embodiment, the vibration source is located at the proximal section of the catheter, such as in the handle.

In the variflex catheter, a substantial percentage of the overall length has a diameter that is minimized and within a range that surgeons find acceptable for introducing the device into a patient. In some exemplary embodiments, the variable stiffness element has a diameter that is greater than the predominant outer diameter of the variflex catheter. Surgeons are reluctant to use catheters over a certain size because of the correspondingly large punctures required in the patient for device introduction. In particular, neurovascular interventionalists generally shy away from devices having a diameter over 8F (approximately 2.3 mm). However, if the entry port is expanded to greater than 8F only for a short period of time, the surgeon's opinion to be disinclined to use a larger diameter catheter changes. Accordingly, an expandable, hollow introducer sheath is provided. The introducer sheath has an outer diameter of approximately 8F. The introducer sheath is inserted into the entry port and the variflex catheter is threaded through the central lumen of the introducer sheath in order to enter the patient. When the larger section of the variflex catheter is required to pass through the entry port, the user causes the introducer to temporarily dilate and, thereby, accommodate a larger diameter catheter within the sheath's central lumen. After the larger section passes into the patient and exits the introducer sheath, the user causes the introducer to contract back to the steady state of the introducer, which is at an outer diameter of 8F or less. This expansion of the entry site for only a short amount of time allows introduction of devices having an external diameter greater than 8F without increasing tissue damage at the introduction site because the entry site is able to stretch elastically when the time of such expansion is measured in seconds. In instances where the distal, variable stiffness element of the variflex catheter has a greater diameter than the device's proximal shaft (the predominant portion of the entire catheter), the introducer sheath aids the surgical procedure for inserting the variflex catheter to the surgical site of interest.

Figure 10:
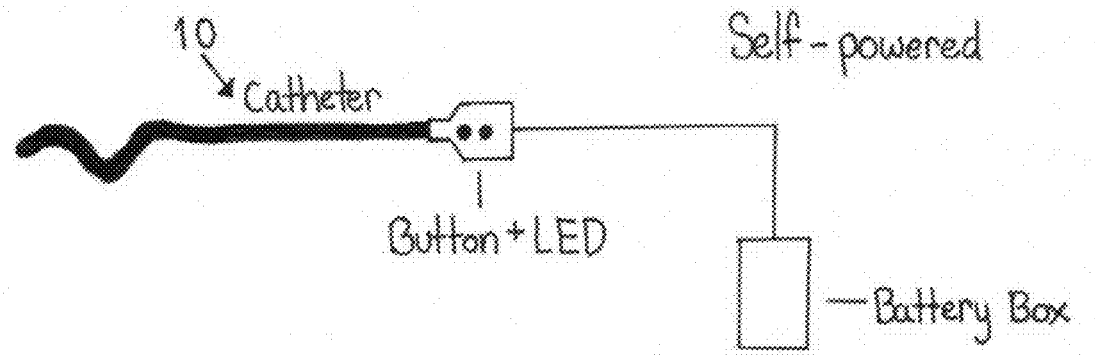
FIG. 10 is a diagrammatic illustration of an exemplary embodiment of a self-powered variflex catheter with a battery compartment separated from a handle.
Figure 11:
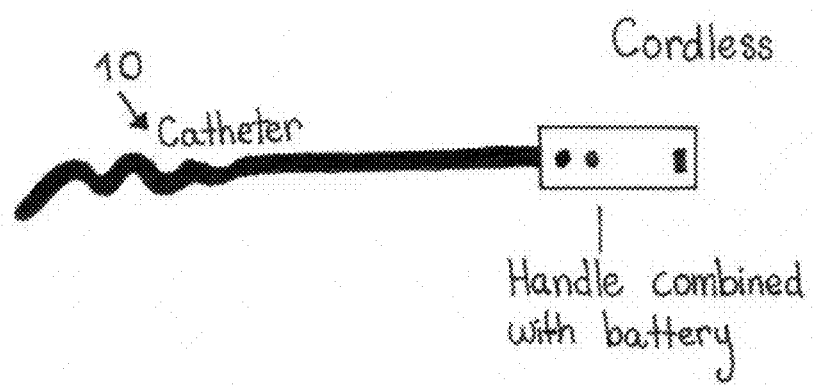
FIG. 11 is a diagrammatic illustration of an exemplary embodiment of a self-powered variflex catheter with a battery compartment integrated with a handle.
Figure 12:
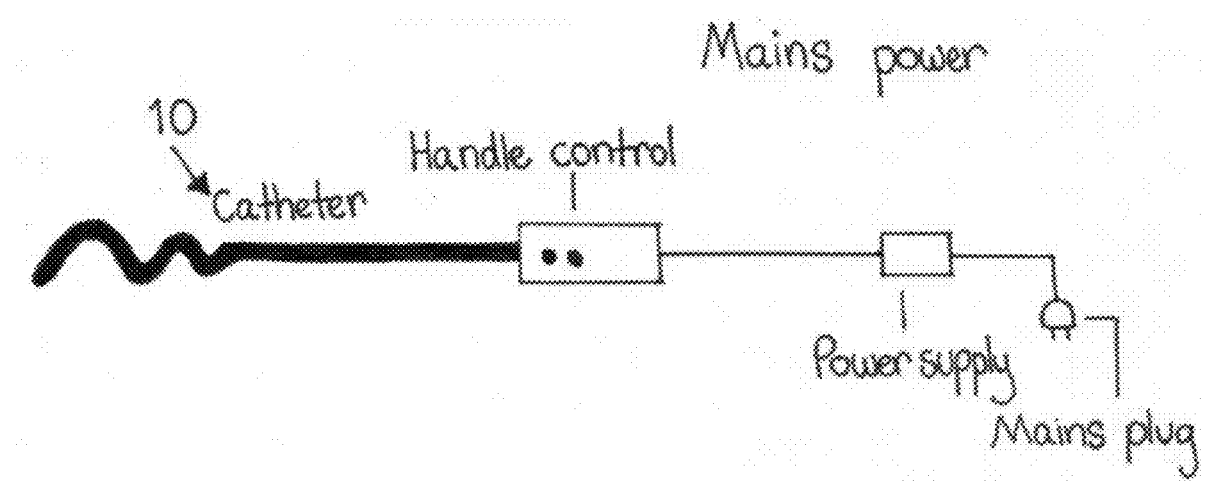
FIG. 12 is a diagrammatic illustration of an exemplary embodiment of a mains-powered variflex catheter.

The power control system of the variflex catheter can comprise any number of configurations. For example, as shown in FIGS. 10, 11, and 12, the power control system can be disposed inside a battery box that is electrically connected to the variflex catheter 10 (FIG. 10), inside a handle on variflex catheter's proximal end (FIG. 11), or inside a power supply entirely separate from the variflex catheter 10 (FIG. 12), or a combination of these. With regard to the electrical power that is supplied, the power can include direct current (DC) or alternating current (AC), including low frequency, high frequency, pulse width modulation (PWM), pulse frequency modulation (PFM). The controls and user interface displays are illustrated on the handle but can be associated with the power supply.

The power can arrive from a battery, either built into the variflex catheter or from an external battery pack (FIG. 10 or 11). Direct current is simple to provide in a battery-operated device, but has certain clinical limitations. Although the electrical circuit of the variflex catheter is isolated from the patient and user, failure of insulation at one or more points could result in current flowing through the patient's body. Such current, if DC, can result in nerve activation and muscle spasm, which is undesirable. Accordingly, it is common to use alternating current at a frequency sufficiently high to eliminate the stimulation of neuromuscular structures. A frequency of at least 50 kHz is sufficient to achieve this result, although many systems using alternating current in direct contact with the patient, such as RF electrosurgery, use a frequency between 300 kHz and 1 MHz. FIG. 12 depicts an exemplary embodiment where AC power is drawn from a wall outlet.

Representative exemplary embodiments of variflex catheters described herein have a resistive heater with resistance of approximately 10 ohms to approximately 50 ohms. The power required to achieve sufficient heating in the variflex catheter is approximately 1 to approximately 4 watts. Accordingly, battery voltages between 3 and 20 volts can be used to achieve this level of heating (heating DC power equals the voltage squared divided by the resistance of the heater). When using direct current, there is no difference in the behavior of the heater if it happens to have a reactive inductive component, as would happen if it were a helically-wound coil.

The voltage and power requirements for heating with alternating current are the same with alternating current as with direct current, but the design needs to allow for any reactive characteristic of the heater when calculating the power that will be dissipated. If the heating element is a simple helical coil, which has inductance, then there will be a reactive component to its impedance that will shift the phase of the current relative to the voltage. If there is a reactive component, then the power actually dissipated in the heater will be the product of the current and voltage reduced by the Power Factor PF, which is a complex function of resistance, inductance, and frequency according to the formula:

$$PF=\sin(\arctan(R/(2\cdot\pi\cdot f\cdot L))), \text{ where:}$$

R is resistance in ohms;
f is frequency in Hertz; and
L is inductance in Henrys.

Power factor in a pure resistive circuit (one without any inductance or capacitance) is equal to 1.0. When inductance is added to the circuit, the Power Factor has a value less than 1.0, and that value becomes less as the inductance or frequency increases. The result is that, for a given actual heating power delivered to the heater, the voltage and current must be higher than would be necessary with direct current. If high frequencies are needed, and if PF becomes a significant factor in the design, then it is advantageous to make the heater in a bifilar, non-inductive design as described herein.

Alternatively, the variflex catheter could inductively draw power from an induction coil positioned on operating table, on patient underneath of a resting location of a proximal hub, or through electromagnetic energy directed through the patient to an induction target along the length of the catheter.

There are various methods for sensing temperature of the variable stiffness element and/or other parts of the variflex catheter. For example, thermocouple or other temperature sensor can be used for feedback to the control system. One or more thermocouples can be placed along the length of the variflex catheter at the variable stiffness element, proximal of the variable stiffness element, and/or distal of the variable stiffness element, and the thermocouples can be within the catheter or outside the catheter. For example, the thermocouple(s) can be inside the scaffold (e.g., the braid), outside the scaffold, and/or near the heating coil. Multiple thermocouple junctions can be combined to provide an average temperature. To form such a configuration, thermocouple wires are joined together in multiple places, creating multiple junctions in parallel with each other. As such, when voltage is measured across the junction system, the measurement will correspond to an average temperature of all of the junctions. When the variflex catheter 10 has thermocouples both proximal and distal of the variable stiffness element(s), it is possible to measure change in blood temperature across the element(s) and to obtain a corresponding approximate heat loss from catheter (through the specific heat formula $Q=mc\Delta T$).

In still another exemplary embodiment, temperature sensors can be constructed with wire, etched foil, and/or flex circuit techniques. Thermocouples can easily be made with two wires, one of each chosen metal or alloy, where one end of each wire is placed in electrical contact with the other, forming a junction. This electrical contact can be achieved with welding, soldering, mechanical engagement, etc. One exemplary embodiment of a two-wire thermocouple is provided by chromel and alumel, and is constructed from fine insulated wire such as 44-30AWG.

In an exemplary embodiment, thermistors can also be used to control heating, such as a BC104R1k chip thermistor made by U.S. Sensor. Optical controllers such as a retro-reflective gallium-arsenide chip bonded to fiber optic, e.g., TSNano-02 manufactured by Micronor, are a viable option. A printed thermocouple sensor, using either flex-circuit technology (metal on insulating film) or thick-film (metallic ink on film or directly on the catheter), is also a possible option.

In a further exemplary embodiment, resistance temperature detector (RTD) sensors, using resistance material with known temperature coefficient of resistance, can also be used to sense temperature at the variflex catheter. RTD sensors use only one alloy in their sensing element and measure temperature change based on the element's corresponding change in electrical resistivity. The most common material used in RTD sensors is platinum. Platinum RTD's are commonly made from coils of platinum wire and could also be fabricated with foil etching. Other types of wires utilized include precious-metal alloy wire, stainless-steel wire, and/or thick-film or thin-film resistors. Various RTD embodiments are discussed in further detail below.

Thermocouples for the variflex catheter can also be made with subtractive techniques. For example, thin sheets of the chosen alloys are placed on an insulating carrier material, such as polyimide, and are masked and etched with an etchant such as ferric chloride, leaving behind a thermocouple that is very thin and flexible and bonded to the insulating carrier. (This is the basis for etched foil and flex circuit techniques.) With regard to the sensing of temperature in the variflex catheter, various kinds of feedback can be provided to the user, these include audio, visual, and haptic indication of device status. Individual indications include, but are not limited to, the current state of heating/cooling, the current process of heating and cooling, and any errors that are detected. To activate the heating, a button or a switch disposed on some part of the variflex catheter or on an external control pad or pedal can be actuated. And, upon activation, the variflex catheter can provide audio, haptic, and/or visual feedback. The switch can require the user to continue to press over a specified duration or to impart multiple presses to activate heating or cooling.

Intrinsic resistance of the heater structure, which is related to the temperature of the heater material, may be determined by measuring voltage drop across and current flowing through the resistance-heating element. This measurement can either be accomplished when heating current is flowing or between pulses of heating current by introducing a lower current for the purpose of measuring voltage drop. The voltage-drop sensing may be measured from the proximal end of the catheter by compensating for the voltage drop of the current-carrying lead wires that extend over the length of the catheter to the heating element; or, the voltage may be sensed by either one or two independent sensing connections through which the current flow would be negligible, as is common in the art in the form of a "Kelvin connection."

In another exemplary embodiment, the heater, itself, may be constructed from one or more of the thermocouple alloy metal wires. In such a case, a junction is present where the two metals meet at some desired point along the heating element. Temperature is measured by momentarily discontinuing the heating current so that the small thermocouple voltage can be sensed. Alternately, the heating element may be constructed substantially of one of the thermocouple metal alloys and a third conductor, made of the second thermocouple metal alloy, and joined to the heating element at a point where temperature measurement is desired; again, heating current is disabled momentarily to measure the small thermocouple voltage. If desired, additional conductors of the second alloy could be joined to the heating element at additional points in order to have multiple sensing locations.

In yet another exemplary embodiment, an averaging thermocouple can be utilized. More specifically, a distributed thermocouple structure is made by connecting parallel lengths of the two thermocouple alloy wires by a semi-conductive (resistive) compound. For example, a 2-inch length of 0.003" diameter alumel wire laid parallel to a 2-inch length of 0.003" chromel wire separated by 0.010 inches, wherein the gap between the wires is filled by a resistive polymer compound (for example, graphite in silicone rubber), yields a thermocouple structure that generates a voltage corresponding approximately to the average temperature along the 2-inch length.

Figure 13:
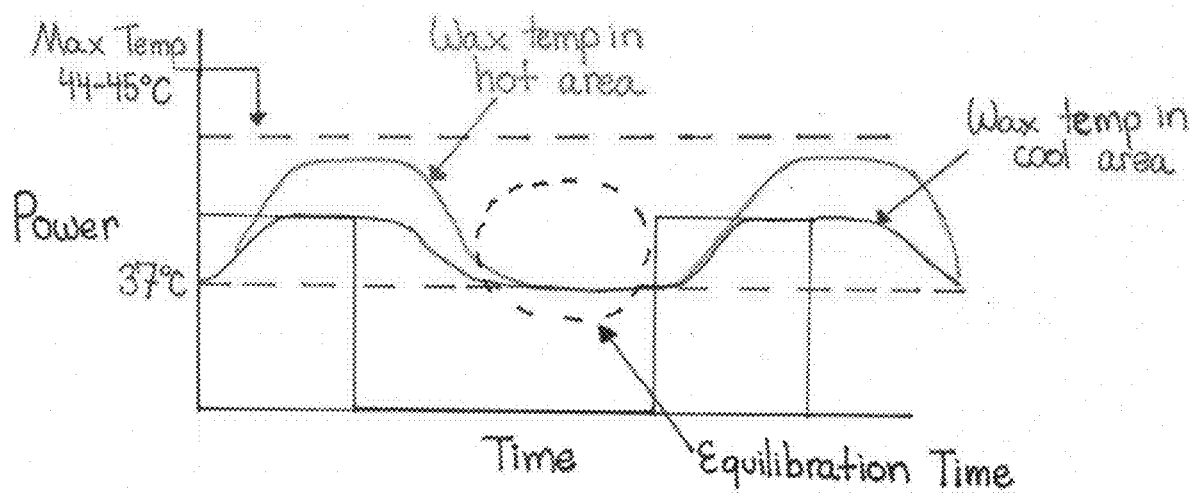
FIG. 13 is a graph of power versus time for an exemplary embodiment of a method for providing power to a heating element of the variflex catheter.

Delivery of power can also be used to ensure that overheating does not occur. The variflex catheter can have a constant-current mode or a constant power mode. Through testing, a pre-determined maximum delivery of energy over time was found and is implemented to prevent delivery of energy over that maximum. One method for safely heating the variable stiffness element(s) in the event of a temperature sensor failure is to deliver a constant amount of power to the heater. This amount of power is experimentally and empirically derived, and is based on expected conductive and convective heat loss from the variflex catheter's heated portion to saline, bloodflow, tissue, and any other relevant subject. For a given variflex catheter design, a safe constant power level is determined through benchtop testing, animal testing, FEA simulation, etc. This power level can be enough to somewhat soften the variable stiffness element, allowing withdrawal, but just not enough to achieve full flexibility. In the event of a temperature sensor failure, this constant power mode can be activated to allow the catheter's safe withdrawal from a patient's anatomy. As delivered power is a function of voltage and current, as well as inductance in cases where alternating frequency is being used to drive the heater, the power controller is programmed to sense these values during a constant power operation and to adjust output to maintain constant power. For example, to account for slowly decreasing output voltages due to battery sag, the controller correspondingly increases the output duty cycle, resulting in constant output power. Algorithms for achieving this function include proportional-integral-derivative (PID) control and pulsatile heating, where the heat left on only long enough to provide energy adequate to soften the active portion of the variable stiffness element. This is followed by a cooling and an equilibration period as shown, for example, in FIG. 13.

The thermal control system in the variflex catheter uses a precisely formulated wax mixture that melts at slightly above human body temperature. For melting this mixture, the thermal control system controls temperature accurately and precisely and compensates for changes in thermal load as the variflex catheter is actuated (a) in air outside the body, (b) within the body in flowing blood, and (c) within the body in partial contact with tissue.

A number of different control algorithms can be used to control the heating processes of the variflex catheter. In an exemplary embodiment utilizing thermostatic control, heating current is switched on when the sensing element detects that the sensed temperature has fallen below a desired setpoint. Heating current is thereafter turned off when the temperature rises above the setpoint. This form of temperature control is simple, but it results in overshoot and undershoot because the temperature will continue to rise after the heat is turned off and will continue to fall after the heating current is turned on because there is a delay between when electrical heating energy is applied and when temperature is measured. In an exemplary embodiment utilizing proportional control, the heating current is modulated so that the amount of heating current is proportional to the deviation from the desired setpoint. This form of control results in a smoother controlled temperature, but generally results in a steady-state temperature that is either above or below the desired setpoint, depending upon the percentage of power that is required to maintain the desired setpoint. In a further exemplary embodiment, proportional-plus-integral control may be applied. This method is similar to proportional control, but includes an additional function to adjust the proportional-controlling setpoint so that the system is made to approach the actual desired setpoint over a period of time. Over a long period of time, the average temperature is monitored and the proportional-controlling setpoint is automatically adjusted up or down so that the steady-state temperature produced by the proportional action is made to coincide with the actual desired setpoint. Still in another exemplary embodiment, proportional-integral-derivative control, which is similar to proportional-plus-integral control, includes a further additional function to monitor the speed at which the system is approaching the desired setpoint. If the speed of approach is very high, the control function is modulated to reduce the power level so that overshoot and undershoot is minimized. For example, if the temperature is rising rapidly toward the setpoint, the heating power is reduced to a level lower than would be used if the temperature were rising slowly. This is referred to in the art as PID control. Additional algorithms of temperature control may be used, including Kalman filtering, feed-forward control, and more advanced analog or digital methods in order to improve control of the temperature of the system even when external changes occur, such as sudden immersion of the device into fluid, initial heating conditions from ambient temperature, and the effect of changes in heat capacity of the system as phase changes occur within the binder materials.

In an embodiment where the variflex catheter is intended for use in the human body, in which it is particularly hazardous to allow the temperature to reach levels that may result in physiological damage, certain characteristics are necessitated. For example, it may be desirable to ensure that it is very unlikely for any portion of the device to ever reach a temperature above 50° C. The structure of the variflex catheter and its heat capacity as a function of temperature is, therefore, well characterized. The operating environment in which the variflex catheter likely be one of either (a) open air in an air-conditioned room or (b) in the bloodstream of a human being at normal body temperature. Finally, along the length of a heated portion of the variflex catheter, there may be varying cooling loads offered by differing amounts of blood circulation, temperature of flushing fluids, turbulence, and contact with vessel walls. As a result, even with a uniform application of heating energy, the temperature may vary along the heated length of the variflex catheter. Although the temperature is well controlled at the particular location where temperature is measured (for example, by a thermocouple) to control the heating power input, the temperature in other areas may be different. For example, if the location where a thermocouple is used to measure temperature happens to be highly cooled by turbulently-flowing blood, and at another location the variflex catheter is in a lower-flow area or is pressed against a vessel wall, it would be expected that the temperature at the low-flow or vessel-wall-contact area would be higher than the temperature at the measurement point. This condition occurs because the highly cooling environment where the temperature is being measured requires a high level of heating power to achieve the desired temperature; meanwhile, the temperature at the less-actively cooled area could rise above the desired level. Thus, the process used to control energy becomes significant.

Because of the structure of the variflex catheter and its materials of construction, some of its thermal characteristics may be predicted. For example, it is possible to measure the amount of thermal energy that, if imparted to the system over a short time (cheat, during which time the heat loss from the device to its environment is negligible), will result in raising the temperature of the binding material to the level needed to achieve the desired flexibility; this temperature is designated $T_{flex}$ and the amount of energy is designated $H_{flex}$. Once $H_{flex}$ is known, it is possible to use a control algorithm in which the energy $H_{flex}$ is applied over the short period of time $t_{heat}$, followed by a cooling/equilibration time known by experiment to be sufficient to ensure that the temperature of the hottest portion of the variflex catheter returns to a value $T_{body}$ near that of the ambient blood (e.g., 37° C.). Following the cooling time $t_{cool}$, another increment of heat energy $H_{flex}$ can be applied, followed by another time $t_{cool}$, and so forth. This control method could be used without feedback, ensuring that no portion of the catheter is heated to a temperature substantially above the maximum safe temperature and is referred to as Adiabatic Energy Control. Experiments with the variflex catheter indicate that the time-constant of response to heating input is in the range of 2 to 3 seconds and the time to return to body temperature in still body-temperature water is 5 to 10 seconds; accordingly, $t_{heat}$ is in the range of approximately one second, and $t_{cool}$ is in the range of approximately 5 to approximately 10 seconds.

The above Adiabatic Energy Control method may be enhanced by combining it with PID or other control algorithms. In an exemplary embodiment, the control system is programmed so that, after the variflex catheter achieves initial equilibration to $T_{body}$, the system is limited to applying energy pulses equal to or less than $H_{flex}$. However, the primary control algorithm in action would still be PID, with the limitation that, for a given period of time equal to $t_{heat}+t_{cool}$, no more energy than $H_{flex}$ can be applied during that time. The resulting action of this control algorithm is that the catheter experiences cooling periods in which its flexibility diminishes, followed by periods of the desired amount of flexibility. Assuming the heating and cooling time constants, the time $t_{heat}+t_{cool}$ is in a range of approximately 6 to approximately 11 seconds, resulting (in a worst case) in some stiffening of the variflex catheter every few seconds. While this method might result in some inconvenience to the user, because the flexibility of the variflex catheter is modulated over time while in its "flexible" state, there is additional insurance that no area of the catheter exceeds the safe temperature. Because there is a latent heat of phase change required for the device to transition from flexible to stiff at the temperature $T_{flex}$, the stiffening during the time $t_{cool}$ is even less noticeable than expected if the flexibility were simply proportional to temperature.

It is possible for the control system to determine the environment in which the flexibility-controlled portion of the device is operating, given that it will be one of two possible environments: in free air or in the bloodstream. An exemplary control process is used either independently or in concert to determine which of these conditions is present. Initially, temperature is sensed while the heating power has been turned off for a few seconds. It is known that when the variflex catheter is in free air (e.g., in an operating-room environment), the temperature will be between 17° C. and 27° C. When placed in the bloodstream and once stable, the temperature of the variflex catheter will be between 35° C. and 39° C. These temperatures are easily distinguished. A given pulse of energy is applied to the variflex catheter that is known to raise the temperature in air and in water by known amounts. The measured temperature increase after a few seconds will determine which environment the variflex catheter is operating. These exemplary methods may be used singly or together and may be applied multiple times or periodically in order to determine actively the operating environment of the device. Once the environment has been determined, the appropriate control parameters for proportion, integral, derivative, and $H_{flex}$ may be applied to the control algorithm in use.

In some instances, it is desirable to have the variflex catheter be as flexible as possible. This means that, with a heat-for-flexibility embodiment, the temperature to cause such increase in flexibility might be too high for the tissue in which the heated portion of the variflex catheter, which means that there is a chance that the tissue might be damaged. Heating tissue to such an extent causes damage when that heat is applied for more than a given amount of time, which can be defined as damage time. However, if the time in which the enhanced heat occurs is less than damage time, for example, at least ten percent (10%) less than damage time, the tissue will not be damaged when such heat is applied. It is further understood that the variflex catheter heated to temperatures above body temperature is continually caused to cool when it resides within a patient. Such cooling takes place relatively quickly, especially when the variflex catheter has an outer diameter mostly less than 8F. With these characteristics in mind, the control system can be caused to pulse in what is referred to as a short boost mode. In the short boost mode, the control system temporarily heats the variflex catheter to a temperature higher than the device's flexibility inducing temperature set point with the intention of gaining as much flexibility as possible in the variflex catheter. If left for longer than the damage time, the increased temperature would damage the surrounding tissue. Therefore, the boost mode occurs for a period of time less than the damage time, but in a pulsed manner for a given number of times. The control system allows the catheter to cool within the vessel in which it is placed and then enters the boost mode, again heating the variflex catheter above the temperature set point but for not longer than the damage time. Specific exposure times and counts can be calculated for the relevant tissue in which the variflex catheter is placed with a thermal dosimetry model, such as the $CEM_{43}$ model mentioned in *Thresholds for thermal damage to normal tissues: An update* by Yarmolenko et al., published in the International Journal for Hyperthermia in 2011, which is incorporated herein by reference in its entirety.

Various components of the variflex catheter can be used together or separately to form a number of different alternative embodiments. The following details a few exemplary embodiments and these examples detail groupings of component varieties, but are not considered to be limited to only these configurations.

Figure 14:
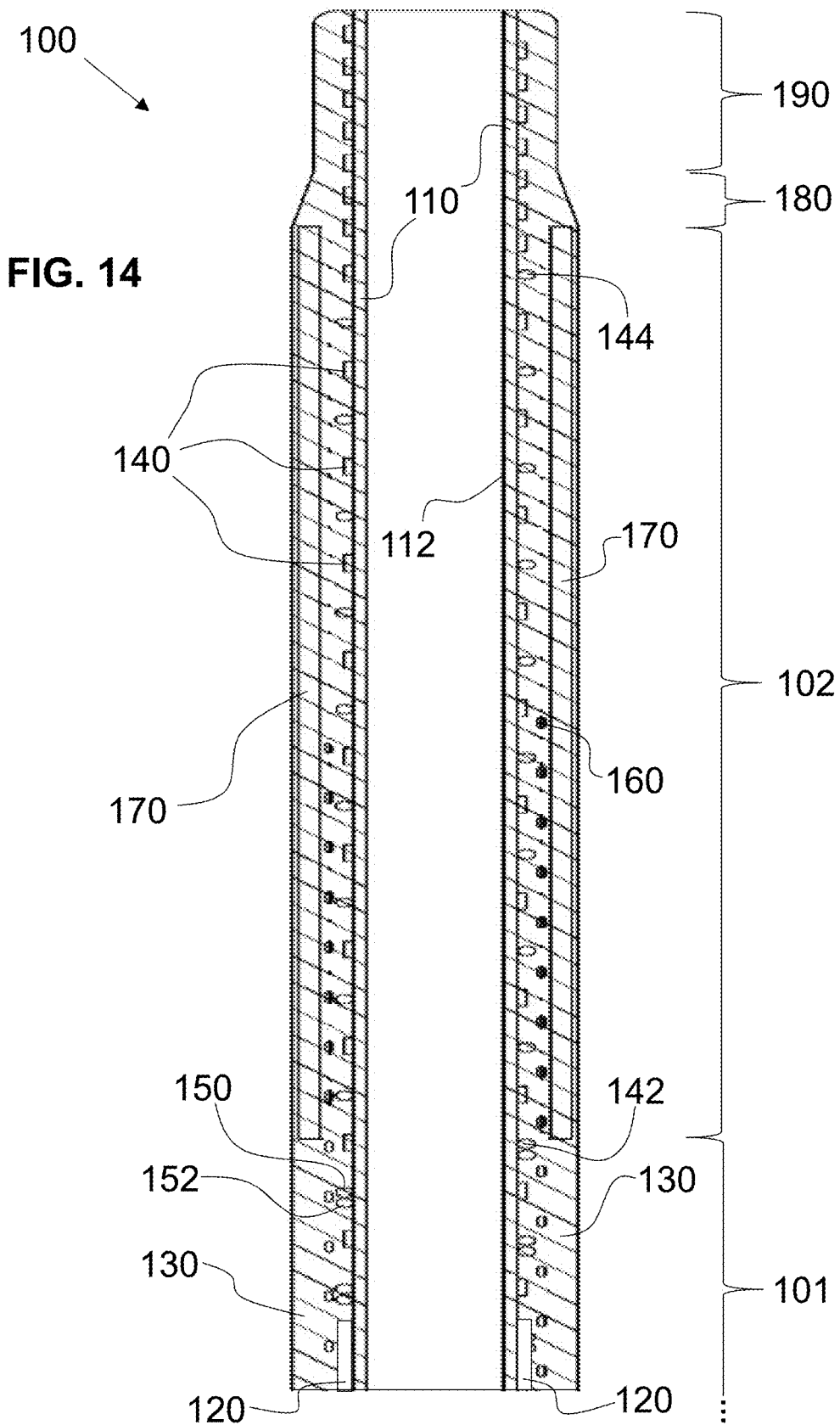
FIG. 14 is a fragmentary, enlarged, cross-sectional view of a distal end of an exemplary embodiment of a variflex catheter with a variable stiffness element with an internal thermocouple.
Figure 15:
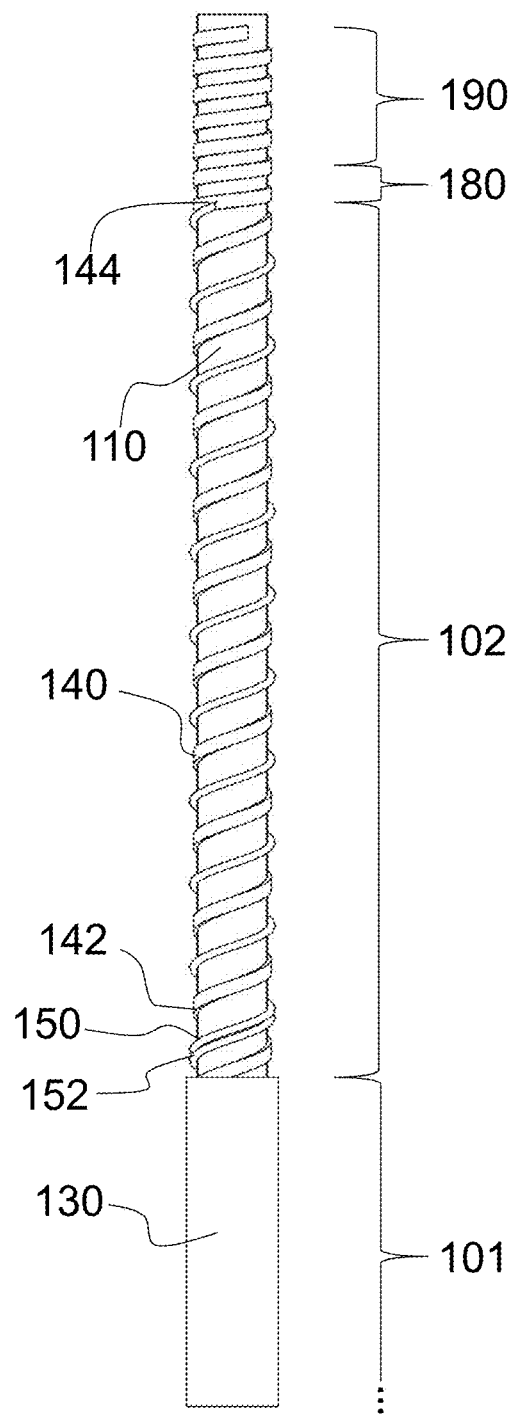
FIG. 15 is a fragmentary, enlarged, side elevational and partially cut away view of a distal end of a liner, heater subassembly, and a cover of the variflex catheter of FIG. 14.
Figure 16:
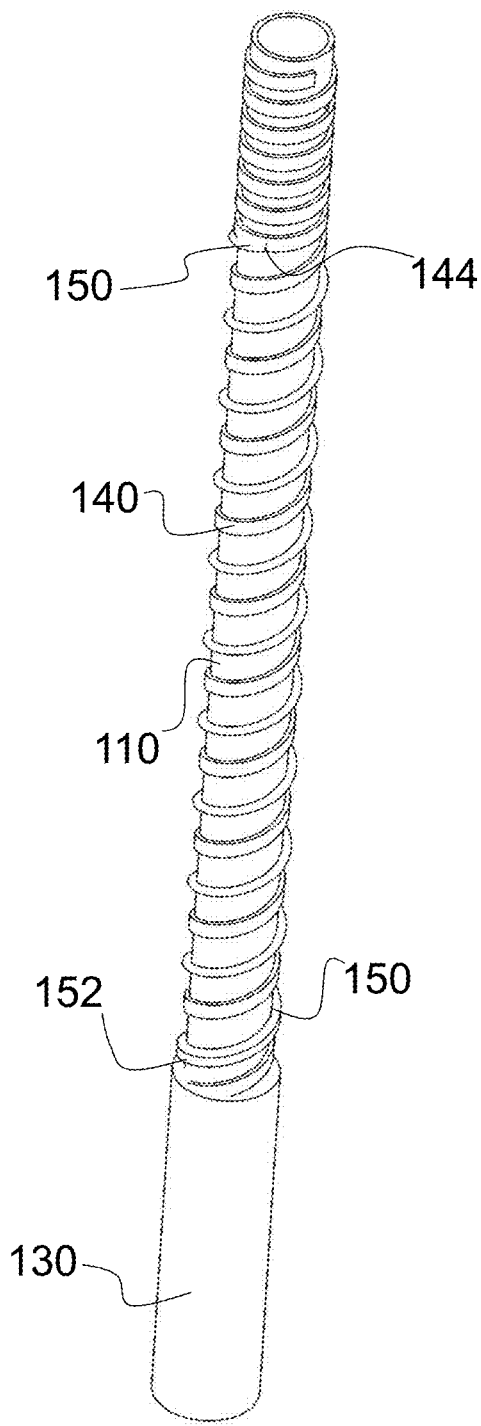
FIG. 16 is a fragmentary, enlarged, perspective and partially cut away view of the liner, the heater subassembly, and the cover of FIG. 15.

An exemplary embodiment of a variflex catheter 100 is shown and described with regard to FIGS. 14 to 16. This variflex catheter 100 has an internal diameter of approximately 0.07" (1.78 mm) but it can be expanded to larger sized catheters of up to 2.67 mm. The catheter starts by being built over a mandrel that closely supports an inner surface of a liner 110, which forms the inner lumen 112 of the variflex catheter 100 and, for example, is made of PTFE. The liner 110 acts as a lubricious pathway for implements passed through the variflex catheter 100, as well as a sealed conduit for fluids such as saline or contrast dye. The liner 110 in this exemplary embodiment has a thickness of approximately 0.01 mm.

Exemplary embodiments of the support structure of the variflex catheter 100 comprise various components that may be different and depend upon a location on the longitudinal extent of the catheter body. A proximal section 101 of the variflex catheter 100, which does not contain any variable stiffness element(s), utilizes a braid 120 as a support structure. The proximal reinforcement braid 120, which in an exemplary embodiment is made up of 16 stainless steel round wires, is disposed radially about the liner 110 to support the liner 110, prevent kinks, and transmit thrust and torque. The proximal reinforcement braid 120 is jacketed through a thermal reflow operation with, e.g., 55D Pebax, to form a cover 130 that encapsulates the proximal reinforcement braid 120 and the outer surface of the liner 110 to form a composite tubular structure (this cover 130 also encapsulates the variable stiffness element 102, a transition zone 180, and the distal tip 190 as will be described in further detail below, but may have a different durometer). A distal portion of the variflex catheter 100, which is provisioned with the variable stiffness element 102, utilizes a helical wire coil 140 as a reinforcement structure. In a particular exemplary embodiment, the distal reinforcement wire coil 140 is made from a 304V stainless steel flatwire having cross sectional dimensions of approximately 0.0015" by approximately 0.008". In this embodiment, the distal reinforcement coil 140 is both a reinforcement device for the distal portion of the variflex catheter 100 and a heater device for the variable stiffness element 102 and, therefore, is referred to herein interchangeably as either the distal reinforcement coil 140 or a heater coil 140. The heater coil 140 is wound closely over the outer surface of the distal liner 110, with a varied pitch corresponding to a desired flexibility within a given region. In an exemplary embodiment, a proximal end of the heater coil 140 overlaps the braid 120 to a given extent, for example, between approximately 5 mm and approximately 3 cm. Distal of the variable stiffness element 102, the heater coil 140 acts primarily as a reinforcement coil 140 and can extend substantially to and through the distal tip 190, as shown in FIGS. 15 and 16. Setting flexibility of a portion of the variflex catheter 100 is described herein and is not repeated here for reasons of brevity but all variations described herein and equivalents thereof are equally possible for setting the flexibility of any given portion of the variflex catheter 100.

To deliver electrical energy to a portion of the heater coil 140 designated for heating, two insulated copper conductors 150, 152 are disposed along a length of the variflex catheter 100 and are in electrical contact with the heater coil 140. At the proximal end, each conductor 150, 152 is electrically connected to a heating control system 200 at or near the handle of the variflex catheter 100. At a distal end, each conductor 150, 152 is fixed (e.g., soldered, welded, brazed) to the heater coil 140 at two end points 142, 144 of the coil 140, which locate proximal and distal boundaries of a heating portion of the heater coil 140 and, thereby, form a series circuit comprising the heating control system 200, the first conductor 150, the coil 140, and the second conductor 152. The conductors 150, 152 are wrapped around the distal portion of the variflex catheter 100 in a helical fashion, in parallel with the helix defined by the heater coil 140, and positioned so that they do not contact the heater coil 140. If properly shielded from heat, alternatively, the conductors 150, 152 can be co-wound with the heater coil 140 in a single heater sub-assembly. Within the distal section of the variflex catheter 100, the heater coil 140 and the conductors 150, 152 are both wound directly over the outer surface of the liner 110. In this region, the winding is approximately 35 turns per inch (pitch=0.0286"/0.72644 mm). Within the proximal section 101 of the variflex catheter 100, the conductors 150, 152 are laid in helical grooves melted into the cover 130 and are subsequently thermally reflowed into the proximal section 101 of the shaft of the variflex catheter 100. In this proximal region, the winding changes to approximately 1.5 turns per inch (pitch=0.667"/16.93 mm). This change in winding density is used to determine the amount of heat that will be delivered to a given section. In the section of the variflex catheter where the heat is required to melt the binder, the windings will be closely spaced to provide the greatest heating effect. In the proximal sections where heating is not required, the spacing will be wide. In an exemplary embodiment, the distal portion of the variflex catheter 100 is jacketed with low-durometer Pebax to form the cover 130 through a thermal reflow process, resulting in a flexible, durable base catheter structure that is provided with an integrated heater in a region where variable stiffness is desired, for example, the variable stiffness element 102. In this region about the variable stiffness element 102, the durometer is approximately 30D.

In an exemplary embodiment for monitoring temperature of the variable stiffness element 102, a fine-wire thermocouple 160, with an electrically insulated junction and leads, is attached through thermal bonding or adhesives, to an outer surface of a portion of the cover 130 that encapsulates the heated portion of the heater coil 140 and is positioned over the heated region of the variable stiffness element 102. In particular, a portion of the cover 130 is a jacket of, for example, Pebax that is reflowed over the heater/reinforcement coil 140 and the copper conductors. The thermocouple 160 is situated on the outside surface of the heater coil 140 under a variable flex sub-assembly 170. The leads of the thermocouple 160 are wrapped helically with the same pitch as the heater coil 140 and, in an exemplary embodiment, are separated from the windings of the heater coil 140. In a proximal direction towards the proximal heating control system 200, the leads of the thermocouple 160 are wound around the braid 120 along with the conductors 150, 152 and are also fit into helical grooves and subsequently thermally reflowed within the cover 130. One or more thermocouple areas can be positioned proximal to, at, or distal to the variable stiffness element. In the embodiment of FIG. 14, the thermocouple 160 is positioned to measure temperature within approximately the longitudinal center of the variable stiffness element 102, the wiring of which is entirely integrated into the base portions of the variflex catheter 100.

In an exemplary embodiment of the scaffold and binding material for the variable stiffness element 102, the variable flex sub-assembly 170 is positioned around and over the heated portion of the distal end of the variflex catheter 100, which, in this exemplary embodiment, comprises the section defining the variable stiffness element 102. The variable flex sub-assembly 170 comprises a braid, previously saturated with molten binder and allowed to solidify in a dimensionally controlled fashion. An exemplary method for controlling the deposition of binder on the braid comprises loading the braid over a mandrel, dip-coating the braid with molten binder, and pulling the braid and mandrel through a die with known inner diameter. By controlling the size of the mandrel and the die, the amount of binder within a given amount of braid can be regulated. An exemplary configuration for this braid is a 32-carrier, 16 PIC, full-load, standard pattern tubular braid, where each carrier is made up of seventy (70)

filaments of 22 Tex Dupont Kevlar. An exemplary material for the binding material is a blend of 90% by mass heneicosane and/or docosane and 10% by mass microcrystalline wax. As for the remainder of the variflex catheter 100, the braid and binder matrix are jacketed with a layer of low-durometer Pebax (e.g., 30D durometer), which extends axially beyond the braid/binder in both the proximal and distal directions and which is subsequently thermally reflowed into the base of the variflex catheter 100. This configuration results in a braid and binder structure that is wholly encapsulated. Alternatively, the braid is placed over the heated section and the binder material is applied in place and formed to the desired OD before the rest of the process is completed. This avoids the risk of entrapping air within the binder.

One area where the jacket 130 has a discontinuity in an exemplary embodiment is in the transition zone 180—an extent of the variflex catheter 100 between the distal tip 190 and the variable stiffness element 102. In general, improperly designed and constructed transition zones result in a failure-prone catheter, where the ends of a supporting scaffold tend to concentrate stress on the underlying base catheter within a small region, thereby greatly increasing the risk of localized deformation, kinking, and subsequent wire breakage and/or loss of lumen patency. Jacketing the transition zone 180 with the low-durometer Pebax as set forth herein ensures a smooth transition of mechanical properties between the proximal section 101 of the variflex catheter 100, which in some regions is inherently floppy, and the variable stiffness element 102, which is quite rigid in a cooled state. Effective transition zones 180 are created in the variflex catheter 100 by allowing the distal end of the scaffold portion of the variable stiffness element 102 to be as mobile as possible and by ensuring a smooth transition between the outer jacket of the cover 130 and the base catheter distal of that scaffold. Effective proximal transition zones (e.g., the distal-most part of the proximal section 101) are created by making the cover 130 around the proximal section 101 have a slightly higher durometer material relative to the cover 130 that exists at the distal portions (102, 180, 190) and beneath the proximal end of the variable stiffness element 102, and by bonding the distal-most portion of the proximal section 101 to the very proximal end of the variable stiffness element 102. Where the variable stiffness element 102 has a braid-based scaffold, this can be accomplished by infusing the proximal few millimeters of the braid with Pebax utilizing a heated die and thermally reflowing this Pebax-saturated region into the distal-most Pebax of the proximal section 101. The remaining portion of the braid is saturated in the binding material and functions as the variable stiffness element 102.

The distal-most portion of the variflex catheter 100 comprises the distal tip 190. The distal tip 190 serves to track over a guidewire or additional catheter present within the variflex catheter's inner lumen 22, 112 and, therefore, must be both flexible and kink-resistant. Because of the varied anatomical use cases for a variflex catheter 100, lengths of a distal tip for a given variflex catheter 100 can vary by design between approximately 1 mm and 20 cm. The distal tip 190 can be reinforced by a variety of constructions, including but not limited to flat-wire and round-wire coils and also wire or polymer braids. In this exemplary embodiment, reinforcement of the distal tip 190 comprises a portion of the reinforcement coil 140 disposed within the distal tip 190 and encapsulated within cover 130. Here, reinforcement coil 140 has a pitch that is greater than the pitch within the variable stiffness element of, for example, between approximately 40 and 70 windings per inch, or, in particular, approximately 52 windings per inch. Stiffness of the distal tip 190 can be varied by altering some combination of the reinforcement coil's pitch, construction, and the local durometer of the cover 130 at or adjacent the distal tip 190.

Another exemplary embodiment for stiffening the distal tip 190 simply extends one (or more) of the conductor leads (for example, conductors 150, 152) from the variable stiffness element 102 further in the distal direction. The lead or leads can be extended at the same pitch or the pitch can increase, for example, to between approximately 40 and 70 windings per inch, or, in particular, approximately 52 windings per inch.

Still a further exemplary embodiment for stiffening the distal tip 190 includes providing an independent coil of a nickel-titanium alloy (such as Nitinol). Such alloys are more resilient than the metal of the conductors (e.g., copper). Making the distal tip stiffening element of nickel-titanium alloy provides additional benefits. The tubular structure of such a coil maintains the integrity of the interior lumen 22 of the variflex catheter while, at the same time, preventing kinking of the catheter where the coil is present. Such an embodiment also increases the variflex catheter's ability to track on a guidewire and within a lumen with a decreased risk of kinking.

In various instances, it is desirable to have the distal opening of the inner lumen 22, 110, 112 of a catheter smaller than the steady state interior diameter of the remainder of the catheter. In an exemplary embodiment, a catheter (for example, the variflex catheter) has a domed tip that tracks through anatomy more smoothly than a right-angle truncated tip. One reason to have this feature is to prevent skiving of a vessel wall by a tip of the catheter. In an exemplary embodiment where the distal tip 190 of the variflex catheter has a tip structure that provides such a decreased diameter, in particular, the embodiment shown in FIGS. 24 to 28, the distal tip 190 has a structure of, for example, nitinol that heat-set into a crown-shaped dome 700 having castellations 702 defining, at a distal end, a circular opening 704. The circular opening 704 has an internal diameter smaller than the internal diameter of the inner lumen 22, 110, 112. In a particular exemplary embodiment either for a catheter or the variflex catheter, the crown-shaped dome 700 is encapsulated with a cover (e.g., cover 130) of a soft polymer (it is atraumatic for the surgical purposes in which the catheter will be used) that allows for expansion when either a fluid or an obturator is passed from the inner lumen (e.g., inner lumen 22, 110, 112) distally through the distal tip opening 704. The soft polymer encapsulant could be of many materials including, for example, PEBAX®, TPU's such as Tecoflex®, silicones, and ePTFE. The dome 700 can be of many materials including, for example, Nitinol, Platinum-Iridium alloy, stainless steel, copper alloys such as beryllium copper, and PEEK. When made of a radiopaque material, the crown-shaped dome 700 can act as distal marker band, or it can be attached to distal marker band, or be a separate entity entirely. The crown has features which allow its tip to expand radially to allow the passage of intraluminal devices. The crown-shaped dome 700 can provide the castellations 702 with a series of cuts that leave behind prongs extending from the proximal end of the crown in a distal direction.

The thermocouple leads and power conductors 150, 152 for the heater coil 140 are connected to a heating control system 200, 300 that regulates electrical output to the heater coil 140 based on temperature feedback from the thermocouple 160. In one exemplary embodiment, the regulation of the electrical output occurs through a PID loop implemented with a microcontroller. The microcontroller is provided with a user input device (e.g., a button, a switch, or a toggle) that allows the user of the variflex catheter 100 to switch the variable stiffness device 102 between the stiffened state and the softened, flexible state. The microcontroller can inform the user through a user interface (e.g., with an LED light) about the state of the variflex catheter's transition between the stiff and softened states. Differences in color and emission pattern can discretely indicate at least the "stiff", "softened", "stiffening", and "softening" states, and are used to indicate device errors. The variflex catheter 100 can be programmed to provide intermediate stiffness stages as well. In the flexible state, the control system 200, 300 adjusts the target temperature to reach a full "floppy" state for navigating tortuous anatomy and, in the stiff state, the heating control system 200, 300 removes power to the heater coil 140 to allow temperature of the variable stiffness element 102 to lower to ambient, in which state the variflex catheter 100 is intended to remain in place in the anatomy. But, additionally, the microcontroller can be programmed to place the variable stiffness element 102 in a "half-floppy" state where the user is, for example, navigating a large vessel and needs some compliance of the catheter body. For partially softened operation, the power controller is programmed to target a pre-determined intermediate temperature that is known to correspond to a mechanical state between the fully stiffened and softened states. Partially softened operation is desirable for certain maneuvers within a procedure where a balance of stiffness and flexibility are desired. An example is the crossing of a patent's aortic arch, which can require significant push force yet involve a drastic curvature.

An alternative exemplary embodiment improves safety and stiffness characteristics of the variflex catheter 100. Instead of the Kevlar braid described above (having a pitch corresponding to 16 PIC), the braid implements multiple pitches across its length. With computer-controlled braiding machines, the braid exhibits higher PIC counts at their ends and lower PIC counts in at least one center region, with transitions between the PIC counts being smooth and continuous. For example, a braid with 20 PIC ends and a 14 PIC center offers increased flexibility at the ends. This is desirable because heated variflex catheters can exhibit areas of increased stiffness beneath where the ends of the braid ultimately reside. This is due to the presence of solder joints between the conductor(s) and the heater coil, as well as the presence of additional Pebax directly distally and proximally of the braid.

Another alternative to the exemplary embodiment of the variflex catheter 100 employs the multi-phase wax described above, which can comprise 90% by mass 1,9-Nonanediol and 10% by mass microcrystalline wax and provides significant protection against overheating of tissue, such as endothelial tissues.

A further alternative to the exemplary embodiment of the variflex catheter 100 uses a variegated outer jacket, such as the one described with respect to FIGS. 8 and 9. Instead of the variable stiffness element 102 being covered by a jacket having a smooth outer surface and circular cross section, in this embodiment, the variable stiffness element 102 is covered by a jacket having a variegated, non-circular cross section. One exemplary material for the jacket is low durometer Pebax (approximately 35D durometer), which can easily be extruded through a die bearing the desired non-circular outer profile, while still providing a circular inner lumen. A length of this novel extrusion can be placed over a given portion of a catheter device and bonded or attached through adhesives, thermal bonding, or other methods commonly used in catheter construction. The result is a catheter jacket that allows significantly enhanced blood flow between the catheter's outer surface and a patient's endothelium, enhancing thermal safety, and exhibiting lessened friction with vessel walls due to the decreased contact surface area between the variflex catheter and the vessel walls.

Figure 4:
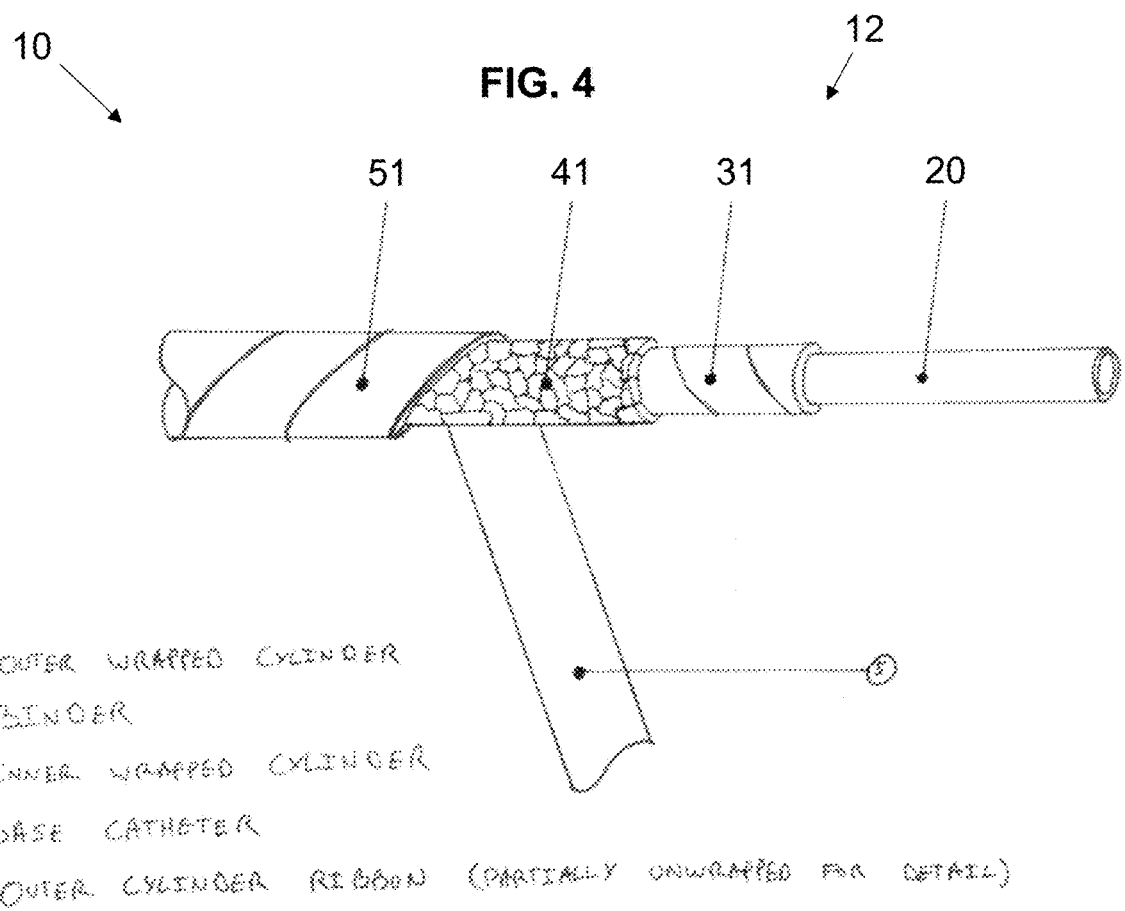
FIG. 4 is a fragmentary, perspective and partially cut away view of another exemplary embodiment of a variflex catheter having layers comprised of wrapped ribbons.

Another alternative to the exemplary embodiment of the variflex catheter 100 uses a different scaffold construction process that is compatible with the previously described base catheter, heater, binder, and jacketing technologies. This alternative scaffold is shown in FIG. 4 and comprises two ribbons of expanded PTFE (ePTFE) wrapped around the base catheter with opposite wrap directions. The ribbons are saturated with a suitable binding material and have additional binding material deposited between the two tubes formed by the wrapping. An exemplary configuration of this applied over a base catheter having a built-in heater, as previously described, provides a strip of approximately 0.001" to approximately 0.003" thick, binder-saturated ePTFE approximately 0.2" wide helically wrapped so that each wrap overlaps the previous wrap by approximately 0.05". The wrap is constrained to the area over the heater coil 140, where the variable stiffness element 102 exists. To make the saturated ribbon flexible enough to wrap in its saturated state, a hot air gun is used to soften the area of ribbon 31 about to be laid down on the interior base catheter 20. Over this wrapped ePTFE, a layer of binder 41 is deposited. One example of a controlled method of deposition is to dip coat several layers of binder 41 over the ePTFE inner wrap 31, building up a greater wall thickness than desired and then thermally reflowing the binder 41 with heat shrink tubing. The heat shrink tubing's recovered diameter and shrinkage characteristics can be used to control the amount of binder remaining over the first ePTFE layer 31. An ideal binder for this exemplary embodiment is the 90% mass heneicosane and/or docosane and 10% mass microcrystalline wax blend. Over this layer of binder 41 is wrapped a second ePTFE ribbon 51, saturated in binder 41, with the same dimensions as the first ribbon 31 but being wrapped in an opposite direction. The assembly of wrapped ribbons 31, 51 and binder 31 can then be jacketed in an appropriate material.

An additional alternative to the exemplary embodiment of the variflex catheter 100 employs a different design of the heated base catheter. The heater coil in this embodiment acts as both the base catheter's reinforcement and as a heater for the variable stiffness element and comprises two wires that are helically coiled in a bifilar fashion. In this configuration, both of the wires are made up of a material intended for heating and not simply for electrical connectivity. The two coils are parallel and out of phase with each other so that they do not contact each other. At the proximal boundary of the heated region on each of the two coils, a conductor such as a magnet wire, is provided in electrical contact with each coil. At the distal boundary of the heated region of each of the two coils, the two coils are placed in electrical contact with one another. In this configuration, a series circuit is formed from one electrical conductor, one coil, the distal joint between the coils, the second coil, and the second electrical conductor. A highly desirable aspect of this configuration is that the heater exhibits no electrical inductance, due to the configuration of parallel coils and reversed current flow between one helix and the other. This maximizes heater efficiency when the heater is powered by any type of alternating current by eliminating the phased delay between voltage and current in the heater. Practically speaking, such a configuration can be constructed with the same stainless steel flatwire described in prior embodiments. Using a coil winder, two coils are wound onto a catheter liner in a bifilar, non-touching fashion, and secured—by mechanical engagement alone, through an adhesive, or through melting into a thermopolymer strike layer present over the liner as is common in catheter construction. Electrical connection to the coils' proximal ends can be established though soldering copper magnet wires at appropriate locations on the coils. These magnet wires are helically wrapped about and integrated into the proximal shaft of the catheter as previously described. Electrical contact between the coils' distal ends is established by wrapping a tertiary, fine-wire marker coil over the two stainless steel coils and soldering the three coils together at that location. The tertiary coil can, for example, be made up of 0.001" diameter platinum wire, wound for a distance of approximately 0.02" with an approximately 0% air gap. This tertiary coil then acts not only as a connector between the two heater coils, but also as a radiopaque marker band. This configuration is provided with a temperature sensor and then jacketed with a suitable material and used as a base catheter for a multitude of variable stiffness element designs.

The conductors mentioned above are separate coils (in an exemplary embodiment, they are installed simultaneously). There is no structure that keeps the conductors separated from one another about the inner structure of the catheter. Accordingly, there exists the possibility that the conductors could move before being encapsulated and, possibly, short by touching one another. Also, it is not insubstantial to lay down parallel conductors about an inner lumen that is 8F or less in a final outer diameter. In an alternative or supplementary configuration, instead of being separate components, the conductors can be laminated together into a multifilament and wound about the catheter's inner structures as a single component. Such a configuration makes the winding of the catheter's coils much simpler because, effectively, only one structure is being wound onto the interior liner/mandrel. To further increase ease of assembly, the multifilament can be selectively laser stripped before winding, which creates precisely ablated windows in the wire/wires' insulation where soldering or other techniques are used to electrically and/or mechanically join the wires. This laser stripping is especially useful for creating the thermocouple or RTD junctions, and also junctions between heater leads, as mentioned herein.

Figure 17:
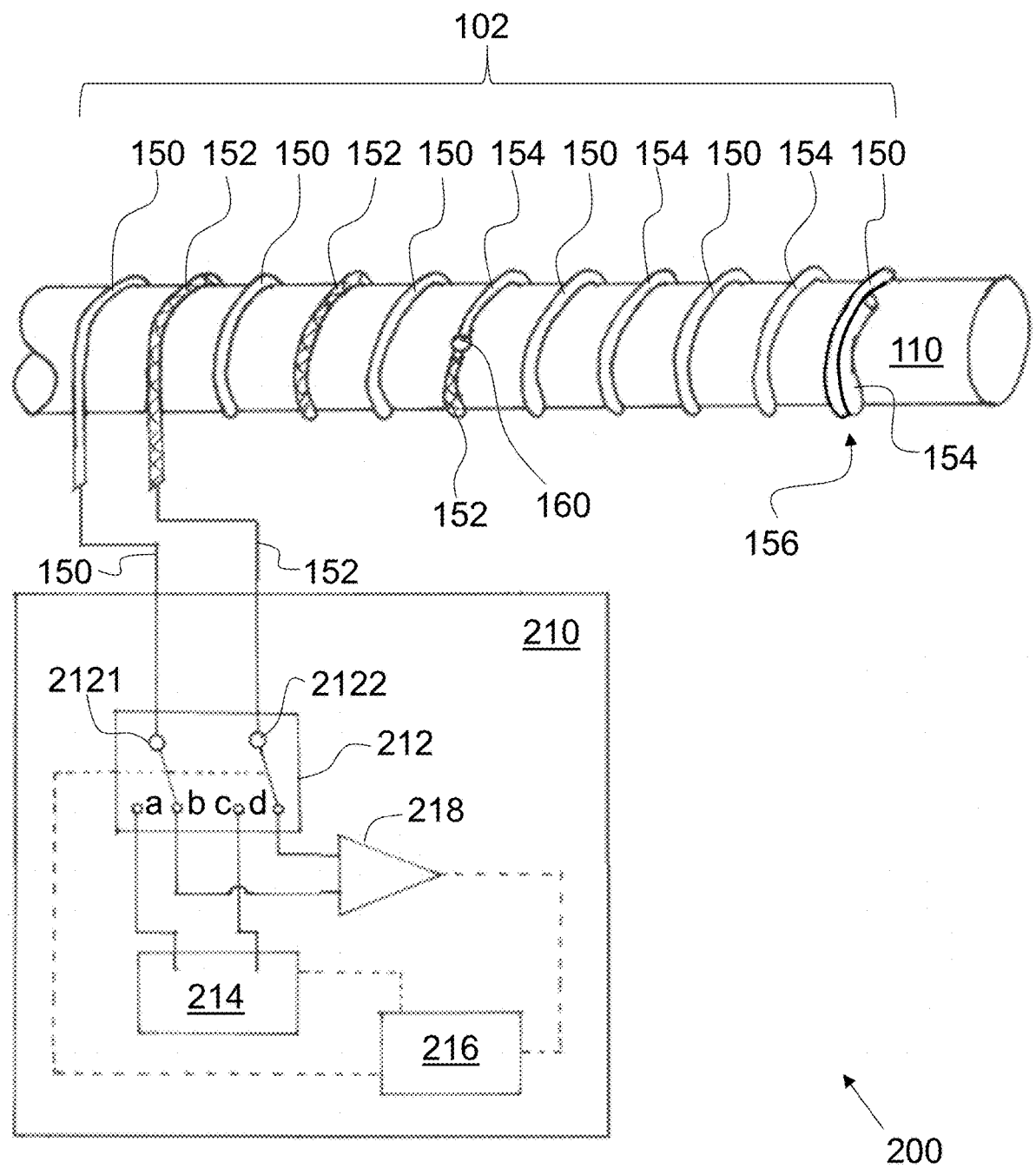
FIG. 17 is a fragmentary, perspective view of a portion of an exemplary embodiment of a heater subassembly connected to a block circuit diagram of an exemplary embodiment of a heater control system for the variflex catheter.

Shown in FIG. 17 is an exemplary embodiment of a heating control system 200 of the variflex catheter 100. This embodiment is an example of the bifilar heater configuration described herein where a parallel pair of wires are wound around an inner mandrel or cylinder to make a combined helix (as compared to the herein-described embodiment where two conductors 150, 152 are electrically connected to a separate heater coil 140, possibly made of a different material as the conductors 150, 152). In particular, two conductive heating conductors 150, 152 extend in a helix at a first pitch from the proximal heating controller 210 along the liner 110 up to the variable stiffness element 102. Because the conductors 150, 152 actually supply heat, and due to the fact that heat is primarily desired only at the variable stiffness element 102, the conductors 150, 152 have a wide pitch in this proximal section 101. For example, the pitch is approximately 1.5 wraps per inch. With such a configuration, heat imparted to the proximal section 101 is negligible. At the variable stiffness element 102, in comparison, the conductors 150, 152 change pitch to, for example, between 50 and 80 wraps per inch, between 60 and 70 wraps per inch or, in a particular exemplary embodiment, at approximately 67 wraps per inch (for example, there is an approximately 0.015" separation distance between each successive turn). The conductors 150, 152 extend with this higher pitch throughout the variable stiffness element 102 and terminate at a connection point 156 at the distal end of the variable stiffness element 102.

In a configuration where the conductors 150, 152 are merely electrical conductors (for example, they do not provide reinforcement), they are entirely separate from a reinforcement coil, which configuration is not illustrated in FIG. 17 but would wind the reinforcement coil with the same pitch as the conductors 150, 152 to be separate therefrom. Alternatively, the conductors 150, 152 can be both a heating coil and a reinforcement coil, for example. In such an alternative embodiment, the conductors 150, 152 can be made from a 304V stainless steel flatwire having cross sectional dimensions of approximately 0.0015" by approximately 0.008".

If the conductors 150, 152 are made from the same material, then the connection point 156 merely forms an endpoint for the heater of the variable stiffness element 102. However, as described, it is desirable to provide at least one thermocouple 160 within the heating portion of the variable stiffness element 102; in other words, it is beneficial to coalesce the temperature sensor and heater components into one set of wires. This can be done in a relatively straightforward manner by providing the conductors 150, 152 with different material properties. The wire materials must function for ohmic heating at safe voltages and also act as a well-characterized thermocouple when a junction is formed between the two wires. In this embodiment, shown in FIG. 17, the distal portion of the base catheter is provided with a bifilar coil that acts as both a temperature sensor and a heater (and potentially also as a mechanical reinforcement). The wires of the bifilar coil are composed of two different materials, chosen for their mechanical and electrical properties. Electrically speaking, the two materials must be such that a junction formed between them exhibits the Seebeck effect, which allows temperature measurement. The Seebeck effect results in a conversion of heat into electricity across a junction between two different metals. The voltage generated between the junction and the ends of the wires used corresponds to temperature at the junction and can be converted to a numerical temperature value through amplification and algebraic manipulation. The materials' Seebeck coefficient must be known, as well as the temperature at the opposite ends of the wires (for example, the cold junction). In the embodiment of FIG. 17, the heater conductors 150, 152 have materials selected to provide these characteristics, for example, one is formed from alumel and one is formed from chromel, which form a well-characterized K-type thermocouple when joined. A first of the heater conductors 150 extends from the heating controller 210 all the way to the distal end of the variable stiffness element 102 to the connection point 156. The second conductor 152 extends from the heating controller 210 to (in this exemplary embodiment) approximately a midpoint of the variable stiffness element 102. At its termination, the second conductor 152 is connected to a separate third conductor 154 that is made from the same material as the first conductor 150. The third conductor 154 continues the wrap of the second conductor 152 all the way to the connection point 156 and is electrically conductively connected to the distal end of the first conductor 150. This connection can be by welding, mechanical contact, or any other equivalent process that does not create an additional thermocouple at the point of connection through the incidental creation of an additional bimetallic junction. In such a configuration, a complete heater circuit is formed from the first conductor 150, to the third conductor 154, to the second conductor 152 with a material discontinuity at the midpoint of the variable stiffness element 102 forming a thermocouple 160.

The bifilar coil is connected to a heating controller 210 that is able to multiplex the coil's leads between a controlled voltage source and a signal amplifier appropriate for thermocouple measurement. In particular, the proximal ends of the first and second conductors 150, 152 are connected to a switching element 212 (e.g., a multiplexer) having two switching states. In a first switching state (not shown in FIG. 17), where switches 2121 and 2122 are respectively connected to terminals a and c, the heater circuit is connected to a power supply 214 (illustrated as constant voltage source but able to output heater power through any of the here-described modulation schemes and, therefore, can be a battery and/or a mains). In a second switching state shown in FIG. 17, switches 2121 and 2122 are respectively connected to terminals b and d and the heater circuit completes a thermocouple control circuit that comprises at least a microcontroller 216 and a thermocouple amplifier 218 (one or both of which are connected to the power supply 214). When in the second switching state, the thermocouple control circuit utilizes the power of the dissimilar materials of the conductors 150, 152, 154 to enable the ability to detect temperature of the variable stiffness element 102 at the location of the thermocouple 160. During operation, the heating controller 210 repeatedly switches between applying power to the coil (thereby heating it) and measuring temperature through the coil, thus providing feedback on an appropriate level of power and various safety conditions. An appropriate power output is dictated by the microcontroller 216, calculated by an algorithm as herein described in the section on control algorithms. Safety conditions such as heater continuity and insulation integrity can also be measured. The junction between the two chosen materials is disposed at a location where a temperature of interest exists, which, in FIG. 17, exists at approximately the center of the heated region of the coil (150, 152, 154).

Figure 18:
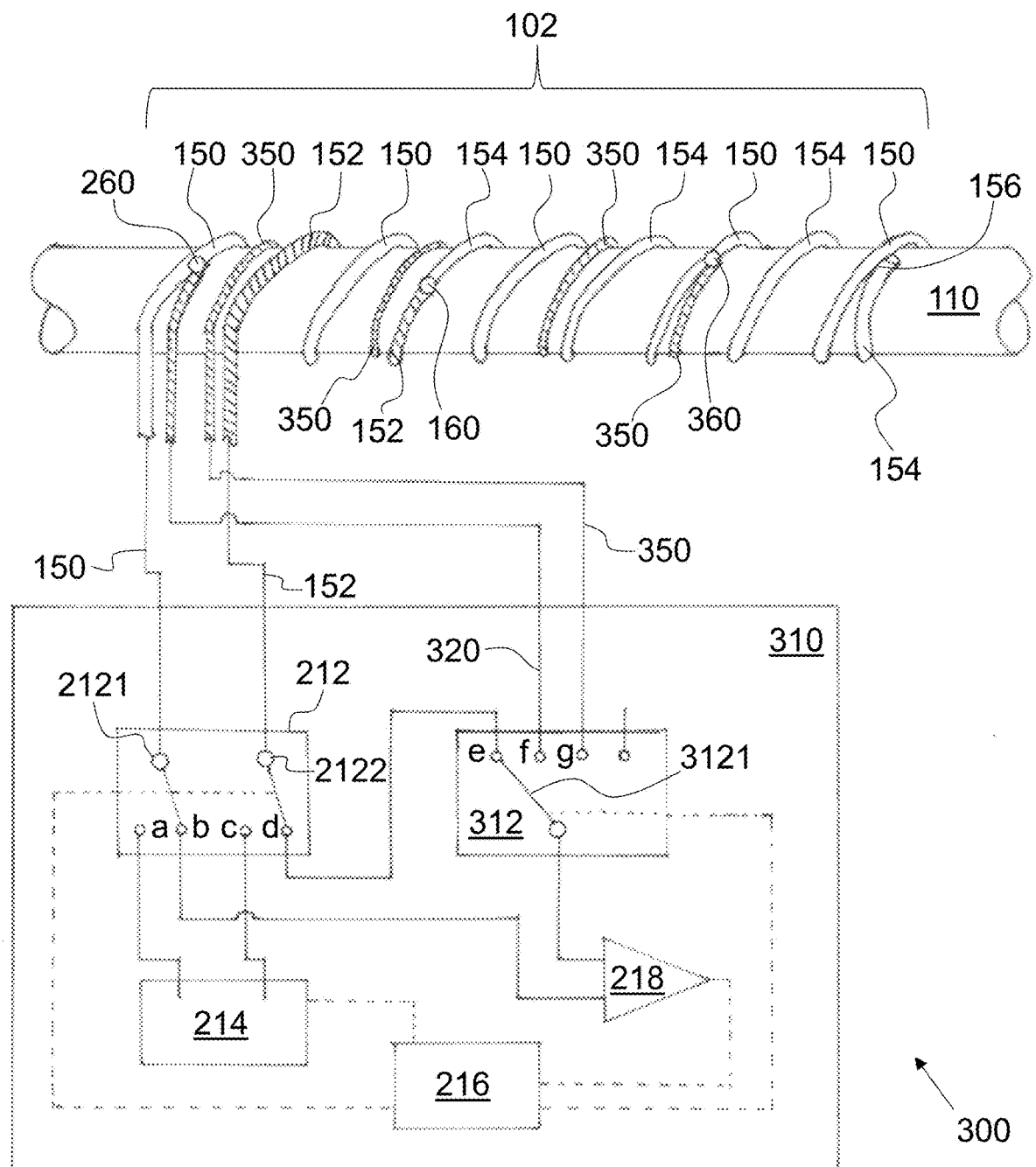
FIG. 18 is a fragmentary, perspective view of a portion of an exemplary embodiment of a heater subassembly connected to a block circuit diagram of another exemplary embodiment of a heater control system for the variflex catheter.

The configuration shown in FIG. 17 illustrates a single thermocouple junction within the variable stiffness element 102. In an alternative exemplary embodiment, FIG. 18 illustrates how a heating control system 300 can include three (or more) thermocouple junctions with the addition of only one wire per new junction (this is contrasted with the requirement of two wires per thermocouple junction for standalone thermocouples). In particular, the heater conductors 150, 152 for the first thermocouple 160 have materials selected to provide these characteristics, for example, the first conductor 150 is formed from alumel and the second conductor 152 is formed from chromel, which form a well-characterized K-type thermocouple when joined. The first conductor 150 extends from the first terminal 2121 of the first switching device 212 of the heating controller 310 all the way to the distal end of the variable stiffness element 102 to the connection point 156. The second conductor 152 extends from the second terminal 2122 of the first switching device 212 of the heating controller 310 to (in this exemplary embodiment) approximately a ⅓-point of the variable stiffness element 102. At its termination, the second conductor 152 is connected to a separate third conductor 154 that is made from the same material as the first conductor 150—this connection point forming the first thermocouple 160. The third conductor 154 continues the wrap of the second conductor 152 all the way to the connection point 156 and is electrically conductively connected to the distal end of the first conductor 150. This connection can be formed by welding, mechanical contact, or any other equivalent process that does not create an additional thermocouple at the point of connection through the incidental creation of an additional bimetallic junction. In such a configuration, a complete heater circuit is formed from the first conductor 150, to the third conductor 154, to the second conductor 152 with a material discontinuity at the ⅓-distal-point of the variable stiffness element 102 forming the first thermocouple 160.

As for the embodiment of FIG. 18, the bifilar coil is connected to the heating controller 310, which is able to multiplex the coil's leads between a controlled voltage source and a signal amplifier appropriate for thermocouple measurement. In particular, the proximal ends of the first and second conductors 150, 152 are connected to first and second terminals 2121, 2122 of the first switching element 212 having two switching states. In a first switching state (not shown in FIG. 18), the heater circuit is connected to the power supply 214 (illustrated as constant voltage source but able to output heater power through any of the here-described modulation schemes and, therefore, can be a battery and/or a mains). In a second switching state shown in FIG. 18, the heater circuit is connected to a thermocouple control circuit that comprises at least the microcontroller 216 and the thermocouple amplifier 218 (one or both of which are connected to the power supply 214). When in the second switching state of the first switching element 212, the thermocouple control circuit utilizes the power of the dissimilar materials of the conductors 150, 152, 154, 320, 350 to enable an ability to detect temperature of the variable stiffness element 102 at a location of respective thermocouples 160, 260, 360. In the second switching state of the first switching device 212, a second switching device 312 (e.g., a multiplexer) can be used to connect each of the first, second, and third thermocouples 160, 260, 360 with the control circuit (e.g., 216, 218). When in the switching states connecting the various the conductors 150, 152, 154, 320, 350, the heating controller 310 enables an ability to detect temperature of the variable stiffness element 102 at any location of the thermocouples 160, 260, 360. During operation, therefore, the heating controller 310 repeatedly switches between applying power to the coil (thereby heating it) and measuring temperature through the coil at either of the first, second, and third thermocouples 160, 260, 360, thus providing feedback on an appropriate level of power (through a control algorithm). Here, the junctions between the two chosen materials are disposed at locations where temperatures of interest exist, namely at approximately the proximal end, at the ⅓-distal-point, and at the ⅔-distal-point of the heated region of the coil.

To select between each of these thermocouples 160, 260, 360, the second switching device 312 has three switching connections e, f, g to which the internal switch 3121 can connect. When in the first switching state connected to terminal e, the heating controller 310 is connected to the first thermocouple 160 through the first conductor 150, the second conductor 152, and the third conductor 154. When in the second switching state connected to terminal f, the heating controller 310 is connected to the second thermocouple 260 through the first conductor 150 and a fourth conductor 320. To complete the connection to the second thermocouple 260, the fourth conductor 320 extends from terminal f of the second switching device 312 to approximately a proximal end of the variable stiffness element 102. At its termination, the fourth conductor 320 is connected to the first conductor 150 and, therefore, is made from a material that is different from the first conductor 150 (e.g., it can be the same material as the second conductor 152). This connection can be by welding, brazing, soldering, with a conductive epoxy, or through any equivalent process. Accordingly, when the heating controller 310 switches the second switching device 312 to terminal f and the first switch 2121 of the first switching device 212 is switched to terminal b, the second thermocouple 260 can be monitored for temperature at approximately the proximal end of the variable stiffness element 102.

Finally, when in the third switching state connected to terminal g, the heating controller 310 is connected to the third thermocouple 360 through the first conductor 150 and a fifth conductor 350. To complete the connection to the third thermocouple 360, the fifth conductor 350 extends from terminal g of the second switching device 312 to approximately a ⅔-distal-point of the variable stiffness element 102. At its termination, the fifth conductor 350 is connected to the first conductor 150 and, therefore, is made from a material that is different from the first conductor 150 (e.g., it can be the same material as the second conductor 152). This connection can be by welding, brazing, soldering, with a conductive epoxy, or through any equivalent process. Accordingly, when the heating controller 310 switches the second switching device 312 to terminal g and the first switch 2121 of the first switching device 212 is switched to terminal b, the third thermocouple 360 can be monitored for temperature at approximately the ⅔-distal-point of the variable stiffness element 102.

The 3-wire configuration incorporates a sensing wire to measure the voltage at one side of the sensing element. This voltage is then used to compensate the resistance of the connection between the measurement circuit and the sensing element. A 3-wire RTD can be configured from the catheter pictured in FIG. 18. As in the two-wire configuration, wires 150, 152, and 154 combine to form a single length 150-152-154 to deliver probing current to the sensing element. The additional sensing wire can be either wire 320 or 350. In an exemplary embodiment, wire 350 is used as the sensing wire but both wires 320 and 350 will work in the same manner. The addition of this sensing wire 350 allows the sensing element to be effectively divided at junction 360. This is accomplished by sending a probing current from the power controller 214 through the sensing element 150-152-154 by connecting point 2121 with contact a and connecting point 2122 with contact c. The voltage across the sensing element 150-152-154 can now be sampled in two locations. First, the op-amp 218 is connected through switch 3121 to contact g and measures voltage with respect to point 2121 and contact b. A second voltage measurement can be made by connecting the op-amp through switch 3121 to contact g and measures voltage with respect to point 2122 and contact b. These two voltage measurements can be used along with the probing current to calculate a resistance of the wires 150 and 154 between points 2121 and junction 360, and the resistance of wire 152 between the switch 3121 and junction 360. However, in a 3-wire configuration, the resistance of only one of the connections of the measurement circuit is compensated. It is typically assumed that if the connections are the same size and near one another they have the same resistance.

In the variflex catheter 100, configuration of an RTD can be accomplished in different ways, each having its advantages in terms of complexity and accuracy. The first and simplest configuration is a two-wire RTD. The catheter pictured in FIG. 17 can be configured as a two-wire RTD circuit. Wires 150 and 152 are combined to form the sensing element. The combined resistance of the wires 150, 152 is measured by sending a current from the power module 214 through the points 2121 and 2122 of the switch at contacts a and c. The voltage is simultaneously measured with the op-amp 218 through the switch points 2121 and 2122 at contacts b and d. This means that, for using the circuit of FIG. 17 as a two-wire RTD, contact a is electrically connected to either contact b or point 2121 and contact c is electrically connected to either contact d or point 2122. With a known current and voltage passing across the sensing element (wires 150, 152), the resistance of these wires 150, 152 between points 2121 and 2122 can be determined. This resistance then can be converted to a temperature using the known thermal coefficient of resistance of the wires 150, 152. Two-wire configurations are typically used where the sensing element is placed near the measurement circuit. This is because the additional resistance of the connections to and from the desired sensing points is negligible when the distance between points 2121 and 2122 are very close to the area to be measured, but that resistance is relatively large when the points are far away from the measuring circuit, for example, when the measurement circuit 210 is within the handle of the catheter at the opposite end of the device. Any change in the temperature of the transmitting wire will add to the total resistance measurement and contribute to error when determining the temperature of the sensing element. When increasing the distance from the sensing circuit to the measurement points, addition of sensing wires helps compensate for the additional resistance of the transmission wires. This is where 3-wire and 4-wire RTD configurations are utilized to reduce error. A 4-wire configuration utilizes two sensing wires on either side of the sensing element, thereby isolating the voltage measurement only to the desired section of the catheter. This configuration can be explained and used from the circuit of FIG. 18 by combining wires 150, 152, and 154 to form a single sensing element 150-152-154 to deliver probing current. RTD temperature sensing is accomplished by sending a known current from the power module 214 through the multiplexing module 212 by connecting point 2121 to contact a and by connecting point 2122 to contact c. Wires 320 and 350 are then employed as the two sensing wires, allowing the controller 310 to measure voltage across the two connection points 260 and 360. This circuit forms a sensing element between points 260 and 360 using wire 150. The voltage is measured with the op-amp 218 at the contacts g and f through the multiplexer 312. Because the input of the op-amp 218 is of high impedance, the current across wires 320 and 350 is negligible, allowing for the resistance to also be neglected. Therefore, measurements at points f and g in the multiplexer 312 reflect voltages at the points 260 and 360, respectively. Using a known probing current and the voltages measured at point 260 with respect to point 360, a resistance of the sensing element can be determined using a known thermal coefficient of resistance. This provides the greatest accuracy when the sensing element is placed at a distance from the measurement circuit, such as at the proximal control handle of the catheter 100.

Descriptions for typical 2-wire, 3-wire, and 4-wire RTD circuits may be found in the article Minimize Measurement Errors in RTD circuits by Gordon Lee, published in EDN on Feb. 1, 2016 at http://www.edn.com/design/test-amd-measuremetn/4441311/Minimize-measurement-errors-in-RTD-circuits, which is incorporated herein by reference.

Because RTDs are useful to accurately sample temperature of an external medium, they can be used in the variflex catheter 100 instead of or in addition to thermocouples. To maintain highest accuracy, typically the probing current of the RTD is kept to a minimum to keep self-heating of the sensing element to a minimum. As a result, the resistance of the RTD sensing element is relatively high. This keeps the voltage drop across the RTD sensing element in an acceptable range for accurate measurement. Advantageously, for use in the variflex catheter 100, the sensing element is also utilized as the heating element. This allows for the self-heating error of a typical RTD sensing configuration to be ignored, which allows for larger current to be applied to the sensing/heater element to deliver the required power for heating. Increasing the current proportionally increases the voltage drop across the sensing element. In an alternative embodiment, the resistance of the sensing element is decreased proportionally when the current is increased, maintaining the same voltage drop. This provides an additional advantage of keeping the voltage supply low and maintaining the ability to deliver the required power level for heating.

In another exemplary embodiment, the two sensing wires in a 2-wire RTD circuit can be comprised of dissimilar metals to form a thermocouple junction along with to the heater supply wires. Constructing the catheter shown in FIG. 17 with dissimilar wires 150 and 152 forms a thermocouple junction at point 160. Variations of such a configuration allow for a discrete temperature measurement to be taken anywhere along the length of the catheter 102 by measuring the voltage between points 2121 and 2122 by connecting these points 2121, 2122 to the op-amp 218 through contacts b and d, respectively. Such a configuration give the ability to obtain two different temperature measurements from the same circuit, a two-wire RTD measurement and a thermocouple measurement. This technique of employing thermocouple junctions can also be applied to the 3-wire and the 4-wire RTD configurations described herein. In the 3-wire and 4-wire RTD implementations, two or three thermocouple junctions can be formed. This configuration, shown in FIG. 18, has wires 150 and 154 be comprised of one material, connected at point 156, and wires 152, 350, and 320 are comprised of another different material. Such a configuration forms thermocouple junctions at points 160, 260, and 360. In the three-wire configuration, one of the wire and junction pairs are omitted, either wire 320 and junction 260 or wire 350 and junction 360. The voltage at the junction is measured in the same manner as the 2-wire configuration by connecting the wires with the dissimilar metals to the op-amp 218. By constructing the 3-wire and 4-wire RTD circuits with dissimilar metals, multiple temperature measurements can be made along a length of the catheter 100, providing redundancy and self-checking by comparing the measurements.

Figure 35:
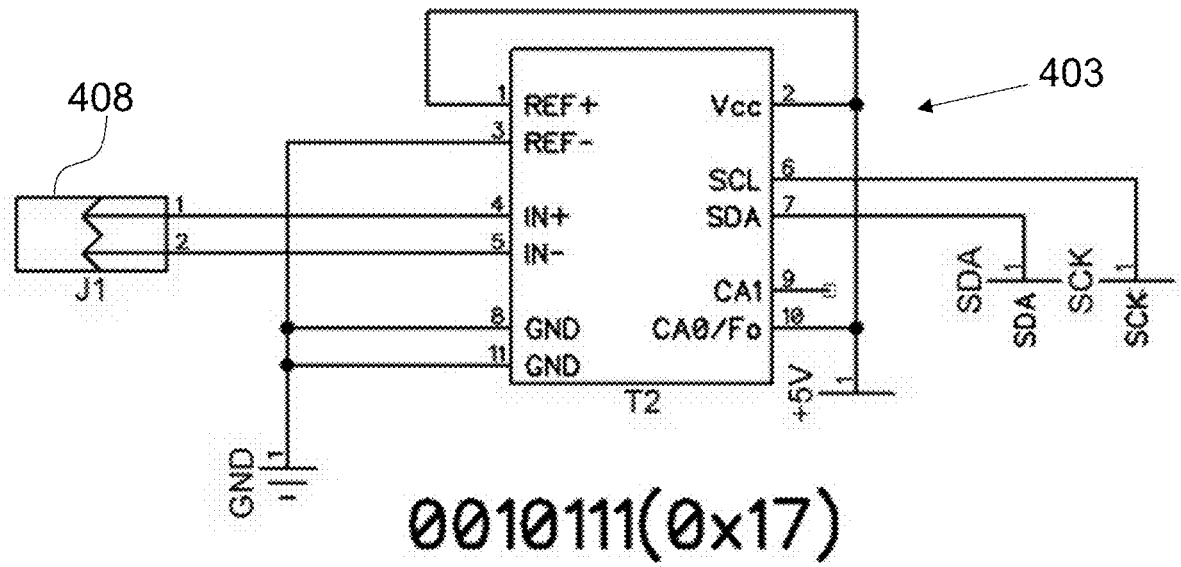
FIG. 35 is a schematic circuit diagram of an exemplary embodiment of a thermocouple amplifier subassembly for the heater control system of FIG. 29.
Figure 36:
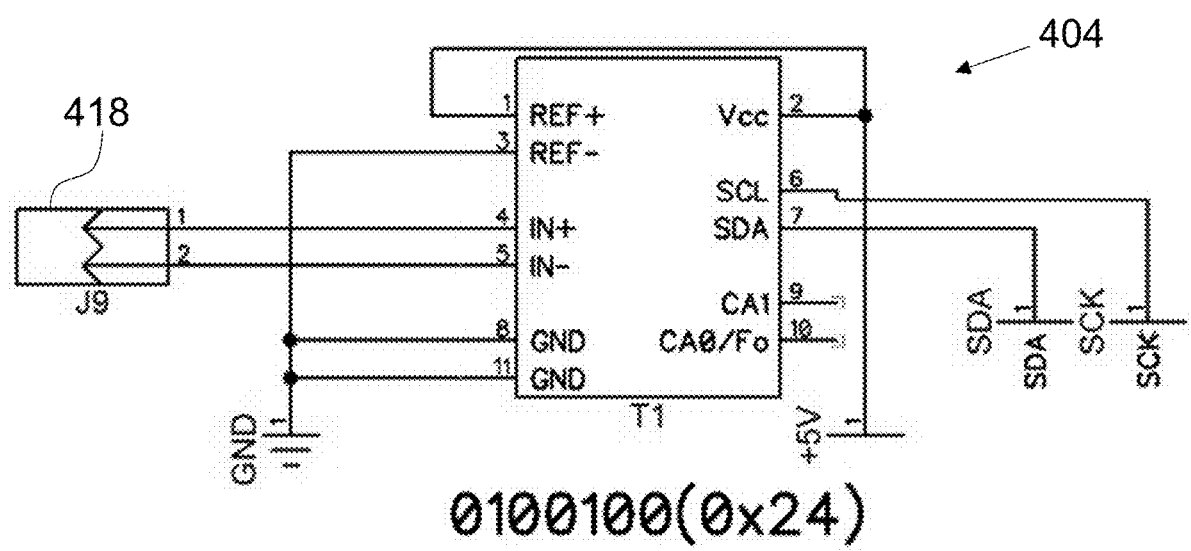
FIG. 36 is a schematic circuit diagram of an exemplary embodiment of a thermocouple amplifier subassembly for the heater control system of FIG. 29.

The schematic circuit diagrams of FIGS. 29 to 36 illustrate an exemplary embodiment of a control system 400 used to operate the variflex catheter. As shown starting in FIG. 29, the control system 400 is controlled by a microcontroller 401, which receives control inputs from an operator switch 409. In an exemplary embodiment of an operator switch 409 that is a pushbutton, resistor 424 pulls the input to the microcontroller 401 high when the operator switch 409 is not pressed, allowing that input to be pulled low when the operator switch 409 is pressed. Operator feedback is provided by the microcontroller 401 controlling outputs to an RGB LED, which comprises LEDs 413, 414, and 415. Current through these LEDs 413, 414, 415 is controlled by resistors 410, 411, and 412, respectively. Software programs are introduced into the microcontroller 401 by an in-circuit-self-programming (ICSP) connector 417. Data is output from the microcontroller 401 to a remote data logging system through a serial data port 416. An output from the microcontroller 401 is connected to a control gate of metal-oxide-field-effect-transistor (MOSFET) 406, which controls the charging and discharging of a gate of MOSFET 406, causing the MOSFET 406 to turn on (become conductive, allowing current to flow to the heater) and off (turning off current to the heater). Resistor 425 pulls down a gate voltage of the MOSFET 406 to ensure a definite and rapid discharge of the gate of the MOSFET 406. A connector 407 is connected to the heater of the variflex catheter (e.g., the heater coil 140) and provides current to heat the variable stiffness element 102 of the catheter. A power source 419 (e.g., a battery) shown in FIG. 30 provides power to operate the control system 400 and to heat the heater coil 140. Capacitor 420 in FIG. 31 provides charge storage to smooth the delivery of power from the power source 419 and to absorb transient loads. A voltage regulator 405 shown in FIG. 32 reduces the voltage of the power source 419 to a suitable voltage (e.g., to 5 v) to operate the control system 400. Capacitor 421 smooths voltage from the regulator 405 and absorbs transient loads as shown in FIG. 33. Resistors 422 and 423 in FIG. 34 provide the required voltage pullup to communication lines between the microcontroller 401, a power-sensor 402, and thermocouple amplifiers 403, 404 (FIGS. 35 and 36, respectively). Thermocouple amplifiers 403, 404 receive millivolt signals from thermocouples in the variflex catheter through connectors 408 and 418, respectively. The thermocouple amplifiers 403, 404 provide serial data to the microcontroller 401, including millivoltage signals from the catheter thermocouples (e.g., 160, 260, 360) and an ambient temperature of a non-illustrated circuit board of the control system 400, so that temperature compensation can be calculated by the microcontroller 401 in order to calculate an actual temperature of each thermocouple junction. In an exemplary embodiment, the power-sensor 402 is an integrated circuit that measures voltage, current, and power being delivered to the heater and provides that digital data to the microcontroller 401 so that the microcontroller 401 may calculate an actual power being delivered to the heater in the variflex catheter. Some modes of control may utilize voltage, current, and power data by calculating a resistance of the heater (and, from that, its temperature). Temperature calculated from heater resistance may be used to control the catheter temperature or may be used to supply a redundant temperature measurement for additional safety.

The designs of heating a selected section of a catheter to melt a binder can also be applied without the binder to any "normal" catheter without the binder and matrix. The selective heating of materials can reduce their stiffness locally and momentarily to allow the catheter to be more easily advanced through tortuous anatomy. And the subsequent discontinuing of heating would then return the original material properties and associated supportiveness.

It is noted that various individual features of the inventive processes and systems may be described only in one exemplary embodiment herein. The particular choice for description herein with regard to a single exemplary embodiment is not to be taken as a limitation that the particular feature is only applicable to the embodiment in which it is described. All features described herein are equally applicable to, additive, or interchangeable with any or all of the other exemplary embodiments described herein and in any combination or grouping or arrangement. In particular, use of a single reference numeral herein to illustrate, define, or describe a particular feature does not mean that the feature cannot be associated or equated to another feature in another drawing figure or description. Further, where two or more reference numerals are used in the figures or in the drawings, this should not be construed as being limited to only those embodiments or features, they are equally applicable to similar features or not a reference numeral is used or another reference numeral is omitted.

The foregoing description and accompanying drawings illustrate the principles, exemplary embodiments, and modes of operation of the systems, apparatuses, and methods. However, the systems, apparatuses, and methods should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the systems, apparatuses, and methods as defined by the following claims.

What is claimed is:

1. A catheter for use in a human body, comprising:
    a heater control system supplying power;
    a handle associated with the heater control system;
    a base catheter extending from the handle, defining an inner lumen, and comprising:
        a proximal section connected to the handle; and
        a distal segment; and
    a variable stiffness element comprising:
        a resistance heater conductively connected to the heater control system to receive power therefrom, extending distally from the heater control system, and coiled about the inner lumen at least at the distal segment, the resistance heater comprising:
            a shaft portion of a first metallic conductive material at the proximal section; and
            a heater portion of a second metallic conductive material at the distal segment;
        a hollow, outer jacket disposed at east about the heater portion; and
        a variable flex sub-assembly between the base catheter and the outer jacket and comprising a continuous reinforcement scaffold electrically independent from the heater and a binding material, and
            without power supplied to the heater when in the human body, the binding material is at a stiffened state;
            responsive to heating of the binding material by supplying power to the heater, the binding material changes to a softened state so that the variable flex sub-assembly has increased flexibility at least at the distal segment; and
            responsive to removing power, supplied to the heater to thereby allow the binding material to cool, the binding material changes to the stiffened state so that the variable flex sub-assembly has decreased flexibility at least at the distal segment.

2. The catheter according to claim 1, wherein the first metallic conductive material and the second metallic conductive material are the same.

3. The catheter according to claim 1, wherein the shaft portion of the first metallic conductive material and the heater portion of the second metallic conductive material comprise a continuous wire of the same metallic conductive material.

4. The catheter according to claim 1, wherein the shaft portion of the first metallic conductive material and the heater portion of the second metallic conductive material comprise an integral wire of the same metallic conductive material.

5. The catheter according to claim 1, wherein at least the heater portion of the heater is coiled at the distal segment as a support structure sufficient to substantially prevent kinking and substantially maintain circularity of the base catheter at the distal segment.

6. The catheter according to claim 1, wherein:
    the first metallic conductive material is one of copper, a copper alloy, and beryllium copper; and
    the second metallic conductive material is one of copper, a copper alloy, and beryllium copper.

7. The catheter according to claim 1, wherein the heater has a given pitch at the shaft portion and a pitch at the distal segment less than the given pitch.

8. The catheter according to claim 7, wherein the given pitch is one of infinite and non-infinite.

9. The catheter according to claim 7, wherein the given pitch is approximately 16.93 mm and the pitch at the distal segment is approximately 0.72644 mm.

10. The catheter according to claim 9, wherein the base catheter comprises a distal tip adjacent the distal segment and which further comprises a reinforcement coil at the distal tip.

11. The catheter according to claim 1, which further comprises a temperature-sensing element at the distal segment communicating with the heater control system to supply a value of temperature at the temperature-sensing element to the heater control system, the heater control system configured to regulate the power supplied to the heater to control temperature of the distal segment based upon the value.

12. The catheter according to claim 11, wherein the temperature-sensing element is a thermocouple junction independent from the heater.

13. The catheter according to claim 11, wherein the temperature-sensing element is a thermocouple junction in line with the heater.

14. The catheter according to claim 11, wherein the temperature-sensing element is a thermocouple junction integral with the heater.

15. The catheter according to claim 1, wherein the outer jacket is disposed about the base catheter and extends proximally from the variable stiffness element along the inner lumen and adjacent the handle.

16. The catheter according to claim 1, wherein the scaffold is a 32-carrier, 16 PIC, full-load, standard pattern tubular braid, each carrier being made up of 70 filaments of 22 Tex Dupont Kevlar.

17. The catheter according to claim 1, wherein the scaffold is braided support tube of a non-conductive para-aramid synthetic fiber.

18. The catheter according to claim 1, wherein the binding material is a blend of microcrystalline wax and at least one of heneicosane, tricosane, docosane, eicosane, nonadecane, and octadecane.

19. The catheter according to claim 1, wherein the binding material is a blend of approximately 90% by mass of at least one of heneicosane and docosane and approximately 10% by mass of microcrystalline wax.

20. The catheter according to claim 1, wherein the heater control system heats the heater to a temperature above body temperature and, responsive to removing power supplied to the heater, the variable stiffness element cools to approximately body temperature.

21. The catheter according to claim 1, wherein the heater control system heats the heater up to approximately up to 45° C.

22. The catheter according to claim 1, wherein the heater control system is within the handle.

23. The catheter according to claim 1, wherein the heater control system is separate from the handle.

\* \* \* \* \*